US012742001B2

(12) United States Patent
Velasquez et al.

(10) Patent No.: US 12,742,001 B2
(45) Date of Patent: Sep. 22, 2026

(54) CHIMERIC ANTIGEN RECEPTORS WITH CD20 SAFETY SWITCH

(71) Applicant: ST. JUDE CHILDREN'S RESEARCH HOSPITAL, INC., Memphis, TN (US)

(72) Inventors: Mireya Paulina Velasquez, Memphis, TN (US); Stephen Gottschalk, Germantown, TN (US); Janice Riberdy, Memphis, TN (US); Albert Zhou, Memphis, TN (US); Byoung Ryu, Memphis, TN (US); Abishek Vaidya, Memphis, TN (US); Giedre Krenciute, Memphis, TN (US)

(73) Assignee: ST. JUDE CHILDREN'S RESEARCH HOSPITAL, INC., Memphis, TN (US)

( * ) Notice: Subject to any disclaimer, the term of this patent is extended or adjusted under 35 U.S.C. 154(b) by 1189 days.

(21) Appl. No.: 17/602,892

(22) PCT Filed: Apr. 10, 2020

(86) PCT No.: PCT/US2020/027719

§ 371 (c)(1),
(2) Date: Oct. 11, 2021

(87) PCT Pub. No.: WO2020/210665

PCT Pub. Date: Oct. 15, 2020

(65) Prior Publication Data

US 2022/0195007 A1 Jun. 23, 2022

Related U.S. Application Data

(60) Provisional application No. 62/833,337, filed on Apr. 12, 2019.

(51) Int. Cl.

| | |
|---|---|
| ***C07K 14/725*** | (2006.01) |
| ***A61K 40/11*** | (2025.01) |
| ***A61K 40/31*** | (2025.01) |
| ***A61K 40/42*** | (2025.01) |
| ***A61P 35/02*** | (2006.01) |
| ***C07K 14/705*** | (2006.01) |
| ***C07K 16/28*** | (2006.01) |
| ***C12N 5/0783*** | (2010.01) |
| ***C12N 15/86*** | (2006.01) |

(52) U.S. Cl.

CPC .......... *C07K 14/7051* (2013.01); *A61K 40/11* (2025.01); *A61K 40/31* (2025.01); *A61K 40/4214* (2025.01); *A61K 40/4217* (2025.01); *A61K 40/4221* (2025.01); *A61P 35/02* (2018.01); *C07K 14/70596* (2013.01); *C12N 5/0638* (2013.01); *C12N 15/86* (2013.01); *A61K 2239/23* (2023.05); *A61K 2239/31* (2023.05); *A61K 2239/38* (2023.05); *A61K 2239/48* (2023.05); *C07K 16/2866* (2013.01); *C07K 2317/622* (2013.01); *C07K 2319/03* (2013.01); *C07K 2319/33* (2013.01); *C12N 2502/30* (2013.01); *C12N 2510/00* (2013.01); *C12N 2740/13043* (2013.01); *C12N 2740/16044* (2013.01); *C12N 2840/20* (2013.01)

(58) Field of Classification Search

CPC .......... C07K 14/7051; C07K 14/70596; A61P 35/02; A61K 40/4217; A61K 40/4214; A61K 40/4221; A61K 40/31; A61K 40/11; C12N 5/0638; C12N 15/86

See application file for complete search history.

(56) References Cited

U.S. PATENT DOCUMENTS

| | | | |
|---|---|---|---|
| 8,163,279 | B2 | 4/2012 | Bergstein |
| 9,657,105 | B2 | 5/2017 | Forman et al. |
| 9,815,901 | B2 | 11/2017 | Brogdon et al. |
| 9,944,709 | B2 | 4/2018 | Galetto |
| 2014/0322212 | A1 | 10/2014 | Brogdon et al. |

FOREIGN PATENT DOCUMENTS

| | | | |
|---|---|---|---|
| WO | WO2014138306 | A1 * | 9/2014 |
| WO | 2016028896 | A1 | 2/2016 |
| WO | 2017075147 | A1 | 5/2017 |
| WO | 2018231759 | A1 | 12/2018 |

OTHER PUBLICATIONS

Communication (International Search Report) issued by the International Searching Authority in International Application No. PCT/US20/27719 dated Sep. 4, 2020, 6 pages total.

Communication (Written Opinion) issued by the International Searching Authority in International Application No. PCT/US20/27719 dated Sep. 4, 2020, 7 pages total.

Straathof, KC, et al.; "Suicide genes as safety switches in T lymphocytes", Cyrotherapy (2003) vol. 5, No. 3, DOI: 10.1080/14653240310001497, pp. 227-230.

Griffioen, Marieke, et al.; "Retroviral transfer of human CD20 as a suicide gene for adoptive T-cell therapy", haematologica 2009; 94(9), pp. 1316-1320.

(Continued)

*Primary Examiner* — Kodye Lee Abbott

(74) *Attorney, Agent, or Firm* — Troutman Pepper Locke LLP

(57) ABSTRACT

The present disclosure provides chimeric antigen receptors (CARs), particularly CARs that have enhanced antitumor properties and/or can be regulated by safety switches. Also provided are polypeptides of the CARs and other related molecules, polynucleotides, vectors, and cell compositions comprising the same. Pharmaceutical compositions comprising the polypeptides, polynucleotides, vectors, or cells of the present disclosure, and their uses in treating a cancer in a subject are also provided.

15 Claims, 30 Drawing Sheets

Specification includes a Sequence Listing.

(56) References Cited

OTHER PUBLICATIONS

Van Loenen, MM, et al.; "Multi-cistronic vector encoding optimized safety switch for adoptive therapy with T-cell receptor-modified T cells", Gene Therapy (2013) 20, www.nature.com/gt, pp. 861-867.

Philip, Brian, et al.; "A highly compact epitope-based marker/suicide gene for easier and safer T-cell therapy" Blood, Aug. 21, 2014, vol. 124, No. 8, DOI 10.1182/blood-2014-01-545020, pp. 1277-1287.

Bonifant, Challice L., et al., "CD123-Engager T Cell as a Novel Immunotherapeutic for Acute Myeloid Leukemia", The American Society of Gene & Cell Therapy, Jun. 1, 2016; DOI 10.1038/mt2016.116, 12 pages total.

Bonifant, Challice L., et al.; Supplemental Figures 1-7 for "CD123-Engager T Cell as a Novel Immunotherapeutic for Acute Myeloid Leukemia", The American Society of Gene & Cell Therapy, Jun. 1, 2016; DOI 10.1038/mt2016.116, 7 pages total.

* cited by examiner

CD20 | T2A | SP | 292 ScFv | CD8α H | CD8α TM | 41BB | Z

FIG. 3A

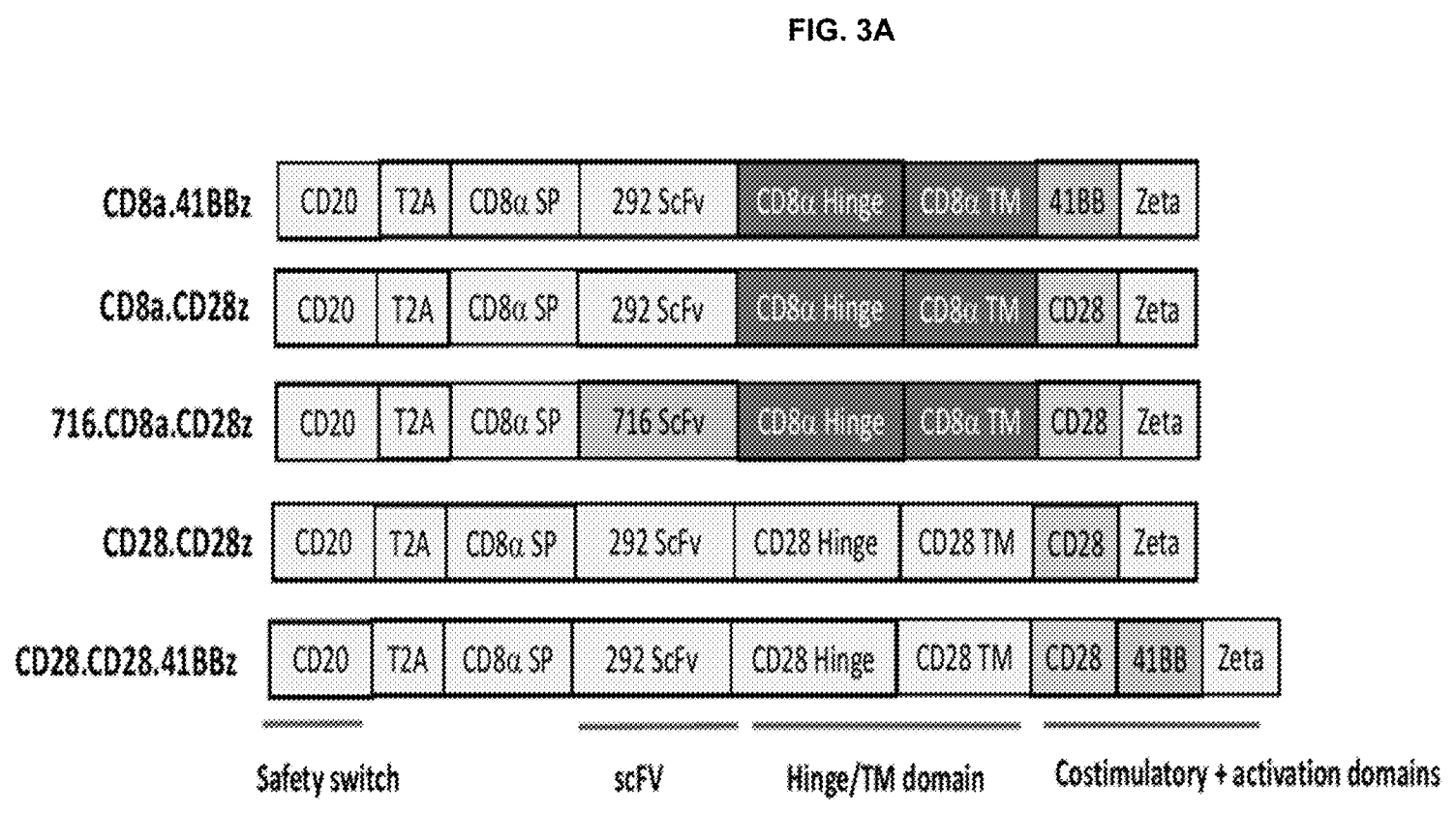

CD8a.41BBz
CD20 | T2A | CD8α SP | 292 ScFv | CD8α Hinge | CD8α TM | 41BB | Zeta

CD8a.CD28z
CD20 | T2A | CD8α SP | 292 ScFv | CD8α Hinge | CD8α TM | CD28 | Zeta

716.CD8a.CD28z
CD20 | T2A | CD8α SP | 716 ScFv | CD8α Hinge | CD8α TM | CD28 | Zeta CD28.CD28z
CD20 | T2A | CD8α SP | 292 ScFv | CD28 Hinge | CD28 TM | CD28 | Zeta CD28.CD28.41BBz
CD20 | T2A | CD8α SP | 292 ScFv | CD28 Hinge | CD28 TM | CD28 | 41BB | Zeta Safety switch
scFV
Hinge/TM domain
Costimulatory + activation domains NT
8.41BBz
8.28z
716.8.28z
28.28z
28.28.41BBz
0.17
0.24
89.1
0.52
0.46
86.0
6.92
6.61
0.56
75.6
12.9
11.0
0.39
86.3
8.09
5.19
0.60
86.8
7.15
5.44
0.74
85.5
6.65
7.12
Comp-FL2-A :: CAR PE-A
Comp-FL1-A :: CD20 FITC-A
CD20
CD123-CAR

NS

% Expression 100
80
60
40
20
0

TIM3

NT
8.41BBz
8.28z
716.8.28z
28.28z
28.28.41BBz

| Wilcoxon rank sum P-values for pairwise comparisons | | | | | |
|---|---|---|---|---|---|
| | NT | 8.28z | 28.28.41BBz | 28.28z | 716.8.28z |
| 8.28z | 0.0099 | | | | |
| 28.28.41BBz | 0.0099 | 0.2896 | | | |
| 28.28z | 0.0104 | 0.5023 | 0.7337 | | |
| 716.8.28z | 0.0099 | 1.0000 | 0.2896 | 0.5023 | |
| 8.41BBz | 0.0109 | 0.9142 | 0.3290 | 0.4521 | 1.0000 |

| Wilcoxon rank sum P-values for pairwise comparisons | | | | | |
|---|---|---|---|---|---|
| | Tumor Only | 8.28z | 28.28.41BBz | 28.28z | 716.8.28z |
| 8.28z | 0.0117 | | | | |
| 28.28.41BBz | 0.0117 | 0.2418 | | | |
| 28.28z | 0.0109 | 0.1931 | 0.3917 | | |
| 716.8.28z | 0.0107 | 0.0181 | 0.1475 | 0.0170 | |
| 8.41BBz | 0.0117 | 0.1138 | 0.3961 | 0.3932 | 0.0181 |

SEQUENCE LISTING

```
<160> NUMBER OF SEQ ID NOS: 85

<210> SEQ ID NO 1
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Thr Phe Thr Ser Tyr Trp Met Asn Trp Val Lys Gln Arg Pro Asp Gln
    50                  55                  60

Gly Leu Glu Trp Ile Gly Arg Ile Asp Pro Tyr Asp Ser Glu Thr His
65                  70                  75                  80

Tyr Asn Gln Lys Phe Lys Asp Lys Ala Ile Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Gly Asn Trp Asp Asp Tyr Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Val Gln Ile Thr Gln Ser Pro Ser
145                 150                 155                 160
```

```
Tyr Leu Ala Ala Ser Pro Gly Glu Thr Ile Thr Ile Asn Cys Arg Ala
                165                 170                 175

Ser Lys Ser Ile Ser Lys Asp Leu Ala Trp Tyr Gln Glu Lys Pro Gly
            180                 185                 190

Lys Thr Asn Lys Leu Leu Ile Tyr Ser Gly Ser Thr Leu Gln Ser Gly
        195                 200                 205

Ile Pro Ser Arg Phe Ser Gly Ser Gly Ser Gly Thr Asp Phe Thr Leu
    210                 215                 220

Thr Ile Ser Ser Leu Glu Pro Glu Asp Phe Ala Met Tyr Tyr Cys Gln
225                 230                 235                 240

Gln His Asn Lys Tyr Pro Tyr Thr Phe Gly Gly Gly Thr Lys Leu Glu
                245                 250                 255

Ile Lys Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg


<210> SEQ ID NO 2
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

atggccttac cagtgaccgc cttgctcctg ccgctggcct tgctgctcca cgccgccagg      60

ccgcaggtgc agctgcagca gcctggcgct gaactcgtgc ggccaggcgc ttctgtgaag     120

ctgagctgta aagccagcgg ctacaccttc accagctact ggatgaactg ggtcaagcag     180
```

```
cggcccgacc agggcctgga atggatcgga agaatcgacc cctacgacag cgagacacac    240

tacaaccaga agttcaagga caaggccatc ctgaccgtgg acaagagcag cagcaccgcc    300

tacatgcagc tgtccagcct gaccagcgag gacagcgccg tgtactactg cgccagaggc    360

aactgggacg actactgggg ccagggcaca accctgacag tgtctagcgg aggcggagga    420

tcaggcggcg gaggaagtgg gggaggcgga tctgatgtgc agattaccca gtcccccagc    480

tacctggccg cctctcctgg cgagacaatc accatcaact gccgggccag caagagcatc    540

tccaaggacc tggcctggta tcaggaaaag cccggcaaga ccaacaagct gctgatctac    600

agcggctcca ccctgcagtc cggcatcccc agcagatttt ccggcagcgg ctctggcacc    660

gacttcaccc tgaccatcag ctccctggaa cccgaggact ttgccatgta ctattgccag    720

cagcacaaca agtaccctta caccttcggc ggaggcacca agctggaaat caagagcacc    780

acgacgccag cgccgcgacc accaacgccg gcgcccacca tcgcgtcgca gcccctgtcc    840

ctgcgcccag aggcgtgccg gccagcggcg gggggcgcag tgcacacgag ggggctggac    900

ttcgcctgtg atatctacat ctgggcgccc ttggccggga cttgtggggt ccttctcctg    960

tcactggtta tcacccttta ctgcaaacgg ggcagaaaga aactcctgta tatattcaaa   1020

caaccattta tgagaccagt acaaactact caagaggaag atggctgtag ctgccgattt   1080

ccagaagaag aagaaggagg atgtgaactg agagtgaagt tcagcaggag cgcagacgcc   1140

cccgcgtacc agcagggcca gaaccagctc tataacgagc tcaatctagg acgaagagag   1200

gagtacgatg ttttggacaa gagacgtggc cgggaccctg agatgggggg aaagccgaga   1260

aggaagaacc ctcaggaagg cctgtacaat gaactgcaga aagataagat ggcggaggcc   1320

tacagtgaga ttgggatgaa aggcgagcgc cggaggggca aggggcacga tggcctttac   1380

cagggtctca gtacagccac caaggacacc tacgacgccc ttcacatgca ggccctgccc   1440

cctcgctaa                                                           1449


<210> SEQ ID NO 3
<211> LENGTH: 481
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Thr Phe Thr Ser Tyr Trp Met Asn Trp Val Lys Gln Arg Pro Asp Gln
    50                  55                  60

Gly Leu Glu Trp Ile Gly Arg Ile Asp Pro Tyr Asp Ser Glu Thr His
65                  70                  75                  80

Tyr Asn Gln Lys Phe Lys Asp Lys Ala Ile Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Gly Asn Trp Asp Asp Tyr Trp Gly Gln
        115                 120                 125
```

```
Gly Thr Thr Leu Thr Val Ser Ser Gly Gly Gly Gly Ser Gly Gly Gly
    130                 135                 140

Gly Ser Gly Gly Gly Gly Ser Asp Val Gln Ile Thr Gln Ser Pro Ser
145                 150                 155                 160

Tyr Leu Ala Ala Ser Pro Gly Glu Thr Ile Thr Ile Asn Cys Arg Ala
                165                 170                 175

Ser Lys Ser Ile Ser Lys Asp Leu Ala Trp Tyr Gln Glu Lys Pro Gly
            180                 185                 190

Lys Thr Asn Lys Leu Leu Ile Tyr Ser Gly Ser Thr Leu Gln Ser Gly
        195                 200                 205

Ile Pro Ser Arg Phe Ser Gly Ser Gly Ser Gly Thr Asp Phe Thr Leu
    210                 215                 220

Thr Ile Ser Ser Leu Glu Pro Glu Asp Phe Ala Met Tyr Tyr Cys Gln
225                 230                 235                 240

Gln His Asn Lys Tyr Pro Tyr Thr Phe Gly Gly Gly Thr Lys Leu Glu
                245                 250                 255

Ile Lys Ser Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Arg Ser Lys Arg Ser Arg Leu Leu
                325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
        355                 360                 365

Ser Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg
```

<210> SEQ ID NO 4
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

```
atggccttac cagtgaccgc cttgctcctg ccgctggcct tgctgctcca cgccgccagg      60

ccgcaggtgc agctgcagca gcctggcgct gaactcgtgc ggccaggcgc ttctgtgaag     120

ctgagctgta aagccagcgg ctacaccttc accagctact ggatgaactg ggtcaagcag     180

cggcccgacc agggcctgga atggatcgga agaatcgacc cctacgacag cgagacacac     240

tacaaccaga agttcaagga caaggccatc ctgaccgtgg acaagagcag cagcaccgcc     300

tacatgcagc tgtccagcct gaccagcgag gacagcgccg tgtactactg cgccagaggc     360

aactgggacg actactgggg ccagggcaca accctgacag tgtctagcgg aggcggagga     420

tcaggcggcg gaggaagtgg gggaggcgga tctgatgtgc agattaccca gtcccccagc     480

tacctggccg cctctcctgg cgagacaatc accatcaact gccgggccag caagagcatc     540

tccaaggacc tggcctggta tcaggaaaag cccggcaaga ccaacaagct gctgatctac     600

agcggctcca ccctgcagtc cggcatcccc agcagatttt ccggcagcgg ctctggcacc     660

gacttcaccc tgaccatcag ctccctggaa cccgaggact ttgccatgta ctattgccag     720

cagcacaaca agtaccctta caccttcggc ggaggcacca agctggaaat caagagcacc     780

acgacgccag cgccgcgacc accaacgccg gcgcccacca tcgcgtcgca gcccctgtcc     840

ctgcgcccag aggcgtgccg gccagcggcg gggggcgcag tgcacacgag ggggctggac     900

ttcgcctgtg atatctacat ctgggcgccc ttggccggga cttgtggggt ccttctcctg     960

tcactggtta tcacccttta ctgccgaagc aagcggagcc ggctgctgca cagcgactac    1020

atgaacatga cccctagacg gcccggacca accagaaagc actaccagcc ttacgctcct    1080

cctagagatt tcgccgccta ccggtccaga gtgaagttca gcaggagcgc agacgccccc    1140

gcgtaccagc agggccagaa ccagctctat aacgagctca atctaggacg aagagaggag    1200

tacgatgttt tggacaagag acgtggccgg gaccctgaga tggggggaaa gccgagaagg    1260

aagaaccctc aggaaggcct gtacaatgaa ctgcagaaag ataagatggc ggaggcctac    1320

agtgagattg ggatgaaagg cgagcgccgg aggggcaagg ggcacgatgg cctttaccag    1380

ggtctcagta cagccaccaa ggacacctac gacgcccttc acatgcaggc cctgccccct    1440

cgctaa                                                               1446
```

<210> SEQ ID NO 5
<211> LENGTH: 520
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Thr Phe Thr Ser Tyr Trp Met Asn Trp Val Lys Gln Arg Pro Asp Gln
    50                  55                  60

Gly Leu Glu Trp Ile Gly Arg Ile Asp Pro Tyr Asp Ser Glu Thr His
65                  70                  75                  80

Tyr Asn Gln Lys Phe Lys Asp Lys Ala Ile Leu Thr Val Asp Lys Ser
                85                  90                  95
```

-continued

```
Ser Ser Thr Ala Tyr Met Gln Leu Ser Ser Leu Thr Ser Glu Asp Ser
            100                 105                 110

Ala Val Tyr Tyr Cys Ala Arg Gly Asn Trp Asp Asp Tyr Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Val Gln Ile Thr Gln Ser Pro Ser
145                 150                 155                 160

Tyr Leu Ala Ala Ser Pro Gly Glu Thr Ile Thr Ile Asn Cys Arg Ala
                165                 170                 175

Ser Lys Ser Ile Ser Lys Asp Leu Ala Trp Tyr Gln Glu Lys Pro Gly
            180                 185                 190

Lys Thr Asn Lys Leu Leu Ile Tyr Ser Gly Ser Thr Leu Gln Ser Gly
        195                 200                 205

Ile Pro Ser Arg Phe Ser Gly Ser Gly Ser Gly Thr Asp Phe Thr Leu
    210                 215                 220

Thr Ile Ser Ser Leu Glu Pro Glu Asp Phe Ala Met Tyr Tyr Cys Gln
225                 230                 235                 240

Gln His Asn Lys Tyr Pro Tyr Thr Phe Gly Gly Gly Thr Lys Leu Glu
                245                 250                 255

Ile Lys Ser Ile Glu Val Met Tyr Pro Pro Pro Tyr Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Lys Arg
        355                 360                 365

Gly Arg Lys Lys Leu Leu Tyr Ile Phe Lys Gln Pro Phe Met Arg Pro
    370                 375                 380

Val Gln Thr Thr Gln Glu Glu Asp Gly Cys Ser Cys Arg Phe Pro Glu
385                 390                 395                 400

Glu Glu Glu Gly Gly Cys Glu Leu Arg Val Lys Phe Ser Arg Ser Ala
                405                 410                 415

Asp Ala Pro Ala Tyr Gln Gln Gly Gln Asn Gln Leu Tyr Asn Glu Leu
            420                 425                 430

Asn Leu Gly Arg Arg Glu Glu Tyr Asp Val Leu Asp Lys Arg Arg Gly
        435                 440                 445

Arg Asp Pro Glu Met Gly Gly Lys Pro Arg Arg Lys Asn Pro Gln Glu
    450                 455                 460

Gly Leu Tyr Asn Glu Leu Gln Lys Asp Lys Met Ala Glu Ala Tyr Ser
465                 470                 475                 480

Glu Ile Gly Met Lys Gly Glu Arg Arg Arg Gly Lys Gly His Asp Gly
                485                 490                 495

Leu Tyr Gln Gly Leu Ser Thr Ala Thr Lys Asp Thr Tyr Asp Ala Leu
            500                 505                 510

His Met Gln Ala Leu Pro Pro Arg
```

515 520

<210> SEQ ID NO 6
<211> LENGTH: 1563
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6
atggccttac cagtgaccgc cttgctcctg ccgctggcct tgctgctcca cgccgccagg 60
ccgcaggtgc agctgcagca gcctggcgct gaactcgtgc ggccaggcgc ttctgtgaag 120
ctgagctgta aagccagcgg ctacaccttc accagctact ggatgaactg ggtcaagcag 180
cggcccgacc agggcctgga atggatcgga agaatcgacc cctacgacag cgagacacac 240
tacaaccaga agttcaagga caaggccatc ctgaccgtgg acaagagcag cagcaccgcc 300
tacatgcagc tgtccagcct gaccagcgag gacagcgccg tgtactactg cgccagaggc 360
aactgggacg actactgggg ccagggcaca accctgacag tgtctagcgg aggcggagga 420
tcaggcggcg gaggaagtgg gggaggcgga tctgatgtgc agattaccca gtcccccagc 480
tacctggccg cctctcctgg cgagacaatc accatcaact gccgggccag caagagcatc 540
tccaaggacc tggcctggta tcaggaaaag cccggcaaga ccaacaagct gctgatctac 600
agcggctcca ccctgcagtc cggcatcccc agcagatttt ccggcagcgg ctctggcacc 660
gacttcaccc tgaccatcag ctccctggaa cccgaggact ttgccatgta ctattgccag 720
cagcacaaca agtaccctta caccttcggc ggaggcacca agctggaaat caagagcatc 780
gaagtgatgt acccgcctcc ttacctggac aacgagaagt ccaacggcac catcatccac 840
gtgaagggaa agcacctgtg tccttctcca ctgttccccg gacctagcaa gcctttctgg 900
gtgctcgttg ttgttggcgg cgtgctggcc tgttacagcc tgctggttac cgtggccttc 960
atcatctttt gggtccgaag caagcggagc cggctgctgc acagcgacta catgaacatg 1020
acccctagac ggcccggacc aaccagaaag cactaccagc cttacgctcc tcctagagat 1080
ttcgccgcct accggtccaa acggggcaga aagaaactcc tgtatatatt caaacaacca 1140
tttatgagac cagtacaaac tactcaagag gaagatggct gtagctgccg atttccagaa 1200
gaagaagaag gaggatgtga actgagagtg aagttcagca ggagcgcaga cgcccccgcg 1260
taccagcagg gccagaacca gctctataac gagctcaatc taggacgaag agaggagtac 1320
gatgttttgg acaagagacg tggccgggac cctgagatgg ggggaaagcc gagaaggaag 1380
aaccctcagg aaggcctgta caatgaactg cagaaagata agatggcgga ggcctacagt 1440
gagattggga tgaaaggcga gcgccggagg ggcaaggggc acgatggcct ttaccagggt 1500
ctcagtacag ccaccaagga cacctacgac gcccttcaca tgcaggccct gccccctcgc 1560
taa 1563

<210> SEQ ID NO 7
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

Met Ala Leu Pro Val Thr Ala Leu Leu Leu Pro Leu Ala Leu Leu Leu

-continued

```
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Thr Phe Thr Ser Tyr Trp Met Asn Trp Val Lys Gln Arg Pro Asp Gln
    50                  55                  60

Gly Leu Glu Trp Ile Gly Arg Ile Asp Pro Tyr Asp Ser Glu Thr His
65                  70                  75                  80

Tyr Asn Gln Lys Phe Lys Asp Lys Ala Ile Leu Thr Val Asp Lys Ser
                85                  90                  95

Ser Ser Thr Ala Tyr Met Gln Leu Ser Ser Leu Thr Ser Glu Asp Ser
            100                 105                 110

Ala Val Tyr Tyr Cys Ala Arg Gly Asn Trp Asp Asp Tyr Trp Gly Gln
        115                 120                 125

Gly Thr Thr Leu Thr Val Ser Ser Gly Gly Gly Gly Ser Gly Gly Gly
    130                 135                 140

Gly Ser Gly Gly Gly Gly Ser Asp Val Gln Ile Thr Gln Ser Pro Ser
145                 150                 155                 160

Tyr Leu Ala Ala Ser Pro Gly Glu Thr Ile Thr Ile Asn Cys Arg Ala
                165                 170                 175

Ser Lys Ser Ile Ser Lys Asp Leu Ala Trp Tyr Gln Glu Lys Pro Gly
            180                 185                 190

Lys Thr Asn Lys Leu Leu Ile Tyr Ser Gly Ser Thr Leu Gln Ser Gly
        195                 200                 205

Ile Pro Ser Arg Phe Ser Gly Ser Gly Ser Gly Thr Asp Phe Thr Leu
    210                 215                 220

Thr Ile Ser Ser Leu Glu Pro Glu Asp Phe Ala Met Tyr Tyr Cys Gln
225                 230                 235                 240

Gln His Asn Lys Tyr Pro Tyr Thr Phe Gly Gly Gly Thr Lys Leu Glu
                245                 250                 255

Ile Lys Ser Ile Glu Val Met Tyr Pro Pro Pro Tyr Leu Asp Asn Glu
            260                 265                 270

Lys Ser Asn Gly Thr Ile Ile His Val Lys Gly Lys His Leu Cys Pro
        275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430
```

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 8
<211> LENGTH: 1437
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 8
atggccttac cagtgaccgc cttgctcctg ccgctggcct tgctgctcca cgccgccagg 60
ccgcaggtgc agctgcagca gcctggcgct gaactcgtgc ggccaggcgc ttctgtgaag 120
ctgagctgta aagccagcgg ctacaccttc accagctact ggatgaactg ggtcaagcag 180
cggcccgacc agggcctgga atggatcgga agaatcgacc cctacgacag cgagacacac 240
tacaaccaga agttcaagga caaggccatc ctgaccgtgg acaagagcag cagcaccgcc 300
tacatgcagc tgtccagcct gaccagcgag gacagcgccg tgtactactg cgccagaggc 360
aactgggacg actactgggg ccagggcaca accctgacag tgtctagcgg aggcggagga 420
tcaggcggcg gaggaagtgg gggaggcgga tctgatgtgc agattaccca gtcccccagc 480
tacctggccg cctctcctgg cgagacaatc accatcaact gccgggccag caagagcatc 540
tccaaggacc tggcctggta tcaggaaaag cccggcaaga ccaacaagct gctgatctac 600
agcggctcca ccctgcagtc cggcatcccc agcagatttt ccggcagcgg ctctggcacc 660
gacttcaccc tgaccatcag ctccctggaa cccgaggact ttgccatgta ctattgccag 720
cagcacaaca agtaccctta caccttcggc ggaggcacca agctggaaat caagagcatc 780
gaagtgatgt acccgcctcc ttacctggac aacgagaagt ccaacggcac catcatccac 840
gtgaagggaa agcacctgtg tccttctcca ctgttccccg gacctagcaa gcctttctgg 900
gtgctcgttg ttgttggcgg cgtgctggcc tgttacagcc tgctggttac cgtggccttc 960
atcatctttt gggtccgaag caagcggagc cggctgctgc acagcgacta catgaacatg 1020
acccctagac ggcccggacc aaccagaaag cactaccagc cttacgctcc tcctagagat 1080
ttcgccgcct accggtccag agtgaagttc agcaggagcg cagacgcccc cgcgtaccag 1140
cagggccaga accagctcta taacgagctc aatctaggac gaagagagga gtacgatgtt 1200
ttggacaaga gacgtggccg ggaccctgag atggggggaa agccgagaag gaagaaccct 1260
caggaaggcc tgtacaatga actgcagaaa gataagatgg cggaggccta cagtgagatt 1320
gggatgaaag gcgagcgccg gaggggcaag gggcacgatg gcctttacca gggtctcagt 1380
acagccacca aggacaccta cgacgccctt cacatgcagg ccctgccccc tcgctaa 1437

<210> SEQ ID NO 9
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 9

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
    50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

Ala Ser Asn Leu Glu Ser Gly Ile Pro Ala Arg Phe Ser Gly Ser Gly
    210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415
```

```
Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485


<210> SEQ ID NO 10
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

atggccttac cagtgaccgc cttgctcctg ccgctggcct tgctgctcca cgccgccagg     60

ccgcagattc agctggtgca gtctggcccc gagctgaaga aacccggcga gacagtgaag    120

atcagctgca aggccagcgg ctacatcttc accaactacg gcatgaactg ggtcaagcag    180

gcccctggca agagcttcaa gtggatgggc tggatcaaca cctacaccgg cgagagcacc    240

tacagcgccg acttcaaggg cagattcgcc ttcagcctgg aaaccagcgc cagcaccgcc    300

tacctgcaca tcaacgacct gaagaacgag gacaccgcca cctacttttg cgccagaagc    360

ggcggctacg accctatgga ttattggggc cagggcacca gcgtgaccgt gtctagcgga    420

ggcggaggaa gtggcggcgg aggatctggg ggaggcggat ctgatatcgt gctgacccag    480

agccctgcca gcctggctgt gtctctggga cagagagcca ccatcagctg tcgggccagc    540

gagagcgtgg acaattacgg caacaccttc atgcactggt atcagcagaa gcccggccag    600

ccccccaagc tgctgatcta cagagccagc aacctggaaa gcggcatccc cgccagattt    660

tccggcagcg gcagcagaac cgacttcacc ctgaccatca accccgtgga agccgacgac    720

gtggccacct attactgcca gcagagcaac gaggaccccc ctacctttgg agccggcacc    780

aagctggaac tgaagaccac gacgccagcg ccgcgaccac caacgccggc gcccaccatc    840

gcgtcgcagc ccctgtccct gcgcccagag gcgtgccggc cagcggcggg gggcgcagtg    900

cacacgaggg ggctggactt cgcctgtgat atctacatct gggcgccctt ggccgggact    960

tgtggggtcc ttctcctgtc actggttatc accctttact gccggtccaa gagaagcaga   1020

ctgctgcaca gcgactacat gaacatgacc cctagacggc ccggacctac cagaaagcac   1080

taccagcctt acgctcctcc tagagatttc gccgcctacc ggtccagagt gaagttcagc   1140

aggagcgcag acgcccccgc gtaccagcag ggccagaacc agctctataa cgagctcaat   1200

ctaggacgaa gagaggagta cgatgttttg gacaagagac gtggccggga ccctgagatg   1260

gggggaaagc cgagaaggaa gaaccctcag gaaggcctgt acaatgaact gcagaaagat   1320

aagatggcgg aggcctacag tgagattggg atgaaaggcg agcgccggag gggcaagggg   1380

cacgatggcc tttaccaggg tctcagtaca gccaccaagg acacctacga cgcccttcac   1440

atgcaggccc tgccccctcg ctaa                                          1464


<210> SEQ ID NO 11
<211> LENGTH: 472
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
    130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Asp Leu Glu Pro Lys
            260                 265                 270

Ser Cys Asp Lys Thr His Thr Cys Pro Pro Cys Pro Asp Pro Lys Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380
```

```
Glu Glu Tyr Asp Val Leu Asp Lys Arg Arg Gly Arg Asp Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470


<210> SEQ ID NO 12
<211> LENGTH: 1416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

atggactgga tctggcgcat cctgtttctc gtgggagccg ccacaggcgc ccattctcag     60

gtgcagctgc agcagcctgg cgctgaactc gtgcggccag gcgcttctgt gaagctgagc    120

tgtaaagcca gcggctacac cttcagcaac tacctgatga actgggtcaa gcagcggccc    180

gagcaggacc tggattggat cggcagaatc gacccctacg acggcgacat cgactacaac    240

cagaacttca aggacaaggc catcctgacc gtggacaaga gcagcagcac cgcctacatg    300

cagctgtcca gcctgaccag cgaggacagc gccgtgtact actgcgccag aggctacggc    360

acagcctacg gcgtggacta ttggggccag ggcacaagcg tgaccgtgtc cagcgccaag    420

accacccccc ctaagctgga agagggcgag ttctccgagg cccgggtgga cattgtgctg    480

acacagtctc cagccagcct ggccgtgtcc ctgggacaga gagccaccat cagctgtagg    540

gccagcgaga gcgtggacaa ctacggcatc agcttcatga attggttcca gcagaagccc    600

ggccagcccc ccaagctgct gatctatgcc gccagcagac agggcagcgg agtgcctgcc    660

agattttctg gcagcggctc cggcaccgac ttcagcctga acatccaccc tatggaagag    720

gacgacaccg ccatgtactt ttgccagcag agcaaagagg tgccctggac ctttggcgga    780

ggcaccaagc tggaaatcaa ggatctcgag cccaaatctt gtgacaaaac tcacacatgc    840

ccaccgtgcc cggatcccaa attttgggtg ctggtggtgg ttggtggagt cctggcttgc    900

tatagcttgc tagtaacagt ggcctttatt attttctggg tgaggagtaa gaggagcagg    960

ctcctgcaca gtgactacat gaacatgact ccccgccgcc ccgggcccac ccgcaagcat   1020

taccagccct atgccccacc acgcgacttc gcagcctatc gctccagagt gaagttcagc   1080

aggagcgcag acgcccccgc gtaccagcag ggccagaacc agctctataa cgagctcaat   1140

ctaggacgaa gagaggagta cgatgttttg gacaagagac gtggccggga cagacgtggc   1200

cgggaccctg agatgggggg aaagccgaga aggaagaacc ctcaggaagg cctgtacaat   1260

gaactgcaga aagataagat ggcggaggcc tacagtgaga ttgggatgaa aggcgagcgc   1320

cggaggggca aggggcacga tggcctttac cagggtctca gtacagccac caaggacacc   1380

tacgacgccc ttcacatgca ggccctgccc cctcgc                              1416
```

<210> SEQ ID NO 13
<211> LENGTH: 801
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 13

```
Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro Ala Ser Arg Ala Glu Gly Arg
    290                 295                 300

Gly Ser Leu Leu Thr Cys Gly Asp Val Glu Glu Asn Pro Gly Pro Met
305                 310                 315                 320

Ala Leu Pro Val Thr Ala Leu Leu Leu Pro Leu Ala Leu Leu Leu His
                325                 330                 335

Ala Ala Arg Pro Gln Val Gln Leu Gln Gln Pro Gly Ala Glu Leu Val
            340                 345                 350

Arg Pro Gly Ala Ser Val Lys Leu Ser Cys Lys Ala Ser Gly Tyr Thr
        355                 360                 365
```

```
Phe Thr Ser Tyr Trp Met Asn Trp Val Lys Gln Arg Pro Asp Gln Gly
    370                 375                 380

Leu Glu Trp Ile Gly Arg Ile Asp Pro Tyr Asp Ser Glu Thr His Tyr
385                 390                 395                 400

Asn Gln Lys Phe Lys Asp Lys Ala Ile Leu Thr Val Asp Lys Ser Ser
                405                 410                 415

Ser Thr Ala Tyr Met Gln Leu Ser Ser Leu Thr Ser Glu Asp Ser Ala
            420                 425                 430

Val Tyr Tyr Cys Ala Arg Gly Asn Trp Asp Asp Tyr Trp Gly Gln Gly
        435                 440                 445

Thr Thr Leu Thr Val Ser Ser Gly Gly Gly Gly Ser Gly Gly Gly Gly
    450                 455                 460

Ser Gly Gly Gly Gly Ser Asp Val Gln Ile Thr Gln Ser Pro Ser Tyr
465                 470                 475                 480

Leu Ala Ala Ser Pro Gly Glu Thr Ile Thr Ile Asn Cys Arg Ala Ser
                485                 490                 495

Lys Ser Ile Ser Lys Asp Leu Ala Trp Tyr Gln Glu Lys Pro Gly Lys
            500                 505                 510

Thr Asn Lys Leu Leu Ile Tyr Ser Gly Ser Thr Leu Gln Ser Gly Ile
        515                 520                 525

Pro Ser Arg Phe Ser Gly Ser Gly Ser Gly Thr Asp Phe Thr Leu Thr
    530                 535                 540

Ile Ser Ser Leu Glu Pro Glu Asp Phe Ala Met Tyr Tyr Cys Gln Gln
545                 550                 555                 560

His Asn Lys Tyr Pro Tyr Thr Phe Gly Gly Gly Thr Lys Leu Glu Ile
                565                 570                 575

Lys Ser Thr Thr Thr Pro Ala Pro Arg Pro Pro Thr Pro Ala Pro Thr
            580                 585                 590

Ile Ala Ser Gln Pro Leu Ser Leu Arg Pro Glu Ala Cys Arg Pro Ala
        595                 600                 605

Ala Gly Gly Ala Val His Thr Arg Gly Leu Asp Phe Ala Cys Asp Ile
    610                 615                 620

Tyr Ile Trp Ala Pro Leu Ala Gly Thr Cys Gly Val Leu Leu Leu Ser
625                 630                 635                 640

Leu Val Ile Thr Leu Tyr Cys Lys Arg Gly Arg Lys Lys Leu Leu Tyr
                645                 650                 655

Ile Phe Lys Gln Pro Phe Met Arg Pro Val Gln Thr Thr Gln Glu Glu
            660                 665                 670

Asp Gly Cys Ser Cys Arg Phe Pro Glu Glu Glu Glu Gly Gly Cys Glu
        675                 680                 685

Leu Arg Val Lys Phe Ser Arg Ser Ala Asp Ala Pro Ala Tyr Gln Gln
    690                 695                 700

Gly Gln Asn Gln Leu Tyr Asn Glu Leu Asn Leu Gly Arg Arg Glu Glu
705                 710                 715                 720

Tyr Asp Val Leu Asp Lys Arg Arg Gly Arg Asp Pro Glu Met Gly Gly
                725                 730                 735

Lys Pro Arg Arg Lys Asn Pro Gln Glu Gly Leu Tyr Asn Glu Leu Gln
            740                 745                 750

Lys Asp Lys Met Ala Glu Ala Tyr Ser Glu Ile Gly Met Lys Gly Glu
        755                 760                 765

Arg Arg Arg Gly Lys Gly His Asp Gly Leu Tyr Gln Gly Leu Ser Thr
    770                 775                 780

Ala Thr Lys Asp Thr Tyr Asp Ala Leu His Met Gln Ala Leu Pro Pro
```

785 790 795 800

Arg

<210> SEQ ID NO 14
<211> LENGTH: 2406
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 14

```
atgaccacac ctcggaacag cgtgaacggc acatttcccg ccgagcctat gaagggccct     60

atcgccatgc agtctggccc caagcctctg ttcagacgga tgtctagcct cgtgggcccc    120

acacagagct tttcatgag agagagcaag accctgggcg ccgtgcagat catgaacggc     180

ctgtttcaca ttgccctcgg cggcctgctg atgatccctg ccggaatcta tgcccctatc    240

tgcgtgaccg tgtggtatcc tctgtggggc ggcatcatgt acatcatctc tggatctctg    300

ctggccgcca ccgagaagaa cagcagaaag tgtctggtca agggcaagat gatcatgaat    360

agcctgagcc tgttcgccgc catcagcggc atgatcctga gcatcatgga tatcctgaat    420

atcaagatca gccacttcct gaagatggaa agcctgaact tcatcagggc ccacacacct    480

tacatcaaca tctacaactg cgagcccgcc aatcctagcg agaagaatag ccccagcaca    540

cagtactgct actctatcca gagcctgttt ctgggcatcc tgagcgtgat gctgatcttc    600

gcattcttcc aagagctggt tatcgccggc atcgtggaaa acgagtggaa gcggacctgc    660

agcagaccca agagcaacat cgtgctgctg agcgccgagg aaaagaaaga gcagaccatc    720

gagatcaaag aggaagtcgt cggcctgacc gagacaagca gccagcctaa gaacgaagag    780

gacattgaga tcatccccat ccaagaagag gaagaagaag agactgagac aaacttcccc    840

gagcctcctc aggaccaaga gagcagcccc attgagaacg atagcagccc tgcctccaga    900

gccgaaggca gaggatcact gctgacatgc ggcgacgtgg aagagaaccc tggacccatg    960

gccttaccag tgaccgcctt gctcctgccg ctggccttgc tgctccacgc cgccaggccg   1020

caggtgcagc tgcagcagcc tggcgctgaa ctcgtgcggc caggcgcttc tgtgaagctg   1080

agctgtaaag ccagcggcta caccttcacc agctactgga tgaactgggt caagcagcgg   1140

cccgaccagg gcctggaatg gatcggaaga atcgacccct acgacagcga gacacactac   1200

aaccagaagt tcaaggacaa ggccatcctg accgtggaca agagcagcag caccgcctac   1260

atgcagctgt ccagcctgac cagcgaggac agcgccgtgt actactgcgc cagaggcaac   1320

tgggacgact actggggcca gggcacaacc ctgacagtgt ctagcggagg cggaggatca   1380

ggcggcggag gaagtggggg aggcggatct gatgtgcaga ttacccagtc ccccagctac   1440

ctggccgcct ctcctggcga gacaatcacc atcaactgcc gggccagcaa gagcatctcc   1500

aaggacctgg cctggtatca ggaaaagccc ggcaagacca acaagctgct gatctacagc   1560

ggctccaccc tgcagtccgg catccccagc agattttccg gcagcggctc tggcaccgac   1620

ttcaccctga ccatcagctc cctggaaccc gaggactttg ccatgtacta ttgccagcag   1680

cacaacaagt acccttacac cttcggcgga ggcaccaagc tggaaatcaa gagcaccacg   1740

acgccagcgc cgcgaccacc aacgccggcg cccaccatcg cgtcgcagcc cctgtccctg   1800

cgcccagagg cgtgccggcc agcggcgggg ggcgcagtgc acacgagggg gctggacttc   1860

gcctgtgata tctacatctg ggcgcccttg gccgggactt gtggggtcct tctcctgtca   1920
```

```
ctggttatca ccctttactg caaacggggc agaaagaaac tcctgtatat attcaaacaa   1980

ccatttatga gaccagtaca aactactcaa gaggaagatg gctgtagctg ccgatttcca   2040

gaagaagaag aaggaggatg tgaactgaga gtgaagttca gcaggagcgc agacgccccc   2100

gcgtaccagc agggccagaa ccagctctat aacgagctca atctaggacg aagagaggag   2160

tacgatgttt tggacaagag acgtggccgg gaccctgaga tggggggaaa gccgagaagg   2220

aagaaccctc aggaaggcct gtacaatgaa ctgcagaaag ataagatggc ggaggcctac   2280

agtgagattg ggatgaaagg cgagcgccgg aggggcaagg ggcacgatgg cctttaccag   2340

ggtctcagta cagccaccaa ggacacctac gacgcccttc acatgcaggc cctgccccct   2400

cgctaa                                                              2406


<210> SEQ ID NO 15
<211> LENGTH: 800
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270
```

-continued

```
Glu Glu Thr Glu Thr Asn Phe Pro Glu Pro Pro Gln Asp Gln Glu Ser
        275                 280                 285

Ser Pro Ile Glu Asn Asp Ser Ser Pro Ala Ser Arg Ala Glu Gly Arg
    290                 295                 300

Gly Ser Leu Leu Thr Cys Gly Asp Val Glu Glu Asn Pro Gly Pro Met
305                 310                 315                 320

Ala Leu Pro Val Thr Ala Leu Leu Leu Pro Leu Ala Leu Leu Leu His
                325                 330                 335

Ala Ala Arg Pro Gln Val Gln Leu Gln Gln Pro Gly Ala Glu Leu Val
            340                 345                 350

Arg Pro Gly Ala Ser Val Lys Leu Ser Cys Lys Ala Ser Gly Tyr Thr
        355                 360                 365

Phe Thr Ser Tyr Trp Met Asn Trp Val Lys Gln Arg Pro Asp Gln Gly
    370                 375                 380

Leu Glu Trp Ile Gly Arg Ile Asp Pro Tyr Asp Ser Glu Thr His Tyr
385                 390                 395                 400

Asn Gln Lys Phe Lys Asp Lys Ala Ile Leu Thr Val Asp Lys Ser Ser
                405                 410                 415

Ser Thr Ala Tyr Met Gln Leu Ser Ser Leu Thr Ser Glu Asp Ser Ala
            420                 425                 430

Val Tyr Tyr Cys Ala Arg Gly Asn Trp Asp Asp Tyr Trp Gly Gln Gly
        435                 440                 445

Thr Thr Leu Thr Val Ser Ser Gly Gly Gly Gly Ser Gly Gly Gly Gly
    450                 455                 460

Ser Gly Gly Gly Gly Ser Asp Val Gln Ile Thr Gln Ser Pro Ser Tyr
465                 470                 475                 480

Leu Ala Ala Ser Pro Gly Glu Thr Ile Thr Ile Asn Cys Arg Ala Ser
                485                 490                 495

Lys Ser Ile Ser Lys Asp Leu Ala Trp Tyr Gln Glu Lys Pro Gly Lys
            500                 505                 510

Thr Asn Lys Leu Leu Ile Tyr Ser Gly Ser Thr Leu Gln Ser Gly Ile
        515                 520                 525

Pro Ser Arg Phe Ser Gly Ser Gly Ser Gly Thr Asp Phe Thr Leu Thr
    530                 535                 540

Ile Ser Ser Leu Glu Pro Glu Asp Phe Ala Met Tyr Tyr Cys Gln Gln
545                 550                 555                 560

His Asn Lys Tyr Pro Tyr Thr Phe Gly Gly Gly Thr Lys Leu Glu Ile
                565                 570                 575

Lys Ser Thr Thr Thr Pro Ala Pro Arg Pro Pro Thr Pro Ala Pro Thr
            580                 585                 590

Ile Ala Ser Gln Pro Leu Ser Leu Arg Pro Glu Ala Cys Arg Pro Ala
        595                 600                 605

Ala Gly Gly Ala Val His Thr Arg Gly Leu Asp Phe Ala Cys Asp Ile
    610                 615                 620

Tyr Ile Trp Ala Pro Leu Ala Gly Thr Cys Gly Val Leu Leu Leu Ser
625                 630                 635                 640

Leu Val Ile Thr Leu Tyr Cys Arg Ser Lys Arg Ser Arg Leu Leu His
                645                 650                 655

Ser Asp Tyr Met Asn Met Thr Pro Arg Arg Pro Gly Pro Thr Arg Lys
            660                 665                 670

His Tyr Gln Pro Tyr Ala Pro Pro Arg Asp Phe Ala Ala Tyr Arg Ser
        675                 680                 685
```

```
Arg Val Lys Phe Ser Arg Ser Ala Asp Ala Pro Ala Tyr Gln Gln Gly
    690                 695                 700

Gln Asn Gln Leu Tyr Asn Glu Leu Asn Leu Gly Arg Arg Glu Glu Tyr
705                 710                 715                 720

Asp Val Leu Asp Lys Arg Arg Gly Arg Asp Pro Glu Met Gly Gly Lys
                725                 730                 735

Pro Arg Arg Lys Asn Pro Gln Glu Gly Leu Tyr Asn Glu Leu Gln Lys
            740                 745                 750

Asp Lys Met Ala Glu Ala Tyr Ser Glu Ile Gly Met Lys Gly Glu Arg
        755                 760                 765

Arg Arg Gly Lys Gly His Asp Gly Leu Tyr Gln Gly Leu Ser Thr Ala
    770                 775                 780

Thr Lys Asp Thr Tyr Asp Ala Leu His Met Gln Ala Leu Pro Pro Arg
785                 790                 795                 800


<210> SEQ ID NO 16
<211> LENGTH: 2403
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

atgaccacac ctcggaacag cgtgaacggc acatttcccg ccgagcctat gaagggccct     60

atcgccatgc agtctggccc caagcctctg ttcagacgga tgtctagcct cgtgggcccc    120

acacagagct tttcatgag agagagcaag accctgggcg ccgtgcagat catgaacggc    180

ctgtttcaca ttgccctcgg cggcctgctg atgatccctg ccggaatcta tgcccctatc    240

tgcgtgaccg tgtggtatcc tctgtggggc ggcatcatgt acatcatctc tggatctctg    300

ctggccgcca ccgagaagaa cagcagaaag tgtctggtca agggcaagat gatcatgaat    360

agcctgagcc tgttcgccgc catcagcggc atgatcctga gcatcatgga tatcctgaat    420

atcaagatca gccacttcct gaagatggaa agcctgaact tcatcagggc ccacacacct    480

tacatcaaca tctacaactg cgagcccgcc aatcctagcg agaagaatag ccccagcaca    540

cagtactgct actctatcca gagcctgttt ctgggcatcc tgagcgtgat gctgatcttc    600

gcattcttcc aagagctggt tatcgccggc atcgtggaaa acgagtggaa gcggacctgc    660

agcagaccca agagcaacat cgtgctgctg agcgccgagg aaaagaaaga gcagaccatc    720

gagatcaaag aggaagtcgt cggcctgacc gagacaagca gccagcctaa gaacgaagag    780

gacattgaga tcatccccat ccaagaagag gaagaagaag agactgagac aaacttcccc    840

gagcctcctc aggaccaaga gagcagcccc attgagaacg atagcagccc tgcctccaga    900

gccgaaggca gaggatcact gctgacatgc ggcgacgtgg aagagaaccc tggacccatg    960

gccttaccag tgaccgcctt gctcctgccg ctggccttgc tgctccacgc cgccaggccg   1020

caggtgcagc tgcagcagcc tggcgctgaa ctcgtgcggc caggcgcttc tgtgaagctg   1080

agctgtaaag ccagcggcta caccttcacc agctactgga tgaactgggt caagcagcgg   1140

cccgaccagg gcctggaatg gatcggaaga atcgacccct acgacagcga gacacactac   1200

aaccagaagt tcaaggacaa ggccatcctg accgtggaca agagcagcag caccgcctac   1260

atgcagctgt ccagcctgac cagcgaggac agcgccgtgt actactgcgc cagaggcaac   1320

tgggacgact actggggcca gggcacaacc ctgacagtgt ctagcggagg cggaggatca   1380

ggcggcggag gaagtggggg aggcggatct gatgtgcaga ttacccagtc ccccagctac   1440
```

```
ctggccgcct ctcctggcga gacaatcacc atcaactgcc gggccagcaa gagcatctcc   1500

aaggacctgg cctggtatca ggaaaagccc ggcaagacca acaagctgct gatctacagc   1560

ggctccaccc tgcagtccgg catccccagc agattttccg gcagcggctc tggcaccgac   1620

ttcaccctga ccatcagctc cctggaaccc gaggactttg ccatgtacta ttgccagcag   1680

cacaacaagt acccttacac cttcggcgga ggcaccaagc tggaaatcaa gagcaccacg   1740

acgccagcgc cgcgaccacc aacgccggcg cccaccatcg cgtcgcagcc cctgtccctg   1800

cgcccagagg cgtgccggcc agcggcgggg ggcgcagtgc acacgagggg gctggacttc   1860

gcctgtgata tctacatctg ggcgcccttg gccgggactt gtggggtcct tctcctgtca   1920

ctggttatca ccctttactg ccgaagcaag cggagccggc tgctgcacag cgactacatg   1980

aacatgaccc ctagacggcc cggaccaacc agaaagcact accagcctta cgctcctcct   2040

agagatttcg ccgcctaccg gtccagagtg aagttcagca ggagcgcaga cgcccccgcg   2100

taccagcagg gccagaacca gctctataac gagctcaatc taggacgaag agaggagtac   2160

gatgttttgg acaagagacg tggccgggac cctgagatgg ggggaaagcc gagaaggaag   2220

aaccctcagg aaggcctgta caatgaactg cagaaagata agatggcgga ggcctacagt   2280

gagattggga tgaaaggcga gcgccggagg ggcaaggggc acgatggcct ttaccagggt   2340

ctcagtacag ccaccaagga cacctacgac gcccttcaca tgcaggccct gccccctcgc   2400

taa                                                                 2403
```

```
<210> SEQ ID NO 17
<211> LENGTH: 839
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175
```

```
Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro Ala Ser Arg Ala Glu Gly Arg
    290                 295                 300

Gly Ser Leu Leu Thr Cys Gly Asp Val Glu Glu Asn Pro Gly Pro Met
305                 310                 315                 320

Ala Leu Pro Val Thr Ala Leu Leu Leu Pro Leu Ala Leu Leu Leu His
                325                 330                 335

Ala Ala Arg Pro Gln Val Gln Leu Gln Gln Pro Gly Ala Glu Leu Val
            340                 345                 350

Arg Pro Gly Ala Ser Val Lys Leu Ser Cys Lys Ala Ser Gly Tyr Thr
        355                 360                 365

Phe Thr Ser Tyr Trp Met Asn Trp Val Lys Gln Arg Pro Asp Gln Gly
    370                 375                 380

Leu Glu Trp Ile Gly Arg Ile Asp Pro Tyr Asp Ser Glu Thr His Tyr
385                 390                 395                 400

Asn Gln Lys Phe Lys Asp Lys Ala Ile Leu Thr Val Asp Lys Ser Ser
                405                 410                 415

Ser Thr Ala Tyr Met Gln Leu Ser Ser Leu Thr Ser Glu Asp Ser Ala
            420                 425                 430

Val Tyr Tyr Cys Ala Arg Gly Asn Trp Asp Asp Tyr Trp Gly Gln Gly
        435                 440                 445

Thr Thr Leu Thr Val Ser Ser Gly Gly Gly Gly Ser Gly Gly Gly Gly
    450                 455                 460

Ser Gly Gly Gly Gly Ser Asp Val Gln Ile Thr Gln Ser Pro Ser Tyr
465                 470                 475                 480

Leu Ala Ala Ser Pro Gly Glu Thr Ile Thr Ile Asn Cys Arg Ala Ser
                485                 490                 495

Lys Ser Ile Ser Lys Asp Leu Ala Trp Tyr Gln Glu Lys Pro Gly Lys
            500                 505                 510

Thr Asn Lys Leu Leu Ile Tyr Ser Gly Ser Thr Leu Gln Ser Gly Ile
        515                 520                 525

Pro Ser Arg Phe Ser Gly Ser Gly Ser Gly Thr Asp Phe Thr Leu Thr
    530                 535                 540

Ile Ser Ser Leu Glu Pro Glu Asp Phe Ala Met Tyr Tyr Cys Gln Gln
545                 550                 555                 560

His Asn Lys Tyr Pro Tyr Thr Phe Gly Gly Gly Thr Lys Leu Glu Ile
                565                 570                 575

Lys Ser Ile Glu Val Met Tyr Pro Pro Pro Tyr Leu Asp Asn Glu Lys
            580                 585                 590

Ser Asn Gly Thr Ile Ile His Val Lys Gly Lys His Leu Cys Pro Ser
```

```
        595                 600                 605

Pro Leu Phe Pro Gly Pro Ser Lys Pro Phe Trp Val Leu Val Val Val
    610                 615                 620

Gly Gly Val Leu Ala Cys Tyr Ser Leu Leu Val Thr Val Ala Phe Ile
625                 630                 635                 640

Ile Phe Trp Val Arg Ser Lys Arg Ser Arg Leu Leu His Ser Asp Tyr
                645                 650                 655

Met Asn Met Thr Pro Arg Arg Pro Gly Pro Thr Arg Lys His Tyr Gln
            660                 665                 670

Pro Tyr Ala Pro Pro Arg Asp Phe Ala Ala Tyr Arg Ser Lys Arg Gly
        675                 680                 685

Arg Lys Lys Leu Leu Tyr Ile Phe Lys Gln Pro Phe Met Arg Pro Val
    690                 695                 700

Gln Thr Thr Gln Glu Glu Asp Gly Cys Ser Cys Arg Phe Pro Glu Glu
705                 710                 715                 720

Glu Glu Gly Gly Cys Glu Leu Arg Val Lys Phe Ser Arg Ser Ala Asp
                725                 730                 735

Ala Pro Ala Tyr Gln Gln Gly Gln Asn Gln Leu Tyr Asn Glu Leu Asn
            740                 745                 750

Leu Gly Arg Arg Glu Glu Tyr Asp Val Leu Asp Lys Arg Arg Gly Arg
        755                 760                 765

Asp Pro Glu Met Gly Gly Lys Pro Arg Arg Lys Asn Pro Gln Glu Gly
    770                 775                 780

Leu Tyr Asn Glu Leu Gln Lys Asp Lys Met Ala Glu Ala Tyr Ser Glu
785                 790                 795                 800

Ile Gly Met Lys Gly Glu Arg Arg Arg Gly Lys Gly His Asp Gly Leu
                805                 810                 815

Tyr Gln Gly Leu Ser Thr Ala Thr Lys Asp Thr Tyr Asp Ala Leu His
            820                 825                 830

Met Gln Ala Leu Pro Pro Arg
        835


<210> SEQ ID NO 18
<211> LENGTH: 2520
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

atgaccacac ctcggaacag cgtgaacggc acatttcccg ccgagcctat gaagggccct      60

atcgccatgc agtctggccc caagcctctg ttcagacgga tgtctagcct cgtgggcccc     120

acacagagct ttttcatgag agagagcaag accctgggcg ccgtgcagat catgaacggc     180

ctgtttcaca ttgccctcgg cggcctgctg atgatccctg ccggaatcta tgcccctatc     240

tgcgtgaccg tgtggtatcc tctgtggggc ggcatcatgt acatcatctc tggatctctg     300

ctggccgcca ccgagaagaa cagcagaaag tgtctggtca agggcaagat gatcatgaat     360

agcctgagcc tgttcgccgc catcagcggc atgatcctga gcatcatgga tatcctgaat     420

atcaagatca gccacttcct gaagatggaa agcctgaact tcatcagggc ccacacacct     480

tacatcaaca tctacaactg cgagcccgcc aatcctagcg agaagaatag ccccagcaca     540

cagtactgct actctatcca gagcctgttt ctgggcatcc tgagcgtgat gctgatcttc     600

gcattcttcc aagagctggt tatcgccggc atcgtggaaa acgagtggaa gcggacctgc     660
```

```
agcagaccca agagcaacat cgtgctgctg agcgccgagg aaaagaaaga gcagaccatc    720
gagatcaaag aggaagtcgt cggcctgacc gagacaagca gccagcctaa gaacgaagag    780
gacattgaga tcatccccat ccaagaagag gaagaagaag agactgagac aaacttcccc    840
gagcctcctc aggaccaaga gagcagcccc attgagaacg atagcagccc tgcctccaga    900
gccgaaggca gaggatcact gctgacatgc ggcgacgtgg aagagaaccc tggacccatg    960
gccttaccag tgaccgcctt gctcctgccg ctggccttgc tgctccacgc cgccaggccg   1020
caggtgcagc tgcagcagcc tggcgctgaa ctcgtgcggc caggcgcttc tgtgaagctg   1080
agctgtaaag ccagcggcta caccttcacc agctactgga tgaactgggt caagcagcgg   1140
cccgaccagg gcctggaatg gatcggaaga atcgacccct acgacagcga gacacactac   1200
aaccagaagt tcaaggacaa ggccatcctg accgtggaca agagcagcag caccgcctac   1260
atgcagctgt ccagcctgac cagcgaggac agcgccgtgt actactgcgc cagaggcaac   1320
tgggacgact actggggcca gggcacaacc ctgacagtgt ctagcggagg cggaggatca   1380
ggcggcggag gaagtggggg aggcggatct gatgtgcaga ttacccagtc ccccagctac   1440
ctggccgcct ctcctggcga gacaatcacc atcaactgcc gggccagcaa gagcatctcc   1500
aaggacctgg cctggtatca ggaaaagccc ggcaagacca acaagctgct gatctacagc   1560
ggctccaccc tgcagtccgg catccccagc agattttccg gcagcggctc tggcaccgac   1620
ttcaccctga ccatcagctc cctggaaccc gaggactttg ccatgtacta ttgccagcag   1680
cacaacaagt acccttacac cttcggcgga ggcaccaagc tggaaatcaa gagcatcgaa   1740
gtgatgtacc cgcctcctta cctggacaac gagaagtcca acggcaccat catccacgtg   1800
aagggaaagc acctgtgtcc ttctccactg ttccccggac ctagcaagcc tttctgggtg   1860
ctcgttgttg ttggcggcgt gctggcctgt tacagcctgc tggttaccgt ggccttcatc   1920
atcttttggg tccgaagcaa gcggagccgg ctgctgcaca gcgactacat gaacatgacc   1980
cctagacggc ccggaccaac cagaaagcac taccagcctt acgctcctcc tagagatttc   2040
gccgcctacc ggtccaaacg gggcagaaag aaactcctgt atatattcaa acaaccattt   2100
atgagaccag tacaaactac tcaagaggaa gatggctgta gctgccgatt tccagaagaa   2160
gaagaaggag gatgtgaact gagagtgaag ttcagcagga gcgcagacgc ccccgcgtac   2220
cagcagggcc agaaccagct ctataacgag ctcaatctag gacgaagaga ggagtacgat   2280
gttttggaca agagacgtgg ccgggaccct gagatggggg gaaagccgag aaggaagaac   2340
cctcaggaag gcctgtacaa tgaactgcag aaagataaga tggcggaggc ctacagtgag   2400
attgggatga aaggcgagcg ccggaggggc aaggggcacg atggccttta ccagggtctc   2460
agtacagcca ccaaggacac ctacgacgcc cttcacatgc aggccctgcc ccctcgctaa   2520
```

```
<210> SEQ ID NO 19
<211> LENGTH: 798
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30
```

```
Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro Ala Ser Arg Ala Glu Gly Arg
    290                 295                 300

Gly Ser Leu Leu Thr Cys Gly Asp Val Glu Glu Asn Pro Gly Pro Met
305                 310                 315                 320

Ala Leu Pro Val Thr Ala Leu Leu Leu Pro Leu Ala Leu Leu Leu His
                325                 330                 335

Ala Ala Arg Pro Gln Val Gln Leu Gln Gln Pro Gly Ala Glu Leu Val
            340                 345                 350

Arg Pro Gly Ala Ser Val Lys Leu Ser Cys Lys Ala Ser Gly Tyr Thr
        355                 360                 365

Phe Thr Ser Tyr Trp Met Asn Trp Val Lys Gln Arg Pro Asp Gln Gly
    370                 375                 380

Leu Glu Trp Ile Gly Arg Ile Asp Pro Tyr Asp Ser Glu Thr His Tyr
385                 390                 395                 400

Asn Gln Lys Phe Lys Asp Lys Ala Ile Leu Thr Val Asp Lys Ser Ser
                405                 410                 415

Ser Thr Ala Tyr Met Gln Leu Ser Ser Leu Thr Ser Glu Asp Ser Ala
            420                 425                 430

Val Tyr Tyr Cys Ala Arg Gly Asn Trp Asp Asp Tyr Trp Gly Gln Gly
        435                 440                 445
```

```
Thr Thr Leu Thr Val Ser Ser Gly Gly Gly Gly Ser Gly Gly Gly Gly
    450                 455                 460

Ser Gly Gly Gly Gly Ser Asp Val Gln Ile Thr Gln Ser Pro Ser Tyr
465                 470                 475                 480

Leu Ala Ala Ser Pro Gly Glu Thr Ile Thr Ile Asn Cys Arg Ala Ser
                485                 490                 495

Lys Ser Ile Ser Lys Asp Leu Ala Trp Tyr Gln Glu Lys Pro Gly Lys
            500                 505                 510

Thr Asn Lys Leu Leu Ile Tyr Ser Gly Ser Thr Leu Gln Ser Gly Ile
        515                 520                 525

Pro Ser Arg Phe Ser Gly Ser Gly Ser Gly Thr Asp Phe Thr Leu Thr
    530                 535                 540

Ile Ser Ser Leu Glu Pro Glu Asp Phe Ala Met Tyr Tyr Cys Gln Gln
545                 550                 555                 560

His Asn Lys Tyr Pro Tyr Thr Phe Gly Gly Gly Thr Lys Leu Glu Ile
                565                 570                 575

Lys Ser Ser Ile Glu Val Met Tyr Pro Pro Pro Tyr Leu Asp Asn Glu
            580                 585                 590

Lys Ser Asn Gly Thr Ile Ile His Val Lys Gly Lys His Leu Cys Pro
        595                 600                 605

Ser Pro Leu Phe Pro Gly Pro Ser Lys Pro Phe Trp Val Leu Val Val
    610                 615                 620

Val Gly Gly Val Leu Ala Cys Tyr Ser Leu Leu Val Thr Val Ala Phe
625                 630                 635                 640

Ile Ile Phe Trp Val Arg Ser Lys Arg Ser Arg Leu Leu His Ser Asp
                645                 650                 655

Tyr Met Asn Met Thr Pro Arg Arg Pro Gly Pro Thr Arg Lys His Tyr
            660                 665                 670

Gln Pro Tyr Ala Pro Pro Arg Asp Phe Ala Ala Tyr Arg Ser Arg Val
        675                 680                 685

Lys Phe Ser Arg Ser Ala Asp Ala Pro Ala Tyr Gln Gln Gly Gln Asn
    690                 695                 700

Gln Leu Tyr Asn Glu Leu Asn Leu Gly Arg Arg Glu Glu Tyr Asp Val
705                 710                 715                 720

Leu Asp Lys Arg Arg Gly Arg Asp Pro Glu Met Gly Gly Lys Pro Arg
                725                 730                 735

Arg Lys Asn Pro Gln Glu Gly Leu Tyr Asn Glu Leu Gln Lys Asp Lys
            740                 745                 750

Met Ala Glu Ala Tyr Ser Glu Ile Gly Met Lys Gly Glu Arg Arg Arg
        755                 760                 765

Gly Lys Gly His Asp Gly Leu Tyr Gln Gly Leu Ser Thr Ala Thr Lys
    770                 775                 780

Asp Thr Tyr Asp Ala Leu His Met Gln Ala Leu Pro Pro Arg
785                 790                 795
```

<210> SEQ ID NO 20
<211> LENGTH: 2397
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 20

```
atgaccacac ctcggaacag cgtgaacggc acatttcccg ccgagcctat gaagggccct     60
```

-continued

```
atcgccatgc agtctggccc caagcctctg ttcagacgga tgtctagcct cgtgggcccc     120

acacagagct ttttcatgag agagagcaag accctgggcg ccgtgcagat catgaacggc     180

ctgtttcaca ttgccctcgg cggcctgctg atgatccctg ccggaatcta tgcccctatc     240

tgcgtgaccg tgtggtatcc tctgtggggc ggcatcatgt acatcatctc tggatctctg     300

ctggccgcca ccgagaagaa cagcagaaag tgtctggtca agggcaagat gatcatgaat     360

agcctgagcc tgttcgccgc catcagcggc atgatcctga gcatcatgga tatcctgaat     420

atcaagatca gccacttcct gaagatggaa agcctgaact tcatcagggc ccacacacct     480

tacatcaaca tctacaactg cgagcccgcc aatcctagcg agaagaatag ccccagcaca     540

cagtactgct actctatcca gagcctgttt ctgggcatcc tgagcgtgat gctgatcttc     600

gcattcttcc aagagctggt tatcgccggc atcgtggaaa acgagtggaa gcggacctgc     660

agcagaccca agagcaacat cgtgctgctg agcgccgagg aaaagaaaga gcagaccatc     720

gagatcaaag aggaagtcgt cggcctgacc gagacaagca gccagcctaa gaacgaagag     780

gacattgaga tcatccccat ccaagaagag gaagaagaag agactgagac aaacttcccc     840

gagcctcctc aggaccaaga gagcagcccc attgagaacg atagcagccc tgcctccaga     900

gccgaaggca gaggatcact gctgacatgc ggcgacgtgg aagagaaccc tggacccatg     960

gccttaccag tgaccgcctt gctcctgccg ctggccttgc tgctccacgc cgccaggccg    1020

caggtgcagc tgcagcagcc tggcgctgaa ctcgtgcggc caggcgcttc tgtgaagctg    1080

agctgtaaag ccagcggcta caccttcacc agctactgga tgaactgggt caagcagcgg    1140

cccgaccagg gcctggaatg gatcggaaga atcgacccct acgacagcga gacacactac    1200

aaccagaagt tcaaggacaa ggccatcctg accgtggaca agagcagcag caccgcctac    1260

atgcagctgt ccagcctgac cagcgaggac agcgccgtgt actactgcgc cagaggcaac    1320

tgggacgact actggggcca gggcacaacc ctgacagtgt ctagcggagg cggaggatca    1380

ggcggcggag gaagtggggg aggcggatct gatgtgcaga ttacccagtc ccccagctac    1440

ctggccgcct ctcctggcga gacaatcacc atcaactgcc gggccagcaa gagcatctcc    1500

aaggacctgg cctggtatca ggaaaagccc ggcaagacca acaagctgct gatctacagc    1560

ggctccaccc tgcagtccgg catccccagc agattttccg gcagcggctc tggcaccgac    1620

ttcaccctga ccatcagctc cctggaaccc gaggactttg ccatgtacta ttgccagcag    1680

cacaacaagt acccttacac cttcggcgga ggcaccaagc tggaaatcaa gagcagcatc    1740

gaagtgatgt acccgcctcc ttacctggac aacgagaagt ccaacggcac catcatccac    1800

gtgaagggaa agcacctgtg tccttctcca ctgttccccg gacctagcaa gcctttctgg    1860

gtgctcgttg ttgttggcgg cgtgctggcc tgttacagcc tgctggttac cgtggccttc    1920

atcatctttt gggtccgaag caagcggagc cggctgctgc acagcgacta catgaacatg    1980

acccctagac ggcccggacc aaccagaaag cactaccagc cttacgctcc tcctagagat    2040

ttcgccgcct accggtccag agtgaagttc agcaggagcg cagacgcccc cgcgtaccag    2100

cagggccaga accagctcta taacgagctc aatctaggac gaagagagga gtacgatgtt    2160

ttggacaaga gacgtggccg ggaccctgag atggggggaa agccgagaag gaagaaccct    2220

caggaaggcc tgtacaatga actgcagaaa gataagatgg cggaggccta cagtgagatt    2280

gggatgaaag gcgagcgccg gaggggcaag gggcacgatg gcctttacca gggtctcagt    2340

acagccacca aggacaccta cgacgccctt cacatgcagg ccctgccccc tcgctaa       2397
```

```
<210> SEQ ID NO 21
<211> LENGTH: 806
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro Ala Ser Arg Ala Glu Gly Arg
    290                 295                 300

Gly Ser Leu Leu Thr Cys Gly Asp Val Glu Glu Asn Pro Gly Pro Met
305                 310                 315                 320

Ala Leu Pro Val Thr Ala Leu Leu Leu Pro Leu Ala Leu Leu Leu His
                325                 330                 335

Ala Ala Arg Pro Gln Ile Gln Leu Val Gln Ser Gly Pro Glu Leu Lys
            340                 345                 350

Lys Pro Gly Glu Thr Val Lys Ile Ser Cys Lys Ala Ser Gly Tyr Ile
        355                 360                 365
```

```
Phe Thr Asn Tyr Gly Met Asn Trp Val Lys Gln Ala Pro Gly Lys Ser
    370                 375                 380

Phe Lys Trp Met Gly Trp Ile Asn Thr Tyr Thr Gly Glu Ser Thr Tyr
385                 390                 395                 400

Ser Ala Asp Phe Lys Gly Arg Phe Ala Phe Ser Leu Glu Thr Ser Ala
                405                 410                 415

Ser Thr Ala Tyr Leu His Ile Asn Asp Leu Lys Asn Glu Asp Thr Ala
            420                 425                 430

Thr Tyr Phe Cys Ala Arg Ser Gly Gly Tyr Asp Pro Met Asp Tyr Trp
        435                 440                 445

Gly Gln Gly Thr Ser Val Thr Val Ser Ser Gly Gly Gly Gly Ser Gly
    450                 455                 460

Gly Gly Gly Ser Gly Gly Gly Gly Ser Asp Ile Val Leu Thr Gln Ser
465                 470                 475                 480

Pro Ala Ser Leu Ala Val Ser Leu Gly Gln Arg Ala Thr Ile Ser Cys
                485                 490                 495

Arg Ala Ser Glu Ser Val Asp Asn Tyr Gly Asn Thr Phe Met His Trp
            500                 505                 510

Tyr Gln Gln Lys Pro Gly Gln Pro Pro Lys Leu Leu Ile Tyr Arg Ala
        515                 520                 525

Ser Asn Leu Glu Ser Gly Ile Pro Ala Arg Phe Ser Gly Ser Gly Ser
    530                 535                 540

Arg Thr Asp Phe Thr Leu Thr Ile Asn Pro Val Glu Ala Asp Asp Val
545                 550                 555                 560

Ala Thr Tyr Tyr Cys Gln Gln Ser Asn Glu Asp Pro Pro Thr Phe Gly
                565                 570                 575

Ala Gly Thr Lys Leu Glu Leu Lys Thr Thr Thr Pro Ala Pro Arg Pro
            580                 585                 590

Pro Thr Pro Ala Pro Thr Ile Ala Ser Gln Pro Leu Ser Leu Arg Pro
        595                 600                 605

Glu Ala Cys Arg Pro Ala Ala Gly Gly Ala Val His Thr Arg Gly Leu
    610                 615                 620

Asp Phe Ala Cys Asp Ile Tyr Ile Trp Ala Pro Leu Ala Gly Thr Cys
625                 630                 635                 640

Gly Val Leu Leu Leu Ser Leu Val Ile Thr Leu Tyr Cys Arg Ser Lys
                645                 650                 655

Arg Ser Arg Leu Leu His Ser Asp Tyr Met Asn Met Thr Pro Arg Arg
            660                 665                 670

Pro Gly Pro Thr Arg Lys His Tyr Gln Pro Tyr Ala Pro Pro Arg Asp
        675                 680                 685

Phe Ala Ala Tyr Arg Ser Arg Val Lys Phe Ser Arg Ser Ala Asp Ala
    690                 695                 700

Pro Ala Tyr Gln Gln Gly Gln Asn Gln Leu Tyr Asn Glu Leu Asn Leu
705                 710                 715                 720

Gly Arg Arg Glu Glu Tyr Asp Val Leu Asp Lys Arg Arg Gly Arg Asp
                725                 730                 735

Pro Glu Met Gly Gly Lys Pro Arg Arg Lys Asn Pro Gln Glu Gly Leu
            740                 745                 750

Tyr Asn Glu Leu Gln Lys Asp Lys Met Ala Glu Ala Tyr Ser Glu Ile
        755                 760                 765

Gly Met Lys Gly Glu Arg Arg Arg Gly Lys Gly His Asp Gly Leu Tyr
    770                 775                 780

Gln Gly Leu Ser Thr Ala Thr Lys Asp Thr Tyr Asp Ala Leu His Met
```

785 790 795 800

Gln Ala Leu Pro Pro Arg
805

<210> SEQ ID NO 22
<211> LENGTH: 2421
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22
atgaccacac ctcggaacag cgtgaacggc acatttcccg ccgagcctat gaagggccct 60
atcgccatgc agtctggccc caagcctctg ttcagacgga tgtctagcct cgtgggcccc 120
acacagagct tttcatgag agagagcaag accctgggcg ccgtgcagat catgaacggc 180
ctgtttcaca ttgccctcgg cggcctgctg atgatccctg ccggaatcta tgcccctatc 240
tgcgtgaccg tgtggtatcc tctgtggggc ggcatcatgt acatcatctc tggatctctg 300
ctggccgcca ccgagaagaa cagcagaaag tgtctggtca agggcaagat gatcatgaat 360
agcctgagcc tgttcgccgc catcagcggc atgatcctga gcatcatgga tatcctgaat 420
atcaagatca gccacttcct gaagatggaa agcctgaact tcatcagggc ccacacacct 480
tacatcaaca tctacaactg cgagcccgcc aatcctagcg agaagaatag ccccagcaca 540
cagtactgct actctatcca gagcctgttt ctgggcatcc tgagcgtgat gctgatcttc 600
gcattcttcc aagagctggt tatcgccggc atcgtggaaa acgagtggaa gcggacctgc 660
agcagaccca agagcaacat cgtgctgctg agcgccgagg aaaagaaaga gcagaccatc 720
gagatcaaag aggaagtcgt cggcctgacc gagacaagca gccagcctaa gaacgaagag 780
gacattgaga tcatccccat ccaagaagag gaagaagaag agactgagac aaacttcccc 840
gagcctcctc aggaccaaga gagcagcccc attgagaacg atagcagccc tgcctccaga 900
gccgaaggca gaggatcact gctgacatgc ggcgacgtgg aagagaaccc tggacccatg 960
gccttaccag tgaccgcctt gctcctgccg ctggccttgc tgctccacgc cgccaggccg 1020
cagattcagc tggtgcagtc tggccccgag ctgaagaaac ccggcgagac agtgaagatc 1080
agctgcaagg ccagcggcta catcttcacc aactacggca tgaactgggt caagcaggcc 1140
cctggcaaga gcttcaagtg gatgggctgg atcaacacct acaccggcga gagcacctac 1200
agcgccgact tcaagggcag attcgccttc agcctggaaa ccagcgccag caccgcctac 1260
ctgcacatca acgacctgaa gaacgaggac accgccacct acttttgcgc cagaagcggc 1320
ggctacgacc ctatggatta ttggggccag ggcaccagcg tgaccgtgtc tagcggaggc 1380
ggaggaagtg gcggcggagg atctggggga ggcggatctg atatcgtgct gacccagagc 1440
cctgccagcc tggctgtgtc tctgggacag agagccacca tcagctgtcg ggccagcgag 1500
agcgtggaca attacggcaa caccttcatg cactggtatc agcagaagcc cggccagccc 1560
cccaagctgc tgatctacag agccagcaac ctggaaagcg gcatccccgc cagattttcc 1620
ggcagcggca gcagaaccga cttcaccctg accatcaacc ccgtggaagc cgacgacgtg 1680
gccacctatt actgccagca gagcaacgag gacccccta cctttggagc cggcaccaag 1740
ctggaactga agaccacgac gccagcgccg cgaccaccaa cgccggcgcc caccatcgcg 1800
tcgcagcccc tgtccctgcg cccagaggcg tgccggccag cggcgggggg cgcagtgcac 1860
acgagggggc tggacttcgc ctgtgatatc tacatctggg cgcccttggc cgggacttgt 1920

```
ggggtccttc tcctgtcact ggttatcacc ctttactgcc ggtccaagag aagcagactg   1980

ctgcacagcg actacatgaa catgacccct agacggcccg gacctaccag aaagcactac   2040

cagccttacg ctcctcctag agatttcgcc gcctaccggt ccagagtgaa gttcagcagg   2100

agcgcagacg cccccgcgta ccagcagggc cagaaccagc tctataacga gctcaatcta   2160

ggacgaagag aggagtacga tgttttggac aagagacgtg gccgggaccc tgagatgggg   2220

ggaaagccga gaaggaagaa ccctcaggaa ggcctgtaca atgaactgca gaaagataag   2280

atggcggagg cctacagtga gattgggatg aaaggcgagc gccggagggg caaggggcac   2340

gatggccttt accagggtct cagtacagcc accaaggaca cctacgacgc ccttcacatg   2400

caggccctgc cccctcgcta a                                             2421
```

<210> SEQ ID NO 23
<211> LENGTH: 791
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Ser Asn Tyr Leu Met Asn Trp Val Lys Gln Arg Pro Glu Gln Asp Leu
    50                  55                  60

Asp Trp Ile Gly Arg Ile Asp Pro Tyr Asp Gly Asp Ile Asp Tyr Asn
65                  70                  75                  80

Gln Asn Phe Lys Asp Lys Ala Ile Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Tyr Gly Thr Ala Tyr Gly Val Asp Tyr Trp
        115                 120                 125

Gly Gln Gly Thr Ser Val Thr Val Ser Ser Ala Lys Thr Thr Pro Pro
    130                 135                 140

Lys Leu Glu Glu Gly Glu Phe Ser Glu Ala Arg Val Asp Ile Val Leu
145                 150                 155                 160

Thr Gln Ser Pro Ala Ser Leu Ala Val Ser Leu Gly Gln Arg Ala Thr
                165                 170                 175

Ile Ser Cys Arg Ala Ser Glu Ser Val Asp Asn Tyr Gly Ile Ser Phe
            180                 185                 190

Met Asn Trp Phe Gln Gln Lys Pro Gly Gln Pro Pro Lys Leu Leu Ile
        195                 200                 205

Tyr Ala Ala Ser Arg Gln Gly Ser Gly Val Pro Ala Arg Phe Ser Gly
    210                 215                 220

Ser Gly Ser Gly Thr Asp Phe Ser Leu Asn Ile His Pro Met Glu Glu
225                 230                 235                 240

Asp Asp Thr Ala Met Tyr Phe Cys Gln Gln Ser Lys Glu Val Pro Trp
                245                 250                 255

Thr Phe Gly Gly Gly Thr Lys Leu Glu Ile Lys Asp Leu Glu Pro Lys
```

```
            260                 265                 270

Ser Cys Asp Lys Thr His Thr Cys Pro Pro Cys Pro Asp Pro Lys Phe
        275                 280                 285

Trp Val Leu Val Val Val Gly Gly Val Leu Ala Cys Tyr Ser Leu Leu
    290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
                325                 330                 335

Thr Arg Lys His Tyr Gln Pro Tyr Ala Pro Pro Arg Asp Phe Ala Ala
            340                 345                 350

Tyr Arg Ser Arg Val Lys Phe Ser Arg Ser Ala Asp Ala Pro Ala Tyr
        355                 360                 365

Gln Gln Gly Gln Asn Gln Leu Tyr Asn Glu Leu Asn Leu Gly Arg Arg
    370                 375                 380

Glu Glu Tyr Asp Val Leu Asp Lys Arg Arg Gly Arg Asp Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg Ala Ser Arg Ala Glu Gly Arg Gly
465                 470                 475                 480

Ser Leu Leu Thr Cys Gly Asp Val Glu Glu Asn Pro Gly Pro Met Thr
                485                 490                 495

Thr Pro Arg Asn Ser Val Asn Gly Thr Phe Pro Ala Glu Pro Met Lys
            500                 505                 510

Gly Pro Ile Ala Met Gln Ser Gly Pro Lys Pro Leu Phe Arg Arg Met
        515                 520                 525

Ser Ser Leu Val Gly Pro Thr Gln Ser Phe Phe Met Arg Glu Ser Lys
    530                 535                 540

Thr Leu Gly Ala Val Gln Ile Met Asn Gly Leu Phe His Ile Ala Leu
545                 550                 555                 560

Gly Gly Leu Leu Met Ile Pro Ala Gly Ile Tyr Ala Pro Ile Cys Val
                565                 570                 575

Thr Val Trp Tyr Pro Leu Trp Gly Gly Ile Met Tyr Ile Ile Ser Gly
            580                 585                 590

Ser Leu Leu Ala Ala Thr Glu Lys Asn Ser Arg Lys Cys Leu Val Lys
        595                 600                 605

Gly Lys Met Ile Met Asn Ser Leu Ser Leu Phe Ala Ala Ile Ser Gly
    610                 615                 620

Met Ile Leu Ser Ile Met Asp Ile Leu Asn Ile Lys Ile Ser His Phe
625                 630                 635                 640

Leu Lys Met Glu Ser Leu Asn Phe Ile Arg Ala His Thr Pro Tyr Ile
                645                 650                 655

Asn Ile Tyr Asn Cys Glu Pro Ala Asn Pro Ser Glu Lys Asn Ser Pro
            660                 665                 670

Ser Thr Gln Tyr Cys Tyr Ser Ile Gln Ser Leu Phe Leu Gly Ile Leu
        675                 680                 685
```

```
Ser Val Met Leu Ile Phe Ala Phe Phe Gln Glu Leu Val Ile Ala Gly
    690                 695                 700

Ile Val Glu Asn Glu Trp Lys Arg Thr Cys Ser Arg Pro Lys Ser Asn
705                 710                 715                 720

Ile Val Leu Leu Ser Ala Glu Glu Lys Lys Glu Gln Thr Ile Glu Ile
                725                 730                 735

Lys Glu Glu Val Val Gly Leu Thr Glu Thr Ser Ser Gln Pro Lys Asn
            740                 745                 750

Glu Glu Asp Ile Glu Ile Ile Pro Ile Gln Glu Glu Glu Glu Glu Glu
        755                 760                 765

Thr Glu Thr Asn Phe Pro Glu Pro Pro Gln Asp Gln Glu Ser Ser Pro
    770                 775                 780

Ile Glu Asn Asp Ser Ser Pro
785                 790
```

<210> SEQ ID NO 24
<211> LENGTH: 2376
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
atggactgga tctggcgcat cctgtttctc gtgggagccg ccacaggcgc ccattctcag      60

gtgcagctgc agcagcctgg cgctgaactc gtgcggccag gcgcttctgt gaagctgagc     120

tgtaaagcca gcggctacac cttcagcaac tacctgatga actgggtcaa gcagcggccc     180

gagcaggacc tggattggat cggcagaatc gacccctacg acggcgacat cgactacaac     240

cagaacttca aggacaaggc catcctgacc gtggacaaga gcagcagcac cgcctacatg     300

cagctgtcca gcctgaccag cgaggacagc gccgtgtact actgcgccag aggctacggc     360

acagcctacg gcgtggacta ttggggccag ggcacaagcg tgaccgtgtc cagcgccaag     420

accacccccc ctaagctgga agagggcgag ttctccgagg cccgggtgga cattgtgctg     480

acacagtctc cagccagcct ggccgtgtcc ctgggacaga gagccaccat cagctgtagg     540

gccagcgaga gcgtggacaa ctacggcatc agcttcatga attggttcca gcagaagccc     600

ggccagcccc ccaagctgct gatctatgcc gccagcagac agggcagcgg agtgcctgcc     660

agattttctg gcagcggctc cggcaccgac ttcagcctga acatccaccc tatggaagag     720

gacgacaccg ccatgtactt ttgccagcag agcaaagagg tgccctggac ctttggcgga     780

ggcaccaagc tggaaatcaa ggatctcgag cccaaatctt gtgacaaaac tcacacatgc     840

ccaccgtgcc cggatcccaa attttgggtg ctggtggtgg ttggtggagt cctggcttgc     900

tatagcttgc tagtaacagt ggcctttatt attttctggg tgaggagtaa gaggagcagg     960

ctcctgcaca gtgactacat gaacatgact ccccgccgcc ccgggcccac ccgcaagcat    1020

taccagccct atgccccacc acgcgacttc gcagcctatc gctccagagt gaagttcagc    1080

aggagcgcag acgcccccgc gtaccagcag ggccagaacc agctctataa cgagctcaat    1140

ctaggacgaa gagaggagta cgatgttttg gacaagagac gtggccggga cagacgtggc    1200

cgggaccctg agatgggggg aaagccgaga aggaagaacc ctcaggaagg cctgtacaat    1260

gaactgcaga aagataagat ggcggaggcc tacagtgaga ttgggatgaa aggcgagcgc    1320

cggaggggca aggggcacga tggcctttac cagggtctca gtacagccac caaggacacc    1380
```

```
tacgacgccc ttcacatgca ggccctgccc cctcgcgcct ctagagccga gggcagaggc   1440

agcctgctga catgtggcga cgtggaagag aacccaggcc ccatgaccac ccccagaaac   1500

agcgtgaacg gcaccttccc cgccgagcct atgaagggcc ctatcgccat gcagagcggc   1560

cccaagcccc tgttcagacg gatgtctagc ctcgtgggcc ctacccagag cttcttcatg   1620

agagagagca agaccctggg cgccgtgcag atcatgaacg gcctgttcca cattgccctg   1680

ggcggcctgc tgatgatccc tgccggaatc tacgcccccca tctgcgtgac cgtgtggtat  1740

cctctgtggg gcggcatcat gtacatcatc agcggcagcc tgctggccgc caccgagaag   1800

aacagcagaa agtgcctcgt gaagggcaag atgatcatga atagcctgag cctgttcgcc   1860

gccatctccg gcatgatcct gagcatcatg gatatcctga atatcaagat cagccacttc   1920

ctgaagatgg aaagcctgaa cttcatccgg gcccacaccc cctacatcaa catctacaac   1980

tgcgagcccg ccaaccccag cgagaagaat agccccagca cccagtactg ctactctatc   2040

cagtccctgt tcctgggcat cctgagcgtg atgctgatct tcgcattttt tcaagagctc   2100

gtgatcgccg gcatcgtgga aaacgagtgg aagcggacct gcagccggcc caagagcaac   2160

atcgtgctgc tgagcgccga ggaaaagaaa gagcagacca tcgagatcaa agaggaagtc   2220

gtgggcctga ccgagacaag ctcccagccc aagaacgaag aggacattga gatcatccca   2280

atccaggaag aagaggaaga ggaaaccgag actaacttcc ccgagccccc ccaggaccag   2340

gaaagcagcc ccatcgagaa cgacagcagc ccctga                             2376
```

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 25

```
Met Ala Leu Pro Val Thr Ala Leu Leu Leu Pro Leu Ala Leu Leu Leu
1               5                   10                  15

His Ala Ala Arg Pro
            20
```

<210> SEQ ID NO 26
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 26

```
atggccttac cagtgaccgc cttgctcctg ccgctggcct tgctgctcca cgccgccagg     60

ccg                                                                    63
```

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

```
Met Asp Trp Ile Trp Arg Ile Leu Phe Leu Val Gly Ala Ala Thr Gly
1               5                   10                  15
```

Ala His Ser

<210> SEQ ID NO 28
<211> LENGTH: 57
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 28
atggactgga tctggcgcat cctgtttctc gtgggagccg ccacaggcgc ccattct 57

<210> SEQ ID NO 29
<211> LENGTH: 238
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Met Asn Trp Val Lys Gln Arg Pro Asp Gln Gly Leu Glu Trp Ile
        35                  40                  45

Gly Arg Ile Asp Pro Tyr Asp Ser Glu Thr His Tyr Asn Gln Lys Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Asn Trp Asp Asp Tyr Trp Gly Gln Gly Thr Thr Leu Thr
            100                 105                 110

Val Ser Ser Gly Gly Gly Gly Ser Gly Gly Gly Gly Ser Gly Gly Gly
        115                 120                 125

Gly Ser Asp Val Gln Ile Thr Gln Ser Pro Ser Tyr Leu Ala Ala Ser
    130                 135                 140

Pro Gly Glu Thr Ile Thr Ile Asn Cys Arg Ala Ser Lys Ser Ile Ser
145                 150                 155                 160

Lys Asp Leu Ala Trp Tyr Gln Glu Lys Pro Gly Lys Thr Asn Lys Leu
                165                 170                 175

Leu Ile Tyr Ser Gly Ser Thr Leu Gln Ser Gly Ile Pro Ser Arg Phe
            180                 185                 190

Ser Gly Ser Gly Ser Gly Thr Asp Phe Thr Leu Thr Ile Ser Ser Leu
        195                 200                 205

Glu Pro Glu Asp Phe Ala Met Tyr Tyr Cys Gln Gln His Asn Lys Tyr
    210                 215                 220

Pro Tyr Thr Phe Gly Gly Gly Thr Lys Leu Glu Ile Lys Ser
225                 230                 235
```

<210> SEQ ID NO 30
<211> LENGTH: 714
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
caggtgcagc tgcagcagcc tggcgctgaa ctcgtgcggc caggcgcttc tgtgaagctg     60

agctgtaaag ccagcggcta caccttcacc agctactgga tgaactgggt caagcagcgg    120

cccgaccagg gcctggaatg gatcggaaga atcgacccct acgacagcga gacacactac    180

aaccagaagt tcaaggacaa ggccatcctg accgtggaca agagcagcag caccgcctac    240

atgcagctgt ccagcctgac cagcgaggac agcgccgtgt actactgcgc cagaggcaac    300

tgggacgact actggggcca gggcacaacc ctgacagtgt ctagcggagg cggaggatca    360

ggcggcggag gaagtggggg aggcggatct gatgtgcaga ttacccagtc ccccagctac    420

ctggccgcct ctcctggcga gacaatcacc atcaactgcc gggccagcaa gagcatctcc    480

aaggacctgg cctggtatca ggaaaagccc ggcaagacca acaagctgct gatctacagc    540

ggctccaccc tgcagtccgg catccccagc agattttccg gcagcggctc tggcaccgac    600

ttcaccctga ccatcagctc cctggaaccc gaggactttg ccatgtacta ttgccagcag    660

cacaacaagt acccttacac cttcggcgga ggcaccaagc tggaaatcaa gagc          714
```

<210> SEQ ID NO 31
<211> LENGTH: 244
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 31

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ile Phe Thr Asn Tyr
            20                  25                  30

Gly Met Asn Trp Val Lys Gln Ala Pro Gly Lys Ser Phe Lys Trp Met
        35                  40                  45

Gly Trp Ile Asn Thr Tyr Thr Gly Glu Ser Thr Tyr Ser Ala Asp Phe
    50                  55                  60

Lys Gly Arg Phe Ala Phe Ser Leu Glu Thr Ser Ala Ser Thr Ala Tyr
65                  70                  75                  80

Leu His Ile Asn Asp Leu Lys Asn Glu Asp Thr Ala Thr Tyr Phe Cys
                85                  90                  95

Ala Arg Ser Gly Gly Tyr Asp Pro Met Asp Tyr Trp Gly Gln Gly Thr
            100                 105                 110

Ser Val Thr Val Ser Ser Gly Gly Gly Gly Ser Gly Gly Gly Gly Ser
        115                 120                 125

Gly Gly Gly Gly Ser Asp Ile Val Leu Thr Gln Ser Pro Ala Ser Leu
    130                 135                 140

Ala Val Ser Leu Gly Gln Arg Ala Thr Ile Ser Cys Arg Ala Ser Glu
145                 150                 155                 160

Ser Val Asp Asn Tyr Gly Asn Thr Phe Met His Trp Tyr Gln Gln Lys
                165                 170                 175

Pro Gly Gln Pro Pro Lys Leu Leu Ile Tyr Arg Ala Ser Asn Leu Glu
            180                 185                 190

Ser Gly Ile Pro Ala Arg Phe Ser Gly Ser Gly Ser Arg Thr Asp Phe
        195                 200                 205

Thr Leu Thr Ile Asn Pro Val Glu Ala Asp Asp Val Ala Thr Tyr Tyr
```

```
    210                 215                 220

Cys Gln Gln Ser Asn Glu Asp Pro Pro Thr Phe Gly Ala Gly Thr Lys
225                 230                 235                 240

Leu Glu Leu Lys


<210> SEQ ID NO 32
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

cagattcagc tggtgcagtc tggccccgag ctgaagaaac ccggcgagac agtgaagatc      60

agctgcaagg ccagcggcta catcttcacc aactacggca tgaactgggt caagcaggcc     120

cctggcaaga gcttcaagtg gatgggctgg atcaacacct acaccggcga gagcacctac     180

agcgccgact tcaagggcag attcgccttc agcctggaaa ccagcgccag caccgcctac     240

ctgcacatca acgacctgaa gaacgaggac accgccacct acttttgcgc cagaagcggc     300

ggctacgacc ctatggatta ttggggccag ggcaccagcg tgaccgtgtc tagcggaggc     360

ggaggaagtg gcggcggagg atctgggggga ggcggatctg atatcgtgct gacccagagc     420

cctgccagcc tggctgtgtc tctgggacag agagccacca tcagctgtcg ggccagcgag     480

agcgtggaca attacggcaa caccttcatg cactggtatc agcagaagcc cggccagccc     540

cccaagctgc tgatctacag agccagcaac ctggaaagcg gcatccccgc cagattttcc     600

ggcagcggca gcagaaccga cttcaccctg accatcaacc ccgtggaagc cgacgacgtg     660

gccacctatt actgccagca gagcaacgag gaccccccta cctttggagc cggcaccaag     720

ctggaactga ag                                                         732


<210> SEQ ID NO 33
<211> LENGTH: 248
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Ser Asn Tyr
            20                  25                  30

Leu Met Asn Trp Val Lys Gln Arg Pro Glu Gln Asp Leu Asp Trp Ile
        35                  40                  45

Gly Arg Ile Asp Pro Tyr Asp Gly Asp Ile Asp Tyr Asn Gln Asn Phe
    50                  55                  60

Lys Asp Lys Ala Ile Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Tyr Gly Thr Ala Tyr Gly Val Asp Tyr Trp Gly Gln Gly
            100                 105                 110

Thr Ser Val Thr Val Ser Ser Ala Lys Thr Thr Pro Pro Lys Leu Glu
        115                 120                 125
```

```
Glu Gly Glu Phe Ser Glu Ala Arg Val Asp Ile Val Leu Thr Gln Ser
    130                 135                 140

Pro Ala Ser Leu Ala Val Ser Leu Gly Gln Arg Ala Thr Ile Ser Cys
145                 150                 155                 160

Arg Ala Ser Glu Ser Val Asp Asn Tyr Gly Ile Ser Phe Met Asn Trp
                165                 170                 175

Phe Gln Gln Lys Pro Gly Gln Pro Pro Lys Leu Leu Ile Tyr Ala Ala
            180                 185                 190

Ser Arg Gln Gly Ser Gly Val Pro Ala Arg Phe Ser Gly Ser Gly Ser
        195                 200                 205

Gly Thr Asp Phe Ser Leu Asn Ile His Pro Met Glu Glu Asp Asp Thr
    210                 215                 220

Ala Met Tyr Phe Cys Gln Gln Ser Lys Glu Val Pro Trp Thr Phe Gly
225                 230                 235                 240

Gly Gly Thr Lys Leu Glu Ile Lys
                245
```

```
<210> SEQ ID NO 34
<211> LENGTH: 744
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

caggtgcagc tgcagcagcc tggcgctgaa ctcgtgcggc caggcgcttc tgtgaagctg     60

agctgtaaag ccagcggcta caccttcagc aactacctga tgaactgggt caagcagcgg    120

cccgagcagg acctggattg gatcggcaga atcgacccct acgacggcga catcgactac    180

aaccagaact tcaaggacaa ggccatcctg accgtggaca agagcagcag caccgcctac    240

atgcagctgt ccagcctgac cagcgaggac agcgccgtgt actactgcgc cagaggctac    300

ggcacagcct acggcgtgga ctattggggc cagggcacaa gcgtgaccgt gtccagcgcc    360

aagaccaccc cccctaagct ggaagagggc gagttctccg aggcccgggt ggacattgtg    420

ctgacacagt ctccagccag cctggccgtg tccctgggac agagagccac catcagctgt    480

agggccagcg agagcgtgga caactacggc atcagcttca tgaattggtt ccagcagaag    540

cccggccagc cccccaagct gctgatctat gccgccagca gacagggcag cggagtgcct    600

gccagatttt ctggcagcgg ctccggcacc gacttcagcc tgaacatcca ccctatggaa    660

gaggacgaca ccgccatgta cttttgccag cagagcaaag aggtgccctg gacctttggc    720

ggaggcacca agctggaaat caag                                           744


<210> SEQ ID NO 35
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
```

```
        35                  40                  45

Trp Ala Pro Leu Ala Gly Thr Cys Gly Val Leu Leu Leu Ser Leu Val
    50                  55                  60

Ile Thr
65


<210> SEQ ID NO 36
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36

accacgacgc cagcgccgcg accaccaacg ccggcgccca ccatcgcgtc gcagcccctg     60

tccctgcgcc cagaggcgtg ccggccagcg gcggggggcg cagtgcacac gagggggctg    120

gacttcgcct gtgatatcta catctgggcg cccttggccg ggacttgtgg ggtccttctc    180

ctgtcactgg ttatcacc                                                   198


<210> SEQ ID NO 37
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45


<210> SEQ ID NO 38
<211> LENGTH: 135
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

accacgacgc cagcgccgcg accaccaacg ccggcgccca ccatcgcgtc gcagcccctg     60

tccctgcgcc cagaggcgtg ccggccagcg gcggggggcg cagtgcacac gagggggctg    120

gacttcgcct gtgat                                                      135


<210> SEQ ID NO 39
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ile Tyr Ile Trp Ala Pro Leu Ala Gly Thr Cys Gly Val Leu Leu Leu
1               5                   10                  15

Ser Leu Val Ile Thr
```

20

<210> SEQ ID NO 40
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
atctacatct gggcgccctt ggccgggact tgtggggtcc ttctcctgtc actggttatc 60
acc 63

<210> SEQ ID NO 41
<211> LENGTH: 66
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 41

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro Phe Trp Val Leu Val Val Val Gly Gly
35 40 45

Val Leu Ala Cys Tyr Ser Leu Leu Val Thr Val Ala Phe Ile Ile Phe
50 55 60

Trp Val
65

<210> SEQ ID NO 42
<211> LENGTH: 198
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42
atcgaagtga tgtacccgcc tccttacctg gacaacgaga agtccaacgg caccatcatc 60
cacgtgaagg gaaagcacct gtgtccttct ccactgttcc ccggacctag caagcctttc 120
tgggtgctcg ttgttgttgg cggcgtgctg gcctgttaca gcctgctggt taccgtggcc 180
ttcatcatct ttgggtc 198

<210> SEQ ID NO 43
<211> LENGTH: 39
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro
        35

<210> SEQ ID NO 44
<211> LENGTH: 117
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
atcgaagtga tgtacccgcc tccttacctg gacaacgaga agtccaacgg caccatcatc     60
cacgtgaagg gaaagcacct gtgtccttct ccactgttcc ccggacctag caagcct       117

<210> SEQ ID NO 45
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 46
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttctgggtgc tcgttgttgt tggcggcgtg ctggcctgtt acagcctgct ggttaccgtg     60
gccttcatca tcttttgggt c                                               81

<210> SEQ ID NO 47
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttttgggtgc tggtggtggt tggtggagtc ctggcttgct atagcttgct agtaacagtg     60
gcctttatta ttttctgggt g                                               81

<210> SEQ ID NO 48
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Glu Pro Lys Ser Cys Asp Lys Thr His Thr Cys Pro Pro Cys Pro
1               5                   10                  15

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
gagcccaaat cttgtgacaa aactcacaca tgcccaccgt gcccg 45

<210> SEQ ID NO 50
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Asp Leu Glu Pro Lys Ser Cys Asp Lys Thr His Thr Cys Pro Pro Cys
1 5 10 15

Pro Asp Pro Lys
20

<210> SEQ ID NO 51
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 51
gatctcgagc ccaaatcttg tgacaaaact cacacatgcc caccgtgccc ggatcccaaa 60

<210> SEQ ID NO 52
<211> LENGTH: 42
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 53
<211> LENGTH: 126
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 54
<211> LENGTH: 41
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 55
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
cgaagcaagc ggagccggct gctgcacagc gactacatga acatgacccc tagacggccc     60

ggaccaacca gaaagcacta ccagccttac gctcctccta gagatttcgc cgcctaccgg    120

tcc                                                                  123
```

<210> SEQ ID NO 56
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 56

```
cggtccaaga gaagcagact gctgcacagc gactacatga acatgacccc tagacggccc     60

ggacctacca gaaagcacta ccagccttac gctcctccta gagatttcgc cgcctaccgg    120

tcc                                                                  123
```

<210> SEQ ID NO 57
<211> LENGTH: 123
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123
```

<210> SEQ ID NO 58
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 59
<211> LENGTH: 339
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 59
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgctaa 339

<210> SEQ ID NO 60
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

Arg Val Lys Phe Ser Arg Ser Ala Asp Ala Pro Ala Tyr Gln Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Arg Arg Gly Arg Asp Pro
35 40 45

Glu Met Gly Gly Lys Pro Arg Arg Lys Asn Pro Gln Glu Gly Leu Tyr
50 55 60

Asn Glu Leu Gln Lys Asp Lys Met Ala Glu Ala Tyr Ser Glu Ile Gly
65 70 75 80

Met Lys Gly Glu Arg Arg Arg Gly Lys Gly His Asp Gly Leu Tyr Gln
85 90 95

Gly Leu Ser Thr Ala Thr Lys Asp Thr Tyr Asp Ala Leu His Met Gln
100 105 110

```
Ala Leu Pro Pro Arg
        115


<210> SEQ ID NO 61
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

agagtgaagt tcagcaggag cgcagacgcc cccgcgtacc agcagggcca gaaccagctc     60

tataacgagc tcaatctagg acgaagagag gagtacgatg ttttggacaa gagacgtggc    120

cgggacagac gtggccggga ccctgagatg gggggaaagc cgagaaggaa gaaccctcag    180

gaaggcctgt acaatgaact gcagaaagat aagatggcgg aggcctacag tgagattggg    240

atgaaaggcg agcgccggag gggcaagggg cacgatggcc tttaccaggg tctcagtaca    300

gccaccaagg acacctacga cgcccttcac atgcaggccc tgccccctcg c             351


<210> SEQ ID NO 62
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220
```

```
Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295


<210> SEQ ID NO 63
<211> LENGTH: 891
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

atgaccacac ctcggaacag cgtgaacggc acatttcccg ccgagcctat gaagggccct     60

atcgccatgc agtctggccc caagcctctg ttcagacgga tgtctagcct cgtgggcccc    120

acacagagct tttcatgag agagagcaag accctgggcg ccgtgcagat catgaacggc    180

ctgtttcaca ttgccctcgg cggcctgctg atgatccctg ccggaatcta tgcccctatc    240

tgcgtgaccg tgtggtatcc tctgtggggc ggcatcatgt acatcatctc tggatctctg    300

ctggccgcca ccgagaagaa cagcagaaag tgtctggtca agggcaagat gatcatgaat    360

agcctgagcc tgttcgccgc catcagcggc atgatcctga gcatcatgga tatcctgaat    420

atcaagatca gccacttcct gaagatggaa agcctgaact tcatcagggc ccacacacct    480

tacatcaaca tctacaactg cgagcccgcc aatcctagcg agaagaatag ccccagcaca    540

cagtactgct actctatcca gagcctgttt ctgggcatcc tgagcgtgat gctgatcttc    600

gcattcttcc aagagctggt tatcgccggc atcgtggaaa acgagtggaa gcggacctgc    660

agcagaccca agagcaacat cgtgctgctg agcgccgagg aaaagaaaga gcagaccatc    720

gagatcaaag aggaagtcgt cggcctgacc gagacaagca gccagcctaa gaacgaagag    780

gacattgaga tcatccccat ccaagaagag gaagaagaag agactgagac aaacttcccc    840

gagcctcctc aggaccaaga gagcagcccc attgagaacg atagcagccc t             891


<210> SEQ ID NO 64
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 64

atgaccaccc ccagaaacag cgtgaacggc accttccccg ccgagcctat gaagggccct     60

atcgccatgc agagcggccc caagcccctg ttcagacgga tgtctagcct cgtgggccct    120

acccagagct tcttcatgag agagagcaag accctgggcg ccgtgcagat catgaacggc    180

ctgttccaca ttgccctggg cggcctgctg atgatccctg ccggaatcta cgcccccatc    240

tgcgtgaccg tgtggtatcc tctgtggggc ggcatcatgt acatcatcag cggcagcctg    300

ctggccgcca ccgagaagaa cagcagaaag tgcctcgtga agggcaagat gatcatgaat    360
```

```
agcctgagcc tgttcgccgc catctccggc atgatcctga gcatcatgga tatcctgaat    420

atcaagatca gccacttcct gaagatggaa agcctgaact tcatccgggc ccacaccccc    480

tacatcaaca tctacaactg cgagcccgcc aaccccagcg agaagaatag ccccagcacc    540

cagtactgct actctatcca gtccctgttc ctgggcatcc tgagcgtgat gctgatcttc    600

gcatttttc aagagctcgt gatcgccggc atcgtggaaa acgagtggaa gcggacctgc    660

agccggccca agagcaacat cgtgctgctg agcgccgagg aaaagaaaga gcagaccatc    720

gagatcaaag aggaagtcgt gggcctgacc gagacaagct cccagcccaa gaacgaagag    780

gacattgaga tcatcccaat ccaggaagaa gaggaagagg aaaccgagac taacttcccc    840

gagcccccc aggaccagga aagcagcccc atcgagaacg acagcagccc ctga          894


<210> SEQ ID NO 65
<211> LENGTH: 18
<212> TYPE: PRT
<213> ORGANISM: Thosea asigna virus

<400> SEQUENCE: 65

Glu Gly Arg Gly Ser Leu Leu Thr Cys Gly Asp Val Glu Glu Asn Pro
1               5                   10                  15

Gly Pro


<210> SEQ ID NO 66
<211> LENGTH: 54
<212> TYPE: DNA
<213> ORGANISM: Thosea asigna virus

<400> SEQUENCE: 66

gaaggcagag gatcactgct gacatgcggc gacgtggaag agaaccctgg accc           54


<210> SEQ ID NO 67
<211> LENGTH: 54
<212> TYPE: DNA
<213> ORGANISM: Thosea asigna virus

<400> SEQUENCE: 67

gagggcagag gcagcctgct gacatgtggc gacgtggaag agaacccagg cccc           54


<210> SEQ ID NO 68
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ser Gly Glu Gly Arg Gly Ser Leu Leu Thr Cys Gly Asp Val Glu
1               5                   10                  15

Glu Asn Pro Gly Pro
            20


<210> SEQ ID NO 69
<211> LENGTH: 63
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69
```

```
Gly Ser Gly Ser Arg Val Thr Glu Leu Leu Tyr Arg Met Lys Arg Ala
1               5                   10                  15

Glu Thr Tyr Cys Pro Arg Pro Leu Leu Ala Ile His Pro Thr Glu Ala
            20                  25                  30

Arg His Lys Gln Lys Ile Val Ala Pro Val Lys Gln Leu Leu Asn Phe
        35                  40                  45

Asp Leu Leu Lys Leu Ala Gly Asp Val Glu Ser Asn Pro Gly Pro
    50                  55                  60


<210> SEQ ID NO 70
<211> LENGTH: 19
<212> TYPE: PRT
<213> ORGANISM: Amphimedon queenslandica

<400> SEQUENCE: 70

Leu Leu Cys Phe Leu Leu Leu Leu Leu Ser Gly Asp Val Glu Leu Asn
1               5                   10                  15

Pro Gly Pro


<210> SEQ ID NO 71
<211> LENGTH: 20
<212> TYPE: PRT
<213> ORGANISM: Amphimedon queenslandica

<400> SEQUENCE: 71

His His Phe Met Phe Leu Leu Leu Leu Leu Ala Gly Asp Ile Glu Leu
1               5                   10                  15

Asn Pro Gly Pro
            20


<210> SEQ ID NO 72
<211> LENGTH: 20
<212> TYPE: PRT
<213> ORGANISM: Saccoglossus kowalevskii

<400> SEQUENCE: 72

Trp Phe Leu Val Leu Leu Ser Phe Ile Leu Ser Gly Asp Ile Glu Val
1               5                   10                  15

Asn Pro Gly Pro
            20


<210> SEQ ID NO 73
<211> LENGTH: 20
<212> TYPE: PRT
<213> ORGANISM: Branchiostoma floridae

<400> SEQUENCE: 73

Lys Asn Cys Ala Met Tyr Met Leu Leu Leu Ser Gly Asp Val Glu Thr
1               5                   10                  15

Asn Pro Gly Pro
            20


<210> SEQ ID NO 74
<211> LENGTH: 20
<212> TYPE: PRT
<213> ORGANISM: Branchiostoma floridae

<400> SEQUENCE: 74

Met Val Ile Ser Gln Leu Met Leu Lys Leu Ala Gly Asp Val Glu Glu
1               5                   10                  15
```

```
Asn Pro Gly Pro
            20


<210> SEQ ID NO 75
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Ser Gly Ala Thr Asn Phe Ser Leu Leu Lys Gln Ala Gly Asp Val
1               5                   10                  15

Glu Glu Asn Pro Gly Pro
            20


<210> SEQ ID NO 76
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Ser Gly Gln Cys Thr Asn Tyr Ala Leu Leu Lys Leu Ala Gly Asp
1               5                   10                  15

Val Glu Ser Asn Pro Gly Pro
            20


<210> SEQ ID NO 77
<211> LENGTH: 8
<212> TYPE: PRT
<213> ORGANISM: Unknown
<220> FEATURE:
<223> OTHER INFORMATION: Description of Unknown:
      2A consensus sequence
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (4)..(4)
<223> OTHER INFORMATION: Any amino acid

<400> SEQUENCE: 77

Asp Xaa Glu Xaa Asn Pro Gly Pro
1               5


<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ala Ser Arg Ala
1


<210> SEQ ID NO 79
<211> LENGTH: 12
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 79
gcctccagag cc 12

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
acttgaaagc gaaagggaaa c 21

<210> SEQ ID NO 81
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cacccatctc tctccttcta gcc 23

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 82
agctctctcg acgcaggact cggc 24

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gcggctgtct ccacaagt 18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
gatttggacc tgcgagcg 18

<210> SEQ ID NO 85
<211> LENGTH: 16
<212> TYPE: DNA
<213> ORGANISM: Artificial Sequence -continued

```
<220> FEATURE:
<223> OTHER INFORMATION: Description of Artificial Sequence: Synthetic
      probe

<400> SEQUENCE: 85

ctgacctgaa ggctct                                                      16
```

CHIMERIC ANTIGEN RECEPTORS WITH CD20 SAFETY SWITCH

CROSS-REFERENCE TO RELATED APPLICATIONS

This application is a National Stage Application of International Application No. PCT/US20/27719, filed Apr. 10, 2020 which claims priority to U.S. Provisional Application No. 62/833,337, filed Apr. 12, 2019, all of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Apr. 3, 2020, is named 243734_000131_SL.TXT and is 135,883 bytes in size.

FIELD OF THE INVENTION

The application relates to chimeric antigen receptors (CARs), particularly CARs with improved antitumor properties and/or regulatable features, and their uses in cancer immunotherapy (e.g., adoptive cell therapy).

BACKGROUND

Treatment of acute myeloid leukemia (AML) is challenging due to its high treatment related morbidity and mortality, as well as a high relapse rate. In particular, pediatric AML is a cancer with high relapse rate and poor prognosis. Adoptive transfer of T cells expressing chimeric antigen receptors (CAR T cells) has the potential to improve outcomes. Finding the best targetable antigen for AML has been a long proven challenging due to the high degree of antigen expression overlap between AML blasts and normal hematopoietic cells (HPCs) or mature neutrophils.

CD123 is overexpressed on a large proportion of malignant myeloid blasts, with restricted expression on normal cells. In fact, CAR T cells targeting the AML antigen CD123 have shown promise in preclinical models, and early Phase clinical testing is in progress. CD123 CAR T-cells need to be able to expand and kill CD123$^+$ target cells in an antigen dependent manner, while bypassing a highly immunosuppressive microenvironment. Optimization of current CAR T therapies is needed. Moreover, CD123 is expressed at low levels in normal hematopoietic progenitor cells, raising safety concerns. CD123 specific CAR T-cells have the potential to cause myelotoxicity. Strategies to reduce treatment-related complications of current CAR-T therapies are also needed.

Thus, there exists a need for improved immunotherapeutic strategies against AML. This present invention provides a solution to address this problem.

SUMMARY OF THE INVENTION

The present invention discloses, in various aspects, chimeric antigen receptors (CARs), particularly CARs that have enhanced antitumor properties and/or can be regulated by safety switches, as well as related polynucleotides, vectors, and cell compositions comprising the same. Further disclosed are compositions (e.g., pharmaceutical compositions) comprising the polypeptides, polynucleotides, vectors, or cell compositions, and methods of using such compositions in treating a cancer in a subject.

In one aspect provided herein is a polynucleotide encoding a chimeric antigen receptor (CAR) comprising: (a) a leader sequence, (b) an extracellular target-binding domain comprising a CD123-binding moiety, (c) a hinge domain derived from CD8α or CD28, (d) a transmembrane domain derived from CD8α or CD28, and (e) a cytoplasmic domain comprising (i) one or more costimulatory domains derived from CD28 and/or 4-1BB, and (ii) a signaling domain derived from CD3ζ.

In some embodiments, the CD123-binding moiety is an anti-CD123 single chain variable fragment (scFv). In some embodiments, the anti-CD123 scFv is derived from antibody 26292 (scFV (292)).

In some embodiments, the polynucleotide encoding a CAR comprises (a) a leader derived from CD8α, (b) an extracellular target-binding domain comprising scFV (292), (c) a hinge domain derived from CD8α, (d) a transmembrane domain derived from CD8α, and (e) a cytoplasmic domain comprising (i) a costimulatory domain derived from 4-1BB, and (ii) a signaling domain derived from CD3ζ.

In some embodiments, the polynucleotide encoding a CAR comprises (a) a leader sequence derived from CD8α, (b) an extracellular target-binding domain comprising scFV (292), (c) a hinge domain derived from CD8α, (d) a transmembrane domain derived from CD8α, and (e) a cytoplasmic domain comprising (i) a costimulatory domain derived from CD28, and (ii) a signaling domain derived from CD3ζ.

In some embodiments, the polynucleotide encoding a CAR comprises (a) a leader sequence derived from CD8α, (b) an extracellular target-binding domain comprising scFV (292), (c) a hinge domain derived from CD28, (d) a transmembrane domain derived from CD28, and (e) a cytoplasmic domain comprising (i) a costimulatory domain derived from CD28, a costimulatory domain derived from 4-1BB, and (ii) a signaling domain derived from CD3ζ.

In some embodiments, the polynucleotide encoding a CAR comprises (a) a leader sequence derived from CD8α(b) an extracellular target-binding domain comprising scFV (292), (c) a hinge domain derived from CD28, (d) a transmembrane domain derived from CD28, and (e) a cytoplasmic domain comprising (i) a costimulatory domain derived from CD28 and (ii) a signaling domain derived from CD3ζ.

In some embodiments, scFV (292) comprises the amino acid sequence set forth in SEQ ID NO: 29, or an amino acid sequence having at least 80% identity thereof. In some embodiments, the nucleotide sequence encoding scFV (292) comprises the nucleotide sequence set forth in SEQ ID NO: 30, or a nucleotide sequence having at least 80% identity thereof.

In some embodiments, the anti-CD123 scFv is derived from antibody 26716 (scFV (716)).

In some embodiments, the polynucleotide encoding a CAR comprises (a) a leader sequence derived from CD8α, (b) an extracellular target-binding domain comprising scFV (716), (c) a hinge domain derived from CD8α, (d) a transmembrane domain derived from CD8α, and (e) a cytoplasmic domain comprising (i) a costimulatory domain derived from CD28 and (ii) a signaling domain derived from CD3ζ.

In some embodiments, scFV (716) comprises the amino acid sequence set forth in SEQ ID NO: 31, or an amino acid sequence having at least 80% identity thereof. In some embodiments, the nucleotide sequence encoding scFV (716)

comprises the nucleotide sequence set forth in SEQ ID NO: 32, or a nucleotide sequence having at least 80% identity thereof.

In some embodiments, the leader sequence is derived from CD8α. In some embodiments, the leader sequence derived from CD8α comprises the amino acid sequence of SEQ ID NO: 25, or an amino acid sequence having at least 80% identity thereof. In some embodiments, the nucleotide sequence encoding the leader sequence derived from CD8α comprises the sequence of SEQ ID NO: 26, or a nucleotide sequence having at least 80% identity thereof.

In some embodiments, the hinge domain derived from CD8α comprises the amino acid sequence of SEQ ID NO: 37, or an amino acid sequence having at least 80% identity thereof. In some embodiments, the nucleotide sequence encoding the hinge domain derived from CD8α comprises the sequence of SEQ ID NO: 38, or a nucleotide sequence having at least 80% identity thereof.

In some embodiments, the hinge domain derived from CD28 comprises the amino acid sequence of SEQ ID NO: 43, or an amino acid sequence having at least 80% identity thereof. In some embodiments, the nucleotide sequence encoding the hinge domain derived from CD28 comprises the sequence of SEQ ID NO: 44, or a nucleotide sequence having at least 80% identity thereof.

In some embodiments, the transmembrane domain derived from CD8α comprises the amino acid sequence of SEQ ID NO: 39, or an amino acid sequence having at least 80% identity thereof. In some embodiments, the nucleotide sequence encoding the transmembrane domain derived from CD8α comprises the sequence of SEQ ID NO: 40, or a nucleotide sequence having at least 80% identity thereof.

In some embodiments, the transmembrane domain derived from CD28 comprises the amino acid sequence of SEQ ID NO: 45, or an amino acid sequence having at least 80% identity thereof. In some embodiments, the nucleotide sequence encoding the transmembrane domain derived from CD28 comprises the sequence of SEQ ID NO: 46, or a nucleotide sequence having at least 80% identity thereof.

In some embodiments, the costimulatory domain derived from CD28 comprises the amino acid sequence of SEQ ID NO: 54, or an amino acid sequence having at least 80% identity thereof. In some embodiments, the nucleotide sequence encoding the costimulatory domain derived from CD28 comprises the sequence of SEQ ID NO: 55, 56, or 57, or a nucleotide sequence having at least 80% identity thereof.

In some embodiments, the costimulatory domain derived from 4-1BB comprises the amino acid sequence of SEQ ID NO: 52, or an amino acid sequence having at least 80% identity thereof. In some embodiments, the nucleotide sequence encoding the costimulatory domain derived from 4-1BB comprises the sequence of SEQ ID NO: 53, or a nucleotide sequence having at least 80% identity thereof.

In some embodiments, the signaling domain derived from CD3ζ comprises the amino acid sequence of SEQ ID NO: 58 or 60, or an amino acid sequence having at least 80% identity thereof. In some embodiments, the nucleotide sequence encoding the signaling domain derived from CD3ζ comprises the sequence of SEQ ID NO: 59 or 61, or a nucleotide sequence having at least 80% identity thereof.

In some embodiments, the CAR comprises the amino acid sequence of SEQ ID NO: 1, or an amino acid sequence having at least 80% identity thereof. In some embodiments, the polynucleotide encoding the CAR comprises the sequence of SEQ ID NO: 2, or a nucleotide sequence having at least 80% identity thereof.

In some embodiments, the CAR comprises the amino acid sequence of SEQ ID NO: 3, or an amino acid sequence having at least 80% identity thereof. In some embodiments, the polynucleotide encoding the CAR comprises the sequence of SEQ ID NO: 4, or a nucleotide sequence having at least 80% identity thereof.

In some embodiments, the CAR comprises the amino acid sequence of SEQ ID NO: 5, or an amino acid sequence having at least 80% identity thereof. In some embodiments, the polynucleotide encoding the CAR comprises the sequence of SEQ ID NO: 6, or a nucleotide sequence having at least 80% identity thereof.

In some embodiments, the CAR comprises the amino acid sequence of SEQ ID NO: 7, or an amino acid sequence having at least 80% identity thereof. In some embodiments, the polynucleotide encoding the CAR comprises the sequence of SEQ ID NO: 8, or a nucleotide sequence having at least 80% identity thereof.

In some embodiments, the CAR comprises the amino acid sequence of SEQ ID NO: 9, or an amino acid sequence having at least 80% identity thereof. In some embodiments, the polynucleotide encoding the CAR comprises the sequence of SEQ ID NO: 10, or a nucleotide sequence having at least 80% identity thereof.

In another aspect provided herein is a chimeric antigen receptor (CAR) encoded by the polynucleotide described above.

In some embodiments, the polynucleotide further comprises a sequence encoding a CD20 polypeptide. In some embodiments, the polynucleotide comprises a sequence encoding an IL13Rα2-binding chimeric antigen receptor (CAR) and a sequence encoding a CD20 polypeptide. In some embodiments, the sequence encoding the IL13Rα2-binding CAR comprises (a) a leader sequence derived from human immunoglobulin heavy chain variable region, (b) an extracellular target-binding domain comprising scFV (SH2), (c) a hinge domain derived from IgG1, (d) a transmembrane domain derived from CD28, and (e) a cytoplasmic domain comprising (i) a costimulatory domain derived from CD28 and (ii) a signaling domain derived from CD3ζ. In some embodiments, the leader sequence derived from human immunoglobulin heavy chain variable region comprises the amino acid sequence of SEQ ID NO: 27, or an amino acid sequence having at least 80% identity thereof. In some embodiments, the nucleotide sequence encoding the leader sequence derived from human immunoglobulin heavy chain variable region comprises the sequence of SEQ ID NO: 28, or a nucleotide sequence having at least 80% identity thereof. In some embodiments, the scFV (SH2) comprises the amino acid sequence of SEQ ID NO: 33, or an amino acid sequence having at least 80% identity thereof. In some embodiments, the nucleotide sequence encoding the scFV (SH2) comprises the sequence of SEQ ID NO: 34, or a nucleotide sequence having at least 80% identity thereof. In some embodiments, the hinge domain derived from IgG1 comprises the amino acid sequence of SEQ ID NO: 48, or an amino acid sequence having at least 80% identity thereof. In some embodiments, the nucleotide sequence encoding the hinge domain derived from IgG1 comprises the sequence of SEQ ID NO: 49, or a nucleotide sequence having at least 80% identity thereof. In some embodiments, the transmembrane domain derived from CD28 comprises the amino acid sequence of SEQ ID NO: 45, or an amino acid sequence having at least 80% identity thereof. In some embodiments, the nucleotide sequence encoding the transmembrane domain derived from CD28 comprises the sequence of SEQ ID NO: 47, or a nucleotide sequence having at least 80% identity thereof. In some embodiments, the costimulatory domain derived from CD28 comprises the amino acid sequence of SEQ ID NO: 54, or an amino acid sequence having at least 80% identity thereof. In some embodiments, the nucleotide sequence encoding the costimulatory domain derived from CD28 comprises the sequence of SEQ ID NO: 57, or a nucleotide sequence having at least 80% identity thereof. In some embodiments, the signaling domain derived from CD3ζ comprises the amino acid sequence of SEQ ID NO: 60, or an amino acid sequence having at least 80% identity thereof. In some embodiments, the nucleotide sequence encoding the signaling domain derived from CD3ζ comprises the sequence of SEQ ID NO: 61, or a nucleotide sequence having at least 80% identity thereof. In some embodiments, the IL13Rα2-binding CAR comprises the amino acid sequence of SEQ ID NO: 11, or an amino acid sequence having at least 80% identity thereof. In some embodiments, polynucleotide encoding the IL13Rα2-binding CAR comprises the sequence of SEQ ID NO: 12, or a nucleotide sequence having at least 80% identity thereof.

In some embodiments, the CD20 polypeptide comprises the amino acid sequence of SEQ ID NO: 62, or an amino acid sequence having at least 80% identity thereof. In some embodiments, the sequence encoding a CD20 polypeptide comprises the nucleotide sequence of SEQ ID NO: 63 or 64, or a nucleotide sequence having at least 80% identity thereof.

In some embodiments, the sequence encoding the CD20 polypeptide is operably linked to the sequence encoding CAR via a sequence encoding a self-cleaving peptide or an Internal Ribosome Entry Site (IRES). In some embodiments, the self-cleaving peptide is a 2A peptide. In some embodiments, the 2A peptide is a T2A, P2A, E2A, or F2A peptide. In some embodiments, the self-cleaving 2A peptide comprises the amino acid sequence of SEQ ID NO: 65, or an amino acid sequence having at least 80% identity thereof. In some embodiments, the sequence encoding the self-cleaving 2A peptide comprises the nucleotide sequence of SEQ ID NO: 66 or 67, or a nucleotide sequence having at least 80% identity thereof.

In some embodiments, the polynucleotide further comprises a linker sequence between the self-cleaving peptide and the CD20 polypeptide or the CAR. In some embodiments, the linker sequence encodes SEQ ID NO: 78, or an amino acid sequence having at least 80% identity thereof. In some embodiments, the linker sequence comprises the nucleotide sequence of SEQ ID NO: 79, or a nucleotide sequence having at least 80% identity thereof.

In some embodiments, the polynucleotide described herein is a DNA molecule.

In some embodiments, the polynucleotide described herein is an RNA molecule.

In another aspect provided herein is a recombinant vector comprising a polynucleotide described herein. In some embodiments, the vector is a viral vector. In some embodiments, the viral vector is a gamma retroviral vector or a lentiviral vector.

In another aspect provided herein is a pharmaceutical composition comprising a polynucleotide described herein or a recombinant vector described herein, and a pharmaceutically accepted carrier and/or excipient.

In another aspect provided herein is an isolated host cell comprising a polynucleotide described herein or a recombinant vector described herein. In another aspect provided herein is an isolated host cell comprising a CAR described herein.

In some embodiments, the isolated host cell further comprises a CD20 polypeptide. In some embodiments, the CD20 polypeptide comprises the amino acid sequence of SEQ ID NO: 62, or an amino acid sequence having at least 80% identity thereof.

In some embodiments, the host cell is an immune cell. In some embodiments, the immune cell is a T cell or a NK cell. In some embodiments, the T cell is selected from a CD8+ T cell, a CD4+ T cell, a cytotoxic T cell, an αβ T cell receptor (TCR) T cell, a natural killer T (NKT) cell, a γδ T cell, a memory T cell, a T-helper cell, and a regulatory T cell (Treg). In some embodiments, the host cell has been activated and/or expanded ex vivo.

In some embodiments, the host cell is an allogeneic cell. In some embodiments, the host cell is an autologous cell.

In some embodiments, the host cell is isolated from a subject having a cancer, wherein one or more cells of the cancer express CD123. In some embodiments, the CD123 expressing cancer is an acute myeloid leukemia (AML), an acute lymphoblastic leukemia (ALL), a blastic plasmacytoid dendritic neoplasm (BPCDN), or a hairy cell leukemia.

In some embodiments, the host cell is isolated from a subject having a cancer, wherein one or more cells of the cancer express IL13Rα2. In some embodiments, the IL13Rα2 expressing cancer is a brain cancer such as glioblastoma, a colon cancer, a renal cell carcinoma, a pancreatic cancer, a melanoma, a head and neck cancer, a mesothelioma, or an ovarian cancer.

In some embodiments, the host cell is derived from a blood, marrow, tissue, or a tumor sample.

In another aspect provided herein is a pharmaceutical composition comprising the host cell described herein and a pharmaceutically acceptable carrier and/or excipient.

In another aspect provided herein is a method for treating a cancer in a subject in need thereof, which comprises administering to the subject a therapeutically effective amount of the host cells or the pharmaceutical composition described herein. In some embodiments, the CAR on the host cell is a CD123-binding CAR and one or more cells of the cancer express CD123. In some embodiments, the CD123 expressing cancer is an acute myeloid leukemia (AML), an acute lymphoblastic leukemia (ALL), a blastic plasmacytoid dendritic neoplasm (BPCDN), or a hairy cell leukemia. In some embodiments, the CAR on the host cell is an IL13Rα2-binding CAR and one or more cells of the cancer express IL13Rα2. In some embodiments, the IL13Rα2 expressing cancer is a brain cancer such as glioblastoma, a colon cancer, a renal cell carcinoma, a pancreatic cancer, a melanoma, a head and neck cancer, a mesothelioma, or an ovarian cancer.

In some embodiments wherein the host cell comprises a CD20 polypeptide, the method further comprises administering an anti-CD20 antibody to the subject. The anti-CD20 antibody is administered in an amount effective for removal of the host cells from the subject. In some embodiments, the anti-CD20 antibody is administered in an amount effective for removal of more than 50% of the host cells from the subject. In some embodiments, the anti-CD20 antibody is selected from Rituximab, Ibritumomab tiuxetan, Tositumomab, Ofatumumab, Ocrelizumab, TRU-015, Veltuzumab, AME-133v, PRO131921, and Obinutuzumab. In some embodiments, the anti-CD20 antibody is Rituximab.

In another aspect provided herein is a method for treating a cancer in a subject in need thereof, which comprises (a) isolating T cells or NK cells from the subject or donor; (b) modifying the T cells or NK cells ex vivo with a polynucleotide or a recombinant vector described herein; (c) optionally, expanding and/or activating the modified T cells or NK cells before, after and/or during step (b); (d) introducing a therapeutically effective amount of the modified T cells or NK cells into the subject; and (e) in cases when the modified T cells or NK cells comprise CD20, optionally, administering an anti-CD20 antibody to the subject, wherein the anti-CD20 antibody is administered in respective amounts effective for removal of the modified T cells or NK cells from the subject.

In various embodiments of the methods described above, the subject is human.

In a further aspect provided herein is a method of generating an isolated host cell described above, which comprises genetically modifying the host cell with a polynucleotide or a recombinant vector described herein. In some embodiments, the vector is a non-viral vector and the genetic modification is conducted using PiggyBac- or Sleeping Beauty transposon systems, or gene editing with homology-directed repair (HDR). In some embodiments, the vector is a viral vector and the genetic modification is conducted by transduction using such vector. In some embodiments, the genetically modifying step is conducted ex vivo. In some embodiments, the method further comprises activation and/or expansion of the host cell ex vivo before, after and/or during the genetic modification.

These and other aspects of the present invention will be apparent to those of ordinary skill in the art in the following description, claims and drawings.

BRIEF DESCRIPTION OF THE DRAWINGS

(FIG. 1A) Schematic of the CD8α.41BBz viral vector. (FIG. 1B) Summary of the transduction process. (FIG. 1C) Viral Copy Number (VCN) of transduced CD123-CAR T cells and flow cytometry evaluation of CD123-CAR and CD20 expression in CD123-CAR T cells. There was a significant increase in VCN of transduced CD123-CAR T cells as compared to non-transduced (NT) T cells (n=5; p<0.01 ()), and significant higher expression of CD123-CAR and CD20 as compared to NT T cells (n=5; p<0.0001 ()). (FIG. 1D) NT or CD123 CAR T cells were incubated with rituximab (RTX) only or with rituximab+ complement. CD20+ cell number was determined by flow cytometry after 1 hour. (FIG. 1E) CD123-CAR and NT T cells were incubated with CD123+ (MOLM-13) and CD123− (K562) target cells at different effector to target (E:T) ratios. After 24 hours live tumor cells were determined by fluorescence-activated cell sorting (FACS) analysis. Assay was performed in triplicates. Significant tumor lysis of MOLM13 target cells was observed when incubated with CD123-CAR T cells vs NT T cells (n=3; p<0.0001 ()). (FIG. 1F) CD123+ MOLM13 (AML) cells expressing firefly luciferase (ffluc) were injected by intravenously (iv) via tail vein. On Day 5 mice received a single iv dose of CD123-CAR or CD19-CAR T cells. Mice that only received tumor cells served as controls (No T cells). AML progression was tracked by bioluminescence imaging. A significant reduction of MOLM13 cells was observed in mice that received CD123-CAR T cells vs mice that received no or CD19-CAR T cells (n=5; p<0.0001 (**)).

(FIG. 2A) IFNγ secretion was significantly increased in the presence of MOLM13 (n=5; p<0.0001 (**)). (FIG. 2B) CD8α.41BBz CAR T cells showed increased baseline IFNγ secretion in the presence of media and K562 (n=5; p<0.001 (*)).

FIGS. 3A-3M illustrate the generation and characterization of CD123 CAR constructs. (FIG. 3A) A panel of CD123 CAR constructs was designed using two different hinge/transmembrane (TM) domains and either encoding for CD28 and/or 41BBZ. (FIG. 3B) Vector copy number (VCN) was determined by digital drop PCR analysis utilizing primers within the lentiviral backbone (n=5; p=NS for all CAR T-cell construct comparisons). (FIG. 3C) Expression of CD20 safety switch was confirmed by flow cytometry (n=5, p=non-significant (NS) for CD20). (FIG. 3D) NT or CD123 CAR T cells were incubated with rituximab (RTX) only or with rituximab+ complement (RTX+C'). CD20+ cell number was determined by flow cytometry after 1 hour. (FIG. 3E) Expression of CD123 CAR was confirmed by flow cytometry (n=5, p<0.05 (*) for CD8α.CD28z construct for CD123 CAR expression). (FIGS. 3F-3H) Co-expression of CD123-CAR and CD20. Representative histograms and dot plots are shown. The inset bar graph shows the mean and standard deviation values for cells expressing CD123-CAR and CD20 (n=5, p=NS). (FIG. 3I and FIG. 3J) CD123-$CAR^{CD20}$ T-cells have similar transduction efficiencies. CD123-CAR CD20 T-cells were stained and analyzed by flow cytometry for % CAR and CD20 expression and mean fluorescence intensity (MFI); (FIG. 3I) CAR MFI (n=5, p=NS); (FIG. 3J) CD20 MFI (n=5, p=NS). (FIG. 3K) T cells transduced with CD28. CD28z-CARs express higher MFI levels of CARs than T cells transduced with CD8α.28z-CARs. Fold-change of CD28. CD28z- and CD8 a. CD28z-CAR T cells using the data presented in FIGS. 3B-3C, FIGS. 3F-3H and FIGS. 3I-3J (n=5; shaded area: 0.7- to 1.3-fold change). (FIG. 3L) Viability assessed using 7AAD/Annexin V staining showed no difference between constructs (n=5; p=NS). (FIG. 3M) Frequency of naïve (Naive: CCR7+ CD45RA+), effector memory (EM: CCR7− CD45RA−), central memory (CM:CCR7+ CD45RA−), and terminally differentiated (TD: CCR7− CD45RA+) T cells at day 8 (n=5).

FIGS. 4A-4I demonstrate that CD123-CAR T cell constructs had similar expansion and recognize CD123+ tumor cells in vitro. (FIG. 4A) All CD123-CAR constructs were able to expand in a similar way as mock (NT) and CD19-CAR T cells, after 8 days in culture. (FIG. 4B) Viability of the indicated populations was determined by AOPI exclusion (n=5; p=NS). (FIG. 4C) CD123-CAR and NT T cells were co-cultured with CD123+ (MOLM13) and CD123− (K562) target cells at 3:1 effector to target ratio. Tumor lysis was determined after 24 hours by flow cytometry. Assay was performed in triplicates. Significant tumor lysis of MOLM13 cells was observed for all CD123-CAR T cell constructs when compared to NT T cells (n=5; p<0.0001 (**)). (FIG. 4D) CD4:CD8 ratio distribution as assessed by flow cytometry. (FIG. 4E) T-cell immunophenotype (T-cell subsets: naïve CCR7+CD45RO−; central memory (CM) CCR7+CD45RO+; terminally differentiated (TD) CCR7-CD45RO−; effector memory (EM) CCR7-CD45RO+) (n=5). (FIGS. 4F-4H) Evaluation of CD27, PD1 and TIM3 expression using flow cytometry assay. (FIG. 4**I) CD4, CD8, Tim3, and PD1 expression (n=5; p=NS among CD123-CAR T-cell groups).

(K562) target cells or media. (FIG. 5A) All CD123 CAR constructs had significantly higher IFNγ secretion in the presence of CD123+ tumor cells when compared to mock treated T cells (n=5; p<0.0001 (**)). There was no significant difference in IFNγ secretion among constructs. (FIG. 5B) CD123 CAR constructs expressing a CD28 costimulatory domain had significantly lower baseline IFNγ secretion when cultured in media (n=5; CD8α.41BBz CAR vs remaining constructs p<0.0001 ()) and in the presence of CD123− tumor cells (n=5; CD8α.41BBz CAR vs remaining constructs p<0.001 (*)).

(FIG. 8A) Bioluminescence imaging results of AML progression in mice that received CD123-CAR T cells ($1\times10^7$ cells) or no T cells. (FIG. 8B) Quantification of percent survival of mice that received CD123-CAR T cells or no T cells.

(FIG. 9A) Bioluminescence imaging results of AML progression in mice that received CD123-CAR T cells ($3\times10^6$ cells) or no T cells. (FIG. 9B) Quantification of percent survival of mice that received CD123-CAR T cells or no T cells.

(FIG. 10A) Schematic of an IL13Rα2-CAR containing CD20. (FIG. 10B) IL13Rα2-CAR T cells or NT T cells were labeled with 51Chromium and treated with rituximab and/or complement in a standard cytotoxicity assay. (FIG. 10C) IL13Rα2-CAR T cells were co-cultured with IL13Rα2+ tumor cells (U373) for 8 days. Then rituximab only (control) or rituximab and complement (RRC) were added to the culture (indicated by the arrow). IL13Rα2-CAR T cells were counted 24 post treatment.

DETAILED DESCRIPTION

Figures 1A, 1B:
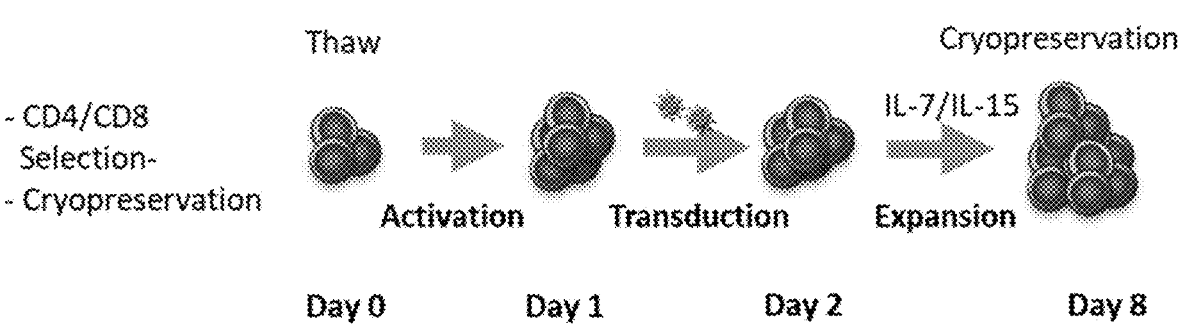
FIGS. 1A-1F illustrate the generation and characterization of CD8α.41BBz CAR T cells.

The present disclosure generally provides chimeric antigen receptors (CARs), particularly CARs that have enhanced antitumor properties and/or can be regulated by safety switches. Also provided are polypeptides of the CARs and other related molecules, polynucleotides, vectors, and cell compositions comprising the same. Pharmaceutical compositions comprising the polypeptides, polynucleotides, vectors, or cells of the present disclosure, and their uses in treating a cancer in a subject are also provided.

CARs are primarily comprised of 1) an antigen-binding moiety, such as a single-chain variable fragment (scFv) derived from an antigen-specific monoclonal antibody, and 2) a signaling domain, such as the ζ-chain from the T cell receptor CD3. These two regions are fused together via a transmembrane domain. A hinge domain is usually required to provide more flexibility and accessibility between the antigen-binding moiety and the transmembrane domain. Upon transduction, the lymphocyte expresses the CAR on its surface, and upon contact and ligation with the target antigen, it signals through the signaling domain (e.g., CD3ζ chain) inducing cytotoxicity and cellular activation.

Optimal combination of hinge domain, transmembrane domain, and costimulatory domain is required for the engineered cells (e.g., T cells or NK cells) expressing CARs to be able to expand and kill target cells in an antigen dependent manner, while bypassing a highly immunosuppressive microenvironment. Additionally, engineered cells expressing CARs may be associated with toxicity, such as targeting normal cells expressing the antigen. To reduce such toxicity, it is desirable for the engineered cells to be removed in a controllable manner. This disclosure addresses these and other needs by providing CARs that have optimized domain structure and/or can be regulated by safety switches.

Definitions

The term "chimeric antigen receptor" or "CAR" as used herein is defined as a cell-surface receptor comprising an extracellular target-binding domain, a transmembrane domain and a cytoplasmic domain, comprising a signaling domain and optionally at least one costimulatory signaling domain, all in a combination that is not naturally found together on a single protein. This particularly includes receptors wherein the extracellular domain and the cytoplasmic domain are not naturally found together on a single receptor protein. The chimeric antigen receptors of the present disclosure are intended primarily for use with lymphocyte such as T cells and natural killer (NK) cells.

The terms "T cell" and "T lymphocyte" are interchangeable and used synonymously herein. As used herein, T cell includes thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells and memory T cells. Also included are "NKT cells", which refer to a specialized population of T cells that express a semi-invariant αβ T-cell receptor, but also express a variety of molecular markers that are typically associated with NK cells, such as NK1.1. NKT cells include NK1.1+ and NK1.1−, as well as CD4+, CD4−, CD8+ and CD8− cells. The TCR on NKT cells is unique in that it recognizes glycolipid antigens presented by the MHC I-like molecule CD Id. NKT cells can have either protective or deleterious effects due to their abilities to produce cytokines that promote either inflammation or immune tolerance. Also included are "gamma-delta T cells (γδ T cells)," which refer to a specialized population that to a small subset of T cells possessing a distinct TCR on their surface, and unlike the majority of T cells in which the TCR is composed of two glycoprotein chains designated α- and β-TCR chains, the TCR in γδ T cells is made up of a γ-chain and a δ-chain. γδ T cells can play a role in immunosurveillance and immunoregulation, and were found to be an important source of IL-17 and to induce robust CD8+ cytotoxic T cell response. Also included are "regulatory T cells" or "Tregs" refers to T cells that suppress an abnormal or excessive immune response and play a role in immune tolerance. Tregs cells are typically transcription factor Foxp3-positive CD4+T cells and can also include transcription factor Foxp3-negative regulatory T cells that are IL-10-producing CD4+T cells.

The terms "natural killer cell" and "NK cell" are used interchangeable and used synonymously herein. As used herein, NK cell refers to a differentiated lymphocyte with a CD 16+ CD56+ and/or CD57+ TCR− phenotype. NKs are characterized by their ability to bind to and kill cells that fail to express "self" MHC/HLA antigens by the activation of specific cytolytic enzymes, the ability to kill tumor cells or other diseased cells that express a ligand for NK activating receptors, and the ability to release protein molecules called cytokines that stimulate or inhibit the immune response.

As used herein, the term "antigen" refers to any agent (e.g., protein, peptide, polysaccharide, glycoprotein, glycolipid, nucleic acid, portions thereof, or combinations thereof) molecule capable of being bound by a T-cell receptor. An antigen is also able to provoke an immune response. An example of an immune response may involve, without limitation, antibody production, or the activation of specific immunologically competent cells, or both. A skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components, organisms, subunits of proteins/antigens, killed or inactivated whole cells or lysates.

The term "antigen-binding moiety" refers to a target-specific binding element that may be any ligand that binds to the antigen of interest or a polypeptide or fragment thereof, wherein the ligand is either naturally derived or synthetic. Examples of antigen-binding moieties include, but are not limited to, antibodies; polypeptides derived from antibodies, such as, for example, single chain variable fragments (scFv), Fab, Fab', F(ab')2, and Fv fragments; polypeptides derived from T Cell receptors, such as, for example, TCR variable domains; secreted factors (e.g., cytokines, growth factors) that can be artificially fused to signaling domains (e.g., "zytokines"); and any ligand or receptor fragment (e.g., CD27, NKG2D) that binds to the antigen of interest. Combinatorial libraries could also be used to identify peptides binding with high affinity to the therapeutic target.

Terms "antibody" and "antibodies" refer to monoclonal antibodies, multispecific antibodies, human antibodies, humanized antibodies, chimeric antibodies, single-chain Fvs (scFv), single chain antibodies, Fab fragments, F(ab') fragments, disulfide-linked Fvs (sdFv), intrabodies, minibodies, diabodies and anti-idiotypic (anti-Id) antibodies (including, e.g., anti-Id antibodies to antigen-specific TCR), and epitope-binding fragments of any of the above. The terms "antibody" and "antibodies" also refer to covalent diabodies such as those disclosed in U.S. Pat. Appl. Pub. 2007/0004909 and Ig-DARTS such as those disclosed in U.S. Pat. Appl. Pub. 2009/0060910. Antibodies useful as a TCR-binding molecule include immunoglobulin molecules and immunologically active fragments of immunoglobulin molecules, i.e., molecules that contain an antigen-binding site. Immunoglobulin molecules can be of any type (e.g., IgG, IgE, IgM, IgD, IgA and IgY), class (e.g., IgG1, IgG2, IgG3, IgG4, IgM1, IgM2, IgA1 and IgA2) or subclass.

The term "host cell" means any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLOPACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to, HeLa, NIH3T3, Jurkat, 293, COS, CHO, Saos, and PC12.

Host cells of the present disclosure include T cells and natural killer cells that contain the DNA or RNA sequences encoding the CAR and express the CAR on the cell surface. Host cells may be used for enhancing T cell activity, natural killer cell activity, treatment of cancer, and treatment of autoimmune disease.

The terms "activation" or "stimulation" means to induce a change in their biologic state by which the cells (e.g., T cells and NK cells) express activation markers, produce cytokines, proliferate and/or become cytotoxic to target cells. All these changes can be produced by primary stimulatory signals. Costimulatory signals can amplify the magnitude of the primary signals and suppress cell death following initial stimulation resulting in a more durable activation state and thus a higher cytotoxic capacity. A "costimulatory signal" refers to a signal, which in combination with a primary signal, such as TCR/CD3 ligation, leads to T cell and/or NK cell proliferation and/or upregulation or downregulation of key molecules.

The term "proliferation" refers to an increase in cell division, either symmetric or asymmetric division of cells. The term "expansion" refers to the outcome of cell division and cell death.

The term "differentiation" refers to a method of decreasing the potency or proliferation of a cell or moving the cell to a more developmentally restricted state.

The terms "express" and "expression" mean allowing or causing the information in a gene or DNA sequence to become produced, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. An expression product can be characterized as intracellular, extracellular or transmembrane.

The term "transfection" means the introduction of a "foreign" (i.e., extrinsic or extracellular) nucleic acid into a cell using recombinant DNA technology. The term "genetic modification" means the introduction of a "foreign" (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences operably linked to polynucleotide encoding the chimeric antigen receptor, such as start, stop, promoter, signal, secretion, or other sequences used by a cell's genetic machinery. The gene or sequence may include nonfunctional sequences or sequences with no known function. A host cell that receives and expresses introduced DNA or RNA has been "genetically engineered." The DNA or RNA introduced to a host cell can come from any source, including cells of the same genus or species as the host cell, or from a different genus or species.

The term "transduction" means the introduction of a foreign nucleic acid into a cell using a viral vector.

The terms "genetically modified" or "genetically engineered" refers to the addition of extra genetic material in the form of DNA or RNA into a cell.

As used herein, the terms "variant" and "derivative" are used interchangeably herein and when used in the context of proteins or polypeptides (e.g., CAR constructs or domains thereof) refer to: (a) a polypeptide that has at least 40%, 45%, 50%, 55%, 60%, 65%, 70%, 75%, 80%, 85%, 90%, 95%, 98% or 99% sequence identity to the polypeptide it is a variant of; (b) a polypeptide encoded by a nucleotide sequence that has at least 40%, 45%, 50%, 55%, 60%, 65%, 70%, 75%, 80%, 85%, 90%, 95%, 98% or 99% sequence identity to a nucleotide sequence encoding the polypeptide it is a variant of; (c) a polypeptide that contains 1, 2, 3, 4, 5, 6, 7, 8, 9, 10, 11, 12, 13, 14, 15, 16, 17, 18, 19, 20 or more amino acid mutations (i.e., additions, deletions and/or substitutions) relative to the polypeptide it is a variant of; (d) a polypeptide encoded by nucleic acids can hybridize under high, moderate or typical stringency hybridization conditions to nucleic acids encoding the polypeptide it is a variant of; (e) a polypeptide encoded by a nucleotide sequence that can hybridize under high, moderate or typical stringency hybridization conditions to a nucleotide sequence encoding a fragment of the polypeptide, it is a variant of, of at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, or at least 150 contiguous amino acids; or (f) a fragment of the polypeptide it is a variant of.

Percent sequence identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin). Information regarding hybridization conditions (e.g., high, moderate, and typical stringency conditions) have been described, see, e.g., U.S. Patent Application Publication No. US 2005/0048549 (e.g., paragraphs 72-73).

The terms "vector", "cloning vector" and "expression vector" mean the vehicle by which a DNA or RNA sequence (e.g., a foreign gene) can be introduced into a host cell, so as to genetically modify the host and promote expression (e.g., transcription and translation) of the introduced sequence. Vectors include plasmids, synthesized RNA and DNA molecules, phages, viruses, etc. In certain embodiments, the vector is a viral vector such as, but not limited to, viral vector is an adenoviral, adeno-associated, alphaviral, herpes, lentiviral, retroviral, or vaccinia vector.

The term "regulatory element" refers to any cis-acting genetic element that controls some aspect of the expression of nucleic acid sequences. In some embodiments, the term "promoter" comprises essentially the minimal sequences required to initiate transcription. In some embodiments, the term "promoter" includes the sequences to start transcription, and in addition, also include sequences that can upregulate or downregulate transcription, commonly termed "enhancer elements" and "repressor elements", respectively.

As used herein, the term "operatively linked," and similar phrases, when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

By "enhance" or "promote," or "increase" or "expand" or "improve" refers generally to the ability of a composition contemplated herein to produce, elicit, or cause a greater physiological response (i.e., downstream effects) compared to the response caused by either vehicle or a control molecule/composition. A measurable physiological response may include an increase in T cell expansion, activation, effector function, persistence, and/or an increase in cancer cell death killing ability, among others apparent from the understanding in the art and the description herein. In certain embodiments, an "increased" or "enhanced" amount can be a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or a control composition.

By "decrease" or "lower," or "lessen," or "reduce," or "abate" refers generally to the ability of composition contemplated herein to produce, elicit, or cause a lesser physiological response (i.e., downstream effects) compared to the response caused by either vehicle or a control molecule/composition. In certain embodiments, a "decrease" or "reduced" amount can be a "statistically significant" amount, and may include a decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, a control composition, or the response in a particular cell lineage.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

The term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions described herein, refers to molecular entities and other ingredients of such compositions that are physiologically tolerable and do not typically produce untoward reactions when administered to a mammal (e.g., a human). Preferably, the term "pharmaceutically acceptable" means approved by a regulatory agency of the Federal or a state government or listed in the U.S. Pharmacopeia or other generally recognized pharmacopeia for use in mammals, and more particularly in humans.

The term "protein" is used herein encompasses all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "nucleic acid", "nucleotide", and "polynucleotide" encompass both DNA and RNA unless specified otherwise. By a "nucleic acid sequence" or "nucleotide sequence" is meant the nucleic acid sequence encoding an amino acid, the term may also refer to the nucleic acid sequence including the portion coding for any amino acids added as an artifact of cloning, including any amino acids coded for by linkers The terms "patient", "individual", "subject", and "animal" are used interchangeably herein and refer to mammals, including, without limitation, human and veterinary animals (e.g., cats, dogs, cows, horses, sheep, pigs, etc.) and experimental animal models. In a preferred embodiment, the subject is a human.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

If aspects of the disclosure are described as "comprising" a feature, or versions there of (e.g., comprise), embodiments also are contemplated "consisting of" or "consisting essentially of" the feature.

The practice of the present disclosure employs, unless otherwise indicated, conventional techniques of statistical analysis, molecular biology (including recombinant techniques), microbiology, cell biology, and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ Additional techniques are explained, e.g., in U.S. Pat. No. 7,912,698 and U.S. Patent Appl. Pub. Nos. 2011/0202322 and 2011/0307437.

The technology illustratively described herein suitably may be practiced in the absence of any element(s) not specifically disclosed herein.

The terms and expressions which have been employed are used as terms of description and not of limitation, and use of such terms and expressions do not exclude any equivalents of the features shown and described or portions thereof, and various modifications are possible within the scope of the technology claimed.

Chimeric Antigen Receptors of the Disclosure

In certain aspects, the present disclosure provides a polynucleotide encoding a chimeric antigen receptor (CAR) comprising: (a) a leader sequence, (b) an extracellular target-binding domain, (c) a hinge domain, (d) a transmembrane domain, (e) a cytoplasmic domain comprising (i) one or more costimulatory domains, and (ii) a signaling domain.

In one aspect, the present disclosure provides a polynucleotide encoding a chimeric antigen receptor (CAR) comprising: (a) a leader sequence, (b) an extracellular target-binding domain comprising a CD123-binding moiety, (c) a hinge domain derived from CD8α or CD28, (d) a transmembrane domain derived from CD8α or CD28, and (e) a cytoplasmic domain comprising (i) one or more costimulatory domains derived from CD28 and/or 4-1BB, and (ii) a signaling domain derived from CD3ζ.

In one aspect, the present disclosure provides a polynucleotide encoding a chimeric antigen receptor (CAR) comprising: (a) a leader sequence, (b) an extracellular target-binding domain comprising an IL13Rα2-binding moiety, (c) a hinge domain derived from IgG1, (d) a transmembrane domain derived from CD28, and (e) a cytoplasmic domain comprising (i) a costimulatory domain derived from CD28, and (ii) a signaling domain derived from CD3ζ.

Leader Sequence

In certain aspects, the CAR of the present disclosure comprises a leader sequence. The leader sequence may be positioned amino-terminal to the extracellular target-binding domain. The leader sequence may be optionally cleaved from the antigen-binding moiety during cellular processing and localization of the CAR to the cellular membrane.

In some embodiments, the leader sequence may be derived from CD8α. In some embodiments, the leader sequence comprises the amino acid sequence set forth in SEQ ID NO: 25 or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 25. In certain embodiments, the nucleotide sequence encoding the leader sequence comprises the nucleotide sequence that encodes the amino acid sequence of SEQ ID NO: 25, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 25. In certain embodiments, the nucleotide sequence encoding the leader sequence comprises the sequence set forth in SEQ ID NO: 26, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 26. In certain embodiments, the leader sequence comprises the amino acid sequence of SEQ ID NO: 25. In certain embodiments, the nucleotide sequence encoding the leader sequence comprises the nucleotide sequence set forth in SEQ ID NO: 26.

In some embodiments, the leader sequence may be derived from human immunoglobulin heavy chain variable region. In some embodiments, the leader sequence comprises the amino acid sequence set forth in SEQ ID NO: 27 or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 27. In certain embodiments, the nucleotide sequence encoding the leader sequence comprises the nucleotide sequence that encodes the amino acid sequence of SEQ ID NO: 27, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 27. In certain embodiments, the nucleotide sequence encoding the leader sequence comprises the sequence set forth in SEQ ID NO: 28, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 28. In certain embodiments, the leader sequence comprises the amino acid sequence of SEQ ID NO: 27. In certain embodiments, the nucleotide sequence encoding the leader sequence comprises the nucleotide sequence set forth in SEQ ID NO: 28.

Extracellular Target-Binding Domain

In certain aspects, CARs of the present disclosure comprise an extracellular target-binding domain, wherein the extracellular target-binding domain comprises an antigen-binding moiety.

The choice of antigen-binding moiety depends upon the type and number of antigens that define the surface of a target cell. For example, the antigen-binding moiety may be chosen to recognize an antigen that acts as a cell surface marker on target cells associated with a particular disease state. In certain embodiments, the CARs of the present disclosure can be genetically modified to target a tumor antigen of interest by way of engineering a desired antigen-binding moiety that specifically binds to an antigen (e.g., on a cancer cell). Non-limiting examples of cell surface markers that may act as targets for the antigen-binding moiety in the CAR of the invention include those associated with cancer cells.

Examples of antigens that may be targeted by the extracellular target-binding domains include, but are not limited to, carbonic anhydrase EX, alpha-fetoprotein, A3, antigen specific for A33 antibody, Ba 733, BrE3-antigen, CA125, CD1, CD1a, CD3, CD5, CD15, CD16, CD19, CD20, CD21, CD22, CD23, CD25, CD30, CD33, CD38, CD45, CD74, CD79a, CD80, CD123, CD138, colon-specific antigen-p (CSAp), CEA (CEACAM5), CEACAM6, CSAp, EGFR, EGP-I, EGP-2, Ep-CAM, EphA1, EphA2, EphA3, EphA4, EphA5, EphA6, EphA7, EphA8, EphA10, EphB1, EphB2, EphB3, EphB4, EphB6, FIt-I, Flt-3, folate receptor, HLA-DR, human chorionic gonadotropin (HCG) and its subunits, HER2/neu, hypoxia inducible factor (HIF-I), Ia, IL-2, IL-6, IL-8, interleukin 13 receptor α2 (IL13Rα2), insulin growth factor-1 (IGF-I), KC4-antigen, KS-1-antigen, KS1-4, Le-Y, macrophage inhibition factor (MIF), MAGE, MUC1, MUC2, MUC3, MUC4, NCA66, NCA95, NCA90, antigen specific for PAM-4 antibody, placental growth factor, p53, prostatic acid phosphatase, PSA, PSMA, RS5, S100, TAC, TAG-72, tenascin, TRAIL receptors, Tn antigen, Thomson-Friedenreich antigens, tumor necrosis antigens, VEGF, ED-B fibronectin, 17-1A-antigen, an angiogenesis marker, an oncogene marker or an oncogene product.

In some embodiments, the target-binding moiety recognizes CD123. CD123, also known as interleukin-3 receptor, is a molecule found on cells which helps transmit the signal of interleukin-3, a soluble cytokine important in the immune system. CD123 is expressed across acute myeloid leukemia (AML) subtypes, including leukemic stem cells. CD123 is also expressed at low levels in normal hematopoietic progenitor cells.

In some embodiments, the target-binding moiety recognizes interleukin 13 receptor α2 (IL13Rα2). IL13Rα2, also referred to as CD213A2 (cluster of differentiation 213A2), is a membrane bound protein that in humans is encoded by the IL13RA2 gene.

In some embodiments, the antigen-binding moiety comprises an antigen-binding polypeptide or functional variant thereof that binds to an antigen. In some embodiments, the antigen-binding polypeptide is an antibody or an antibody fragment that binds to an antigen. Antigen-binding moieties may comprise antibodies and/or antibody fragments such as monoclonal antibodies, multi specific antibodies, chimeric antibodies, single-chain Fvs (scFv), single chain antibodies, Fab fragments, F(ab') fragments, disulfide-linked Fvs (sdFv), intrabodies, minibodies, single domain antibody variable domains, nanobodies (VHHs), diabodies and anti-idiotypic (anti-Id) antibodies (including, e.g., anti-Id antibodies to antigen-specific TCR), and epitope-binding fragments of any of the above. Antibodies and/or antibody fragments may be derived from murine antibodies, rabbit antibodies, human antibodies, fully humanized antibodies, camelid antibody variable domains and humanized versions, shark antibody variable domains and humanized versions, and camelized antibody variable domains.

In some embodiments, the CD123-binding moiety is an anti-CD123 single chain variable fragment (scFv). In some embodiments, the anti-CD123 scFv is derived from antibody 26292 (scFV (292)). In some embodiments, the anti-CD123 scFv is derived from antibody 26716 (scFV (716)). The antibody 26292 and antibody 26716 are anti-IL3Rα antibodies described in U.S. Pat. No. 8,163,279, which is herein incorporated by reference in its entirety for all purposes.

In some embodiments, scFV (292) comprises the amino acid sequence set forth in SEQ ID NO: 29, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 29. In certain embodiments, the nucleotide sequence that encodes the scFV (292) comprises the nucleotide sequence that encodes the amino acid sequence of SEQ ID NO: 29, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 29. In certain embodiments, the nucleotide sequence that encodes the scFV (292) comprises the nucleotide sequence set forth in SEQ ID NO: 30, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 30. In certain embodiments, the scFV (292) comprises the amino acid sequence set forth in SEQ ID NO: 29. In certain embodiments, the nucleotide sequence that encodes the scFV (292) comprises the nucleotide sequence set forth in SEQ ID NO: 30.

In some embodiments, scFV (716) comprises the amino acid sequence set forth in SEQ ID NO: 31, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 31. In certain embodiments, the nucleotide sequence that encodes the scFV (716) comprises the nucleotide sequence that encodes the amino acid sequence of SEQ ID NO: 31, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 31. In certain embodiments, the nucleotide sequence that encodes the scFV (716) comprises the nucleotide sequence set forth in SEQ ID NO: 32, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 32. In certain embodiments, the scFV (716) comprises the amino acid sequence set forth in SEQ ID NO: 31. In certain embodiments, the nucleotide sequence that encodes the scFV (716) comprises the nucleotide sequence set forth in SEQ ID NO: 32.

In some embodiments, the IL13Rα2-binding moiety is an anti-IL13Rα2 scFv (SH2). In some embodiments, scFV (SH2) comprises the amino acid sequence set forth in SEQ ID NO: 33, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 33. In certain embodiments, the nucleotide sequence that encodes the scFV (SH2) comprises the nucleotide sequence that encodes the amino acid sequence of SEQ ID NO: 33, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 33. In certain embodiments, the nucleotide sequence that encodes the scFV (SH2) comprises the nucleotide sequence set forth in SEQ ID NO: 34, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 34. In certain embodiments, the scFV (SH2) comprises the amino acid sequence set forth in SEQ ID NO: 33. In certain embodiments, the nucleotide sequence that encodes the scFV (SH2) comprises the nucleotide sequence set forth in SEQ ID NO: 34.

Linker Region and Hinge Domain

In certain embodiments, the CAR further comprises a linker region between the extracellular antigen-binding domain and the transmembrane domain, wherein the antigen-binding moiety, linker, and the transmembrane domain are in frame with each other.

The term "linker region" as used herein generally means any oligo- or polypeptide that functions to link the antigen-binding moiety to the transmembrane domain. A linker region can be used to provide more flexibility and accessibility for the antigen-binding moiety. A linker region may comprise up to 300 amino acids, preferably 10 to 100 amino acids and most preferably 25 to 50 amino acids. A linker region may be derived from all or part of naturally occurring molecules, such as from all or part of the extracellular region of CD8, CD4 or CD28, or from all or part of an antibody constant region. Alternatively, the linker region may be a synthetic sequence that corresponds to a naturally occurring linker region sequence, or may be an entirely synthetic linker region sequence. Non-limiting examples of linker regions which may be used in accordance to the invention include a part of human CD8α chain, partial extracellular domain of CD28, FcγRllla receptor, IgG, IgM, IgA, IgD, IgE, an Ig hinge, or functional fragment thereof. In some embodiments, additional linking amino acids are added to the linker region to ensure that the antigen-binding moiety is an optimal distance from the transmembrane domain. In some embodiments, when the linker is derived from an Ig, the linker may be mutated to prevent Fc receptor binding.

In some embodiments, the linker domain comprises a hinge domain. The hinge domain may be derived from CD8α, CD28, or an immunoglobulin (IgG). For example, the IgG hinge may be from IgG1, IgG2, IgG3, IgG4, IgM1, IgM2, IgA1, IgA2, IgD, IgE, or a chimera thereof.

In some embodiments, the hinge domain is derived from CD8α. In some embodiments, the hinge domain derived from CD8α comprises the amino acid sequence set forth in SEQ ID NO: 37, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 37. In certain embodiments, the nucleotide sequence that encodes the CD8α hinge domain comprises the nucleotide sequence that encodes the amino acid sequence of SEQ ID NO: 37, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 37. In certain embodiments, the nucleotide sequence that encodes the CD8α hinge domain comprises the nucleotide sequence set forth in SEQ ID NO: 38, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 38. In certain embodiments, the CD8α hinge domain comprises the amino acid sequence set forth in SEQ ID NO: 37. In certain embodiments, the nucleotide sequence that encodes the CD8α hinge domain comprises the nucleotide sequence set forth in SEQ ID NO: 38.

In some embodiments, the hinge domain is derived from CD28. In some embodiments, the hinge domain derived from CD28 comprises the amino acid sequence set forth in SEQ ID NO: 43, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 43. In certain embodiments, the nucleotide sequence that encodes the CD28 hinge domain comprises the nucleotide sequence that encodes the amino acid sequence of SEQ ID NO: 43, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 43. In certain embodiments, the nucleotide sequence that encodes the CD28 hinge domain comprises the nucleotide sequence set forth in SEQ ID NO: 44, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 44. In certain embodiments, the CD28 hinge domain comprises the amino acid sequence set forth in SEQ ID NO: 43. In certain embodiments, the nucleotide sequence that encodes the CD28 hinge domain comprises the nucleotide sequence set forth in SEQ ID NO: 44.

In some embodiments, the hinge domain is derived from IgG1. In some embodiments, the hinge domain derived from IgG1 comprises the amino acid sequence set forth in SEQ ID NO: 48, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 48. In certain embodiments, the nucleotide sequence that encodes the IgG1 hinge domain comprises the nucleotide sequence that encodes the amino acid sequence of SEQ ID NO: 48, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 48. In certain embodiments, the nucleotide sequence that encodes the IgG1 hinge domain comprises the nucleotide sequence set forth in SEQ ID NO: 49, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 49. In certain embodiments, the IgG1 hinge domain comprises the amino acid sequence set forth in SEQ ID NO: 48. In certain embodiments, the nucleotide sequence that encodes the IgG1 hinge domain comprises the nucleotide sequence set forth in SEQ ID NO: 49.

In some embodiments, in addition to the hinge domain, the linker region comprises additional linker amino acids to allow for extra flexibility and/or accessibility.

In some embodiments, the linker region comprises the amino acid sequence set forth in SEQ ID NO: 50, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 50. In certain embodiments, the nucleotide sequence that encodes the IgG1 hinge domain comprises the nucleotide sequence that encodes the amino acid sequence of SEQ ID NO: 50, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 50. In certain embodiments, the nucleotide sequence that encodes the IgG1 hinge domain comprises the nucleotide sequence set forth in SEQ ID NO: 51, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 51. In certain embodiments, the IgG1 hinge domain comprises the amino acid sequence set forth in SEQ ID NO: 50. In certain embodiments, the nucleotide sequence that encodes the IgG1 hinge domain comprises the nucleotide sequence set forth in SEQ ID NO: 51.

Transmembrane Domain

In certain aspects, CARs of the present disclosure comprise a transmembrane domain, fused in frame between the extracellular target-binding domain and the cytoplasmic domain.

The transmembrane domain may be derived from the protein contributing to the extracellular target-binding domain, the protein contributing the signaling or co-signaling domain, or by a totally different protein. In some instances, the transmembrane domain can be selected or modified by amino acid substitution, deletions, or insertions to minimize interactions with other members of the CAR complex. In some instances, the transmembrane domain can be selected or modified by amino acid substitution, deletions, or insertions to avoid-binding of proteins naturally associated with the transmembrane domain. In certain embodiments, the transmembrane domain includes additional amino acids to allow for flexibility and/or optimal distance between the domains connected to the transmembrane domain.

The transmembrane domain may be derived either from a natural or from a synthetic source. Where the source is natural, the domain may be derived from any membrane-bound or transmembrane protein. Non-limiting examples of transmembrane domains of particular use in this invention may be derived from (i.e. comprise at least the transmembrane region(s) of) the α, β or ζ chain of the T-cell receptor, CD28, CD3 epsilon, CD45, CD4, CD5, CD8, CD9, CD16, CD22, CD33, CD37, CD40, CD64, CD80, CD86, CD134, CD137, CD154. Alternatively, the transmembrane domain may be synthetic, in which case it will comprise predominantly hydrophobic residues such as leucine and valine. For example, a triplet of phenylalanine, tryptophan and/or valine can be found at each end of a synthetic transmembrane domain.

In some embodiments, the transmembrane domain in the CAR of the present disclosure is derived from CD8α. In some embodiments, the transmembrane domain derived from CD8α comprises the amino acid sequence set forth in SEQ ID NO: 39, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 39. In certain embodiments, the nucleotide sequence that encodes the CD8α transmembrane domain comprises the nucleotide sequence that encodes the amino acid sequence of SEQ ID NO: 39, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 39. In certain embodiments, the nucleotide sequence that encodes the CD8α transmembrane domain comprises the nucleotide sequence set forth in SEQ ID NO: 40, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 40. In certain embodiments, the CD8α transmembrane domain comprises the amino acid sequence set forth in SEQ ID NO: 39. In certain embodiments, the nucleotide sequence that encodes the CD8α transmembrane domain comprises the nucleotide sequence set forth in SEQ ID NO: 40.

In some embodiments, the transmembrane domain in the CAR of the present disclosure is derived from CD28. In some embodiments, the transmembrane domain derived from CD28 comprises the amino acid sequence set forth in SEQ ID NO: 45, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 45. In certain embodiments, the nucleotide sequence that encodes the CD28 transmembrane domain comprises the nucleotide sequence that encodes the amino acid sequence of SEQ ID NO: 45, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 45. In certain embodiments, the nucleotide sequence that encodes the CD28 transmembrane domain comprises the nucleotide sequence set forth in SEQ ID NO: 46 or 47, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 46 or 47. In certain embodiments, the CD28 transmembrane domain comprises the amino acid sequence set forth in SEQ ID NO: 45. In certain embodiments, the nucleotide sequence that encodes the CD28 transmembrane domain comprises the nucleotide sequence set forth in SEQ ID NO: 46 or 47.

Cytoplasmic Domain

In certain aspects, CARs of the present disclosure comprise a cytoplasmic domain, which comprises one or more costimulatory domains and one or more signaling domains. The cytoplasmic domain, which comprises one or more costimulatory domains and one or more signaling domains, is responsible for activation of at least one of the normal effector functions of the lymphocyte in which the CAR has been placed in. The term "effector function" refers to a specialized function of a cell. Effector function of a T cell, for example, may be cytolytic activity or helper activity including the secretion of cytokines. Thus, the term "signaling domain" refers to the portion of a protein which transduces the effector function signal and directs the cell to perform a specialized function. While usually the entire signaling domain is present, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the signaling domain sufficient to transduce the effector function signal.

Non-limiting examples of costimulatory domains which can be used in the CARs of the present disclosure include, those derived from 4-1BB (CD137), CD28, ICOS, CD134 (OX-40), BTLA, CD27, CD30, GITR, CD226, and HVEM. In some embodiments, the CAR of the present disclosure comprises one costimulatory domain. In some embodiments, the CAR of the present disclosure comprises a costimulatory domain derived from 4-1BB. In some embodiments, the CAR of the present disclosure comprises a costimulatory domain derived from CD28. In some embodiments, the CAR of the present disclosure comprises two costimulatory domains. In some embodiments, the CAR of the present disclosure comprises a costimulatory domain derived from 4-1BB and a costimulatory domain derived from CD28.

Non-limiting examples of signaling domains which can be used in the CARs of the present disclosure include, e.g., signaling domains derived from DAP10, DAP12, Fc epsilon receptor I gamma chain (FCER1G), FcR β, CD3δ, CD3ε, CD3γ, CD3ζ, CD5, CD22, CD226, CD66d, CD79A, and CD79B. In some embodiments, the CAR of the present disclosure comprises a signaling domain derived from CD3ζ.

In some embodiments, the signaling domain(s) and costimulatory domain(s) can be in any order. In some embodiments, the signaling domain is upstream of the co-stimulatory domains. In some embodiments, the signaling domain is downstream from the costimulatory domains. In the cases where two or more costimulatory domains are included, the order of the costimulatory domains could be switched.

In some embodiments, the costimulatory domain derived from 4-1BB comprises the amino acid sequence set forth in SEQ ID NO: 52, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 52. In certain embodiments, the nucleotide sequence that encodes the 4-1BB costimulatory domain comprises the nucleotide sequence that encodes the amino acid sequence of SEQ ID NO: 52, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 52. In certain embodiments, the nucleotide sequence that encodes the 4-1BB costimulatory domain comprises the nucleotide sequence set forth in SEQ ID NO: 53, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 53. In certain embodiments, the 4-1BB costimulatory domain comprises the amino acid sequence set forth in SEQ ID NO: 52. In certain embodiments, the nucleotide sequence that encodes the 4-1BB costimulatory domain comprises the nucleotide sequence set forth in SEQ ID NO: 53.

In some embodiments, the costimulatory domain derived from CD28 comprises the amino acid sequence set forth in SEQ ID NO: 54, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 54. In certain embodiments, the nucleotide sequence that encodes the CD28 costimulatory domain comprises the nucleotide sequence that encodes the amino acid sequence of SEQ ID NO: 54, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 54. In certain embodiments, the nucleotide sequence that encodes the CD28 costimulatory domain comprises the nucleotide sequence set forth in SEQ ID NO: 55, 56, or 57, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 55, 56, or 57. In certain embodiments, the CD28 costimulatory domain comprises the amino acid sequence set forth in SEQ ID NO: 54. In certain embodiments, the nucleotide sequence that encodes the CD28 costimulatory domain comprises the nucleotide sequence set forth in SEQ ID NO: 55, 56, or 57.

In some embodiments, the signaling domain derived from CD3ζ comprises the amino acid sequence set forth in SEQ ID NO: 58 or 60, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 58 or 60. In certain embodiments, the nucleotide sequence that encodes the CD3 signaling domain comprises the nucleotide sequence that encodes the amino acid sequence of SEQ ID NO: 58 or 60, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 58 or 60. In certain embodiments, the nucleotide sequence that encodes the CD3ζ signaling domain comprises the nucleotide sequence set forth in SEQ ID NO: 59 or 61, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 59 or 61. In certain embodiments, the CD3ζ signaling domain comprises the amino acid sequence set forth in SEQ ID NO: 58 or 60. In certain embodiments, the nucleotide sequence that encodes the CD3ζ signaling domain comprises the nucleotide sequence set forth in SEQ ID NO: 59 or 61.

Safety Switch

In certain aspects, CARs of the present disclosure may be regulated by a safety switch. As used herein, the term "safety switch" refers to any mechanism that is capable of removing or inhibiting the effect of a CAR from a system (e.g., a culture or a subject). Safety switches can function to increase the safety of the CAR.

The function of the safety switch may be inducible. Non-limiting examples of safety switches include (a) molecules that are expressed on the cell surface and can be targeted with a clinical grade monoclonal antibody including CD20, EGFR or a fragment thereof, HER2 or a fragment thereof, and (b) inducible suicide genes (e.g., but not limited to herpes simplex virus thymidine kinase (HSV-TK) and inducible caspase 9 (see Straathof et al. (2005) *Blood.* 105(11): 4247-4254; US Publ. No. 2011/0286980, each of which are incorporated herein by reference in their entirety for all purposes).

In some embodiments, the safety switch is a CD20 polypeptide. Expression of human CD20 on the cell surface presents an attractive strategy for a safety switch. The inventors and others have shown that cells that express CD20 can be rapidly eliminated with the FDA approved monoclonal antibody rituximab through complement-mediated cytotoxicity and antibody-dependent cell-mediated cytotoxicity (see e.g., Griffioen, M., et al. *Haematologica* 94, 1316-1320 (2009), which is incorporated herein by reference in its entirety for all purposes). Rituximab is an anti-CD20 monoclonal antibody that has been FDA approved for Chronic Lymphocytic Leukemia (CLL) and Non-Hodgkin's Lymphoma (NHL), among others (Storz, U. *MAbs* 6, 820-837 (2014), which is incorporated herein by reference in its entirety for all purposes). The CD20 safety switch is non-immunogenic and can function as a reporter/selection marker in addition to a safety switch (Bonifant, C. L., et al. *Mol Ther* 24, 1615-1626 (2016); van Loenen, M. M., et al. *Gene Ther* 20, 861-867 (2013); each of which is incorporated herein by reference in its entirety for all purposes).

Accordingly, in some embodiments, the polynucleotide encoding a CAR of the present disclosure further comprises a sequence encoding a CD20 polypeptide. In some embodiments, the CD20 polypeptide comprises the amino acid sequence set forth in SEQ ID NO: 62, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 62. In certain embodiments, the nucleotide sequence that encodes the CD20 polypeptide comprises the nucleotide sequence that encodes the amino acid sequence of SEQ ID NO: 62, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 62. In certain embodiments, the nucleotide sequence that encodes the CD20 polypeptide comprises the nucleotide sequence set forth in SEQ ID NO: 63 or 64, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 63 or 64. In certain embodiments, the CD20 polypeptide comprises the amino acid sequence set forth in SEQ ID NO: 62. In certain embodiments, the nucleotide sequence that encodes the CD20 polypeptide comprises the nucleotide sequence set forth in SEQ ID NO: 63 or 64.

In some embodiments, the sequence encoding the CD20 polypeptide is operably linked to the sequence encoding CAR via a sequence encoding a self-cleaving peptide and/or an Internal Ribosome Entry Site (IRES).

Non-limiting examples of self-cleaving peptide sequences includes *Thosea asigna* virus 2A (T2A; EGRGSLLTCGDVEENPGP (SEQ ID NO: 65) or GSGEGRGSLLTCGDVEENPGP (SEQ ID NO: 68)); the foot and mouth disease virus (FMDV) 2A sequence (F2A; GSGSRVTELLYRMKRAETYCPRPLLAIHPTEAR-HKQKIVAPVKQLLNFDLLKLAGDV ESNPGP (SEQ ID NO: 69)), Sponge (*Amphimedon queenslandica*) 2A sequence (LLCFLLLLLSGDVELNPGP (SEQ ID NO: 70); or HHFMFLLLLLAGDIELNPGP (SEQ ID NO: 71)); acorn worm 2A sequence (*Saccoglossus kowalevskii*) (WFLVLLSFILSGDIEVNPGP (SEQ ID NO: 72)); amphioxus (*Branchiostoma floridae*) 2A sequence (KNCAMYMLLLSGDVETNPGP (SEQ ID NO: 73); or MVISQLMLKLAGDVEENPGP (SEQ ID NO: 74)); porcine teschovirus-1 2A sequence (P2A; GSGATNFSLLKQAGDVEENPGP (SEQ ID NO: 75)); and equine rhinitis A virus 2A sequence (E2A; GSGQCTNYALLKLAGDVESNPGP (SEQ ID NO: 76)). In some embodiments, the separation sequence is a naturally occurring or synthetic sequence. In certain embodiments, the separation sequence includes the 2A consensus sequence D-X-E-X-NPGP (SEQ ID NO: 77), in which X is any amino acid residue.

Alternatively, an Internal Ribosome Entry Site (IRES) may be used to link the CAR and the CD20 polypeptide. IRES is an RNA element that allows for translation initiation in a cap-independent manner. IRES can link two coding sequences in one bicistronic vector and allow the translation of both proteins in cells.

In some embodiments, the self-cleaving 2A peptide is a T2A peptide and comprises the amino acid sequence set forth in SEQ ID NO: 65. In some embodiments, the sequence encoding the T2A peptide comprises the nucleotide sequence of SEQ ID NO: 66 or 67.

In some embodiments, polynucleotide encoding a CAR further comprising a linker sequence between the self-cleaving peptide and the CD20 polypeptide or the CAR. In some embodiments, the linker sequence encodes ASRA (SEQ ID NO: 78). In some embodiments, the linker sequence comprises the nucleotide sequence GCCTCCAGAGCC (SEQ ID NO: 79).

CARs of the present disclosure may further comprise an accessory gene that encodes an accessory peptide. Examples of accessory genes can include a transduced host cell selection marker, an in vivo tracking marker, a cytokine, a suicide gene, or some other functional gene. In certain embodiments, the functional accessory gene can increase the safety of the CAR. In certain embodiments, the CAR comprises at least one accessory gene. In certain embodiments, the CAR comprises one accessory gene. In other embodiments, the CAR comprises two accessory genes. In yet another embodiment, the CAR comprises three accessory genes. For example, the CAR construct may comprise an accessory gene which is truncated CD19 (tCD19). The tCD19 can be used as a tag. Expression of tCD19 may also help determine transduction efficiency.

Non-limiting examples of classes of accessory genes that can be used to increase the effector function of CAR containing host cells, include (a) secretable cytokines (e.g., but not limited to, IL-7, IL-12, IL-15, IL-18), (b) membrane bound cytokines (e.g., but not limited to, IL-15), (c) chimeric cytokine receptors (e.g., but not limited to, IL-2/IL-7, IL-4/IL-7), (d) constitutive active cytokine receptors (e.g., but not limited to, C7R), (e) dominant negative receptors (DNR; e.g., but not limited to TGFRII DNR), (f) ligands of costimulatory molecules (e.g., but not limited to, CD80, 4-1BBL), (g) antibodies, including fragments thereof and bispecific antibodies (e.g., but not limited to, bispecific T-cell engagers (BiTEs)), or (h) a second CAR.

In some embodiments, the sequence encoding an accessory gene is operably linked to the sequence encoding CAR via a sequence encoding a self-cleaving peptide and/or an Internal Ribosome Entry Site (IRES) as disclosed herein.

Non-Limiting Examples of CARs of the Present Disclosure

In some embodiments, a CAR of the present disclosure comprises: (a) a leader sequence derived from CD8α, (b) an extracellular target-binding domain comprising scFV (292), (c) a hinge domain derived from CD8α, (d) a transmembrane domain derived from CD8α, (e) a cytoplasmic domain comprising (i) a costimulatory domain derived from 4-1BB, and (ii) a signaling domain derived from CD3. In some embodiments, the CAR comprises the amino acid sequence set forth in SEQ ID NO: 1, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1. In certain embodiments, the nucleotide sequence that encodes the CAR comprises the nucleotide sequence that encodes the amino acid sequence of SEQ ID NO: 1, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1. In certain embodiments, the nucleotide sequence that encodes the CAR comprises the nucleotide sequence set forth in SEQ ID NO: 2, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 2. In certain embodiments, the CAR comprises the amino acid sequence set forth in SEQ ID NO: 1. In certain embodiments, the nucleotide sequence that encodes the CAR comprises the nucleotide sequence set forth in SEQ ID NO: 2. In some embodiments, the polynucleotide encoding the CAR further comprises a sequence encoding the CD20 polypeptide. In some embodiments, the polynucleotide encoding the CAR and the CD20 polypeptide comprises the nucleotide sequence that encodes the amino acid sequence of SEQ ID NO: 13, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 13. In some embodiments, the polynucleotide encoding the CAR and the CD20 polypeptide comprises the nucleotide sequence set forth in SEQ ID NO: 14, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 14. In certain embodiments, the polynucleotide sequence encoding the CAR and the CD20 polypeptide comprises the nucleotide sequence set forth in SEQ ID NO: 14.

In some embodiments, a CAR of the present disclosure comprises: (a) a leader sequence derived from CD8α, (b) an extracellular target-binding domain comprising scFV (292), (c) a hinge domain derived from CD8α, (d) a transmembrane domain derived from CD8α, (e) a cytoplasmic domain comprising (i) a costimulatory domain derived from CD28, and (ii) a signaling domain derived from CD3. In some embodiments, the CAR comprises the amino acid sequence set forth in SEQ ID NO: 3, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3. In certain embodiments, the nucleotide sequence that encodes the CAR comprises the nucleotide sequence that encodes the amino acid sequence of SEQ ID NO: 3, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 3. In certain embodiments, the nucleotide sequence that encodes the CAR comprises the nucleotide sequence set forth in SEQ ID NO: 4, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 4. In certain embodiments, the CAR comprises the amino acid sequence set forth in SEQ ID NO: 3. In certain embodiments, the nucleotide sequence that encodes the CAR comprises the nucleotide sequence set forth in SEQ ID NO: 4. In some embodiments, the polynucleotide encoding the CAR further comprises a sequence encoding the CD20 polypeptide. In some embodiments, the polynucleotide encoding the CAR and the CD20 polypeptide comprises the nucleotide sequence that encodes the amino acid sequence of SEQ ID NO: 15, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 15. In some embodiments, the polynucleotide encoding the CAR and the CD20 polypeptide comprises the nucleotide sequence set forth in SEQ ID NO: 16, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 16. In certain embodiments, the polynucleotide sequence encoding the CAR and the CD20 polypeptide comprises the nucleotide sequence set forth in SEQ ID NO: 16.

In some embodiments, a CAR of the present disclosure comprises: (a) a leader sequence derived from CD8α, (b) an extracellular target-binding domain comprising scFV (292), (c) a hinge domain derived from CD28, (d) a transmembrane domain derived from CD28, (e) a cytoplasmic domain comprising (i) a costimulatory domain derived from CD28, a costimulatory domain derived from 4-1BB, and (ii) a signaling domain derived from CD3. In some embodiments, the CAR comprises the amino acid sequence set forth in SEQ ID NO: 5, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5. In certain embodiments, the nucleotide sequence that encodes the CAR comprises the nucleotide sequence that encodes the amino acid sequence of SEQ ID NO: 5, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 5. In certain embodiments, the nucleotide sequence that encodes the CAR comprises the nucleotide sequence set forth in SEQ ID NO: 6, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 6. In certain embodiments, the CAR comprises the amino acid sequence set forth in SEQ ID NO: 5. In certain embodiments, the nucleotide sequence that encodes the CAR comprises the nucleotide sequence set forth in SEQ ID NO: 6. In some embodiments, the polynucleotide encoding the CAR further comprises a sequence encoding the CD20 polypeptide. In some embodiments, the polynucleotide encoding the CAR and the CD20 polypeptide comprises the nucleotide sequence that encodes the amino acid sequence of SEQ ID NO: 17, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 17. In some embodiments, the polynucleotide encoding the CAR and the CD20 polypeptide comprises the nucleotide sequence set forth in SEQ ID NO: 18, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 18. In certain embodiments, the polynucleotide sequence encoding the CAR and the CD20 polypeptide comprises the nucleotide sequence set forth in SEQ ID NO: 18.

In some embodiments, a CAR of the present disclosure comprises: (a) a leader sequence derived from CD8α, (b) an extracellular target-binding domain comprising scFV (292), (c) a hinge domain derived from CD28, (d) a transmembrane domain derived from CD28, (e) a cytoplasmic domain comprising (i) a costimulatory domain derived from CD28 and (ii) a signaling domain derived from CD3. In some embodiments, the CAR comprises the amino acid sequence set forth in SEQ ID NO: 7, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 7. In certain embodiments, the nucleotide sequence that encodes the CAR comprises the nucleotide sequence that encodes the amino acid sequence of SEQ ID NO: 7, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 7. In certain embodiments, the nucleotide sequence that encodes the CAR comprises the nucleotide sequence set forth in SEQ ID NO: 8, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 8. In certain embodiments, the CAR comprises the amino acid sequence set forth in SEQ ID NO: 7. In certain embodiments, the nucleotide sequence that encodes the CAR comprises the nucleotide sequence set forth in SEQ ID NO: 8. In some embodiments, the polynucleotide encoding the CAR further includes a sequence encoding the CD20 polypeptide. In some embodiments, the polynucleotide encoding the CAR and the CD20 polypeptide comprises the nucleotide sequence that encodes the amino acid sequence of SEQ ID NO: 19, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 19. In some embodiments, the polynucleotide encoding the CAR and the CD20 polypeptide comprises the nucleotide sequence set forth in SEQ ID NO: 20, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 20. In certain embodiments, the polynucleotide sequence encoding the CAR and the CD20 polypeptide comprises the nucleotide sequence set forth in SEQ ID NO: 20.

In some embodiments, a CAR of the present disclosure comprises: (a) a leader sequence derived from CD8α, (b) an extracellular target-binding domain comprising scFV (716), (c) a hinge domain derived from CD8α, (d) a transmembrane domain derived from CD8α, (e) a cytoplasmic domain comprising (i) a costimulatory domain derived from CD28 and (ii) a signaling domain derived from CD3. In some embodiments, the CAR comprises the amino acid sequence set forth in SEQ ID NO: 9, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 9. In certain embodiments, the nucleotide sequence that encodes the CAR comprises the nucleotide sequence that encodes the amino acid sequence of SEQ ID NO: 9, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 9. In certain embodiments, the nucleotide sequence that encodes the CAR comprises the nucleotide sequence set forth in SEQ ID NO: 10, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 10. In certain embodiments, the CAR comprises the amino acid sequence set forth in SEQ ID NO: 9. In certain embodiments, the nucleotide sequence that encodes the CAR comprises the nucleotide sequence set forth in SEQ ID NO: 10. In some embodiments, the polynucleotide encoding the CAR further includes a sequence encoding the CD20 polypeptide. In some embodiments, the polynucleotide encoding the CAR and the CD20 polypeptide comprises the nucleotide sequence that encodes the amino acid sequence of SEQ ID NO: 21, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 21. In some embodiments, the polynucleotide encoding the CAR and the CD20 polypeptide comprises the nucleotide sequence set forth in SEQ ID NO: 22, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 22. In certain embodiments, the polynucleotide sequence encoding the CAR and the CD20 polypeptide comprises the nucleotide sequence set forth in SEQ ID NO: 22.

In some embodiments, a CAR of the present disclosure comprises: (a) a leader sequence derived from human immunoglobulin heavy chain variable region, (b) an extracellular target-binding domain comprising an IL13Rα2-binding moiety, (c) a hinge domain derived from IgG1, (d) a transmembrane domain derived from CD28, (e) a cytoplasmic domain comprising (i) a costimulatory domain derived from CD28 and (ii) a signaling domain derived from CD3ζ. In some embodiments, the CAR comprises the amino acid sequence set forth in SEQ ID NO: 11, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 11. In certain embodiments, the nucleotide sequence that encodes the CAR comprises the nucleotide sequence that encodes the amino acid sequence of SEQ ID NO: 11, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 11. In certain embodiments, the nucleotide sequence that encodes the CAR comprises the nucleotide sequence set forth in SEQ ID NO: 12, or a nucleotide sequence having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 12. In certain embodiments, the CAR comprises the amino acid sequence set forth in SEQ ID NO: 11. In certain embodiments, the nucleotide sequence that encodes the CAR comprises the nucleotide sequence set forth in SEQ ID NO: 12. In some embodiments, the polynucleotide encoding the CAR further includes a sequence encoding the CD20 polypeptide. In some embodiments, the polynucleotide encoding the CAR and the CD20 polypeptide comprises the nucleotide sequence that encodes the amino acid sequence of SEQ ID NO: 23, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 23. In some embodiments, the polynucleotide encoding the CAR and the CD20 polypeptide comprises the nucleotide sequence set forth in SEQ ID NO: 24, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 24. In certain embodiments, the polynucleotide sequence encoding the CAR and the CD20 polypeptide comprises the nucleotide sequence set forth in SEQ ID NO: 24.

In various embodiments, the polynucleotide encoding a CAR is a DNA molecule. In various embodiments, the polynucleotide encoding a CAR is an RNA molecule.

In one aspect, the present disclosure provides CAR polypeptides encoded by a polynucleotide described above.

Vectors

In one aspect, the present disclosure provides recombinant vectors comprising a polynucleotide described above. In some embodiments, the recombinant vector comprises a polynucleotide encoding a CAR described above. In some embodiments, the recombinant vector comprises a polynucleotide encoding both a CAR and a safety switch (e.g., CD20 polypeptide) described above. In certain embodiments, the polynucleotide is operatively linked to at least one regulatory element for expression of the chimeric antigen receptor.

In certain embodiments, recombinant vectors of the invention comprise the nucleotide sequence of SEQ ID NO: 2, 4, 6, 8, 10, 12, 14, 16, 18, 20, 22 or 24, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 22, 4, 6, 8, 10, 12, 14, 16, 18, 20, 22 or 24. In certain embodiments, recombinant vectors comprise a nucleotide sequence that encodes the amino acid sequence of SEQ ID NO: 1, 3, 5, 7, 9, 11, 13, 15, 17, 19, 21, or 23, or a variant thereof having at least 50, at least 55, at least 60, at least 65, at least 70, at least 75, at least 80, at least 85, at least 90, at least 91, at least 92, at least 93, at least 94, at least 95, at least 96, at least 97, at least 98 or at least 99%, sequence identity with SEQ ID NO: 1, 3, 5, 7, 9, 11, 13, 15, 17, 19, 21, or 23.

In some embodiments, the vector is a viral vector. The viral vector may be a retroviral vector, an adenoviral vector, an adeno-associated virus vector, an alphaviral vector, a herpes virus vector, and a vaccinia virus vector. In some embodiments, the viral vector is a lentiviral vector.

In some embodiments, the vector is a non-viral vector. The viral vector may be a plasmid or a transposon (such as a PiggyBac- or a Sleeping Beauty transposon).

In certain embodiments, the polynucleotide encoding the CAR is operably linked to at least a regulatory element. The regulatory element can be capable of mediating expression of the CAR in the host cell. Regulatory elements include, but are not limited to, promoters, enhancers, initiation sites, polyadenylation (polyA) tails, IRES elements, response elements, and termination signals. In certain embodiments, the regulatory element regulates CAR expression. In certain embodiments, the regulatory element increased the expression of the CAR. In certain embodiments, the regulatory element increased the expression of the CAR once the host cell is activated. In certain embodiments, the regulatory element decreases expression of the CAR. In certain embodiments, the regulatory element decreases expression of the CAR once the host cell is activated.

CAR-Modified Host Cells

In one aspect, the present disclosure provides an isolated host cell comprising a polynucleotide or a recombinant vector described herein. In one aspect, the present disclosure provides an isolated host cell comprising a CAR described herein. In various embodiments, the isolated host cell further comprises a CD20 polypeptide. In some embodiments, the CD20 polypeptide comprises the amino acid sequence set forth in SEQ ID NO: 62.

In various embodiments, the host cell is an immune cell. The immune cell may be a T cell or a natural killer (NK) cell.

In various embodiments, the host cell is a T cell. T cells may include, but are not limited to, thymocytes, naive T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, or any other subset of T cells. Other illustrative populations of T cells suitable for use in particular embodiments include naive T cells memory T cells, and NKT cells.

In some embodiments, the T cell is selected from a CD8+ T cell, a CD4+ T cell, a cytotoxic T cell, an αβ T cell receptor (TCR) T cell, a natural killer T (NKT) cell, a γδ T cell, a memory T cell, a T-helper cell, and a regulatory T cell (Treg).

In various embodiments, the host cell is a NK cell. NK cell refers to a differentiated lymphocyte with a CD3− CD16+, CD3− CD56+, CD16+CD56+ and/or CD57+ TCR-phenotype.

In various embodiments, the host cell has been activated and/or expanded ex vivo.

In various embodiments, the host cell is an allogeneic cell. In various embodiments, the host cell is an autologous cell.

In some embodiments, the host cell is isolated from a subject having a cancer, wherein one or more cells of the cancer express CD123. Non-limiting examples of cancers that express CD123 include Acute lymphoblastic leukemia (ALL), Acute myeloid leukemia (AML), Blastic Plasmacytoid Dendritic Neoplasm (BPCDN), and Hairy cell leukemia. In some embodiments, the cancer is an acute myeloid leukemia (AML). In some embodiments, the cancer is an acute lymphoblastic leukemia (ALL).

In some embodiments, the host cell is isolated from a subject having a cancer, wherein one or more cells of the cancer express IL13Rα2. Non-limiting examples of cancers that express IL13Rα2 include a brain cancer such as glioblastoma, a colon cancer, a renal cell carcinoma, a pancreatic cancer, a melanoma, a head and neck cancer, a mesothelioma, or an ovarian cancer.

In some embodiments, the host cell is derived from a blood, marrow, tissue, or a tumor sample.

In one aspect, the present disclosure provides a method of generating an isolated host cell described herein. The method includes genetically modifying the host cell with a polynucleotide encoding a CAR and optionally a safety switch (e.g., CD20 polypeptide), or the recombinant vector comprising the polynucleotide encoding a CAR and optionally a safety switch (e.g., CD20 polypeptide). The genetically modifying step may be conducted in vivo or ex vivo. In some embodiments, the genetically modifying step is conducted ex vivo. The method may further include activation and/or expansion of the host cell ex vivo before, after and/or during the genetic modification.

Isolation/Enrichment

The host cells may be autologous/autogeneic ("self") or non-autologous ("non-self," e.g., allogeneic, syngeneic or xenogeneic). In certain embodiments, the host cells are obtained from a mammalian subject. In other embodiments, the host cells are obtained from a primate subject. In certain embodiments, the host cells are obtained from a human subject.

Lymphocytes can be obtained from sources such as, but not limited to, peripheral blood mononuclear cells, bone marrow, lymph nodes tissue, cord blood, thymus issue, tissue from a site of infection, ascites, pleural effusion, spleen tissue, and tumors. Lymphocytes may also be generated by differentiation of stem cells. In certain embodiments, lymphocytes can be obtained from blood collected from a subject using techniques generally known to the skilled person, such as sedimentation, e.g., FICOLL™ separation.

In certain embodiments, cells from the circulating blood of a subject are obtained by apheresis. An apheresis device typically contains lymphocytes, including T cells, monocytes, granulocytes, B cells, other nucleated white blood cells, red blood cells, and platelets. In certain embodiments, the cells collected by apheresis may be washed to remove the plasma fraction and to place the cells in an appropriate buffer or media for subsequent processing. The cells can be washed with PBS or with another suitable solution that lacks calcium, magnesium, and most, if not all other, divalent cations. A washing step may be accomplished by methods known to those in the art, such as, but not limited to, using a semiautomated flowthrough centrifuge (e.g., Cobe 2991 cell processor, or the Baxter CytoMate). After washing, the cells may be resuspended in a variety of biocompatible buffers, cell culture medias, or other saline solution with or without buffer.

In certain embodiments, host cells can be isolated from peripheral blood mononuclear cells (PBMCs) by lysing the red blood cells and depleting the monocytes. As an example, the cells can be sorted by centrifugation through a PERCOLL™ gradient. In certain embodiments, after isolation of PBMC, both cytotoxic and helper T lymphocytes can be sorted into naive, memory, and effector T cell subpopulations either before or after activation, expansion, and/or genetic modification.

In certain embodiments, T lymphocytes can be enriched. For example, a specific subpopulation of T lymphocytes, expressing one or more markers such as, but not limited to, CD3, CD4, CD8, CD14, CD15, CD16, CD19, CD27, CD28, CD34, CD36, CD45RA, CD45RO, CD56, CD62, CD62L, CD122, CD123, CD127, CD235a, CCR7, HLA-DR or a combination thereof using either positive or negative selection techniques. In certain embodiments, the T lymphocytes for use in the compositions of the invention do not express or do not substantially express one or more of the following markers: CD57, CD244, CD160, PD-1, CTLA4, TIM3, and LAG3.

In certain embodiments, NK cells can be enriched. For example, a specific subpopulation of T lymphocytes, expressing one or more markers such as, but not limited to, CD2, CD16, CD56, CD57, CD94, CD122 or a combination thereof using either positive or negative selection techniques.

Stimulation/Activation

In order to reach sufficient therapeutic doses of host cell compositions, host cells are often subjected to one or more rounds of stimulation/activation. In certain embodiments, a method of producing host cells for administration to a subject comprises stimulating the host cells to become activated in the presence of one or more stimulatory signals or agents (e.g., compound, small molecule, e.g., small organic molecule, nucleic acid, polypeptide, or a fragment, isoform, variant, or analog thereof). In certain embodiments, a method of producing host cells for administration to a subject comprises stimulating the host cells to become activated and to proliferate in the presence of one or more stimulatory signals or agents.

Host cells (e.g., T lymphocytes and NK cells) can be activated by inducing a change in their biologic state by which the cells express activation markers, produce cytokines, proliferate and/or become cytotoxic to target cells. All these changes can be produced by primary stimulatory signals. Co-stimulatory signals amplify the magnitude of the primary signals and suppress cell death following initial stimulation resulting in a more durable activation state and thus a higher cytotoxic capacity.

T cells can be activated generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the T cell based host cells can be activated by binding to an agent that activates CD3ζ.

In other embodiments, a CD2-binding agent may be used to provide a primary stimulation signal to the T cells. For example, and not by limitation, CD2 agents include, but are not limited to, CD2 ligands and anti-CD2 antibodies, e.g., the Tl 1.3 antibody in combination with the Tl 1.1 or Tl 1.2 antibody (Meuer, S. C. et al. (1984) Cell 36:897-906) and the 9.6 antibody (which recognizes the same epitope as Tl 1.1) in combination with the 9-1 antibody (Yang, S. Y. et al. (1986) J. Immunol. 137:1097-1100). Other antibodies which bind to the same epitopes as any of the above described antibodies can also be used.

In certain embodiments, the host cells are activated by administering phorbol myristate acetate (PMA) and ionomycine. In certain embodiments, the host cells are activated by administering an appropriate antigen that induces activation and then expansion. In certain embodiments, PMA, ionomycin, and/or appropriate antigen are administered with CD3 induce activation and/or expansion.

In general, the activating agents used in the present invention includes, but is not limited to, an antibody, a fragment thereof and a proteinaceous binding molecule with antibody-like functions. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., FEBS Lett (1997) 409, 437-441), decabodies (Stone, E., et al., Journal of Immunological Methods (2007) 318, 88-94) and other domain antibodies (Holt, L. J., et al., Trends Biotechnol. (2003), 21, 11, 484-490). The divalent antibody fragment may be an (Fab)2'-fragment, or a divalent single-chain Fv fragment while the monovalent antibody fragment may be selected from the group consisting of a Fab fragment, a Fv fragment, and a single-chain Fv fragment (scFv).

In certain embodiments, one or more binding sites of the CD3ζ agents may be a bivalent proteinaceous artificial binding molecule such as a dimeric lipocalin mutein (i.e., duocalin). In certain embodiments the receptor binding reagent may have a single second binding site, (i.e., monovalent). Examples of monovalent agents include, but are not limited to, a monovalent antibody fragment, a proteinaceous binding molecule with antibody-like binding properties or an MHC molecule. Examples of monovalent antibody fragments include, but are not limited to a Fab fragment, a Fv fragment, and a single-chain Fv fragment (scFv), including a divalent single-chain Fv fragment.

The agent that specifically binds CD3 includes, but is not limited to, an anti-CD3-antibody, a divalent antibody fragment of an anti-CD3 antibody, a monovalent antibody fragment of an anti-CD3-antibody, and a proteinaceous CD3-binding molecule with antibody-like binding properties. A proteinaceous CD3-binding molecule with antibody-like binding properties can be an aptamer, a mutein based on a polypeptide of the lipocalin family, a glubody, a protein based on the ankyrin scaffold, a protein based on the crystalline scaffold, an adnectin, and an avimer. It also can be coupled to a bead.

In certain embodiments, the activating agent (e.g., CD3-binding agents) can be present in a concentration of about 0.1 to about 10 μg/ml. In certain embodiments, the activating agent (e.g., CD3-binding agents) can be present in a concentration of about 0.2 μg/ml to about 9 μg/ml, about 0.3 μg/ml to about 8 μg/ml, about 0.4 μg/ml to about 7 μg/ml, about 0.5 μg/ml to about 6 μg/ml, about 0.6 μg/ml to about 5 μg/ml, about 0.7 μg/ml to about 4 μg/ml, about 0.8 μg/ml to about 3 μg/ml, or about 0.9 μg/ml to about 2 μg/ml. In certain embodiments, the activating agent (e.g., CD3-binding agents) is administered at a concentration of about 0.1 μg/ml, about 0.2 μg/ml, about 0.3 μg/ml, about 0.4 μg/ml, about 0.5 μg/ml, about 0.6 μg/ml, about 0.7 μg/ml, about 0.8 μM, about 0.9 μg/ml, about 1 μg/ml, about 2 μg/ml, about 3 μg/ml, about 4 μM, about 5 μg/ml, about 6 μg/ml, about 7 μg/ml, about 8 μg/ml, about 9 μg/ml, or about 10 μg/ml. In certain embodiments, the CD3-binding agents can be present in a concentration of 1 μg/ml.

NK cells can be activated generally using methods as described, for example, in U.S. Pat. Nos. 7,803,376, 6,949,520, 6,693,086, 8,834,900, 9,404,083, 9,464,274, 7,435,596, 8,026,097, and 8,877,182; U.S. Patent Applications US2004/0058445, US2007/0160578, US2013/0011376, US2015/0118207, and US2015/0037887; and PCT Patent Application WO2016/122147, each of which is incorporated herein by reference in its entirety.

In certain embodiments, the NK based host cells can be activated by, for example and not limitation, inhibition of inhibitory receptors on NK cells (e.g., KIR2DL1, KIR2DL2/3, KIR2DL4, KIR2DL5A, KIR2DL5B, KIR3DL1, KIR3DL2, KIR3DL3, LILRB1, NKG2A, NKG2C, NKG2E or LILRB5 receptor).

In certain embodiments, the NK based host cells can be activated by, for example and not limitation, feeder cells (e.g., native K562 cells or K562 cells that are genetically modified to express 4-1BBL and cytokines such as IL15 or IL21).

In other embodiments, interferons or macrophage-derived cytokines can be used to activate NK cells. For example and not limitation, such interferons include but are not limited to interferon alpha and interferon gamma, and such cytokines include but are not limited to IL-15, IL-2, IL-21.

In certain embodiments, the NK activating agent can be present in a concentration of about 0.1 to about 10 μg/ml. In certain embodiments, the NK activating agent can be present in a concentration of about 0.2 μg/ml to about 9 μg/ml, about 0.3 μg/ml to about 8 μg/ml, about 0.4 μg/ml to about 7 μg/ml, about 0.5 μg/ml to about 6 μg/ml, about 0.6 μg/ml to about 5 μg/ml, about 0.7 μg/ml to about 4 μg/ml, about 0.8 μg/ml to about 3 μg/ml, or about 0.9 μg/ml to about 2 μg/ml. In certain embodiments, the NK activating agent is administered at a concentration of about 0.1 μg/ml, about 0.2 μg/ml, about 0.3 μg/ml, about 0.4 μg/ml, about 0.5 μg/ml, about 0.6 μg/ml, about 0.7 μg/ml, about 0.8 μM, about 0.9 μg/ml, about 1 μg/ml, about 2 μg/ml, about 3 μg/ml, about 4 μM, about 5 μg/ml, about 6 μg/ml, about 7 μg/ml, about 8 μg/ml, about 9 μg/ml, or about 10 μg/ml. In certain embodiments, the NK activating agent can be present in a concentration of 1 μg/ml.

In certain embodiments, the activating agent is attached to a solid support such as, but not limited to, a bead, an absorbent polymer present in culture plate or well or other matrices such as, but not limited to, Sepharose or glass; may be expressed (such as in native or recombinant forms) on cell surface of natural or recombinant cell line by means known to those skilled in the art.

Polynucleotide Transfer

In certain embodiments, the host cells are genetically modified to express a CAR described above. The host cells can be genetically modified after stimulation/activation. In certain embodiments, the host cells are modified within 12 hours, 16 hours, 24 hours, 36 hours, or 48 hours of stimulation/activation. In certain embodiments, the cells are modified within 16 to 24 hours after stimulation/activation. In certain embodiments, the host cells are modified within 24 hours.

In order to genetically modify the host cell to express the CAR, the CAR polynucleotide construct must be transferred into the host cell. Polynucleotide transfer may be via viral or non-viral gene methods. Suitable methods for polynucleotide delivery for use with the current methods include any method known by those of skill in the art, by which a polynucleotide can be introduced into an organelle, cell, tissue or organism.

In some embodiments, polynucleotides are transferred to the cell in a non-viral vector. In some embodiments, the non-viral vector is a transposon. Exemplary transposons hat can be used in the present invention include, but are not limited to, a sleeping beauty transposon and a PiggyBac transposon.

Nucleic acid vaccines can be used to transfer CAR polynucleotides into the host cells. Such vaccines include, but are not limited to non-viral polynucleotide vectors, "naked" DNA and RNA, and viral vectors. Methods of genetically modifying cells with these vaccines, and for optimizing the expression of genes included in these vaccines are known to those of skill in the art.

In certain embodiments, the host cells can be genetically modified by methods ordinarily used by one of skill in the art. In certain embodiments, the host cells can be transduced via retroviral transduction. References describing retroviral transduction of genes are Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993).

One method of genetic modification includes ex vivo modification. Various methods are available for transfecting cells and tissues removed from a subject via ex vivo modification. For example, retroviral gene transfer in vitro can be used to genetically modified cells removed from the subject and the cell transferred back into the subject. See e.g., Wilson et al., *Science,* 244:1344-1346, 1989 and Nabel et al., *Science,* 244(4910):1342-1344, 1989, both of which are incorporated herein by reference in their entity. In certain embodiments, the host cells may be removed from the subject and transfected ex vivo using the polynucleotides (e.g., expression vectors) of the invention. In certain embodiments, the host cells obtained from the subject can be transfected or transduced with the polynucleotides (e.g., expression vectors) of the invention and then administered back to the subject.

Another method of gene transfer includes injection. In certain embodiments, a cell or a polynucleotide or viral vector may be delivered to a cell, tissue, or organism via one or more injections (e.g., a needle injection). Non-limiting methods of injection include injection of a composition (e.g., a saline based composition). Polynucleotides can also be introduced by direct microinjection. Non-limiting sites of injection include, subcutaneous, intradermal, intramuscular, intranodal (allows for direct delivery of antigen to lymphoid tissues). intravenous, intraprotatic, intratumor, intralymphatic (allows direct administration of DCs) and intraperitoneal. It is understood that proper site of injection preparation is necessary (e.g., shaving of the site of injection to observe proper needle placement).

Electroporation is another method of polynucleotide delivery. See e.g., Potter et al., (1984) *Proc. Nat'l Acad. Sci. USA,* 81, 7161-7165 and Tur-Kaspa et al., (1986) *Mol. Cell Biol.,* 6, 716-718, both of which are incorporated herein in their entirety for all purposes. Electroporation involves the exposure of a suspension of cells and DNA to a high-voltage electric discharge. In certain embodiments, cell wall-degrading enzymes, such as pectin-degrading enzymes, can be employed to render the host cells more susceptible to genetic modification by electroporation than untreated cells. See e.g., U.S. Pat. No. 5,384,253, incorporated herein by reference in its entirety for all purposes.

In vivo electroporation involves a basic injection technique in which a vector is injected intradermally in a subject. Electrodes then apply electrical pulses to the intradermal site causing the cells localized there (e.g., resident dermal dendritic cells), to take up the vector. These tumor antigen-expressing dendritic cells activated by local inflammation can then migrate to lymph-nodes.

Methods of electroporation for use with this invention include, for example, Sardesai, N. Y., and Weiner, D. B., *Current Opinion in Immunotherapy* 23:421-9 (2011) and Ferraro, B. et al., *Human Vaccines* 7:120-127 (2011), both of which are hereby incorporated by reference herein in their entirety for all purposes.

Additional methods of polynucleotide transfer include liposome-mediated transfection (e.g., polynucleotide entrapped in a lipid complex suspended in an excess of aqueous solution. See e.g., Ghosh and Bachhawat, (1991) In: *Liver Diseases, Targeted Diagnosis and Therapy Using Specific Receptors and Ligands*. pp. 87-104). Also contemplated is a polynucleotide complexed with Lipofectamine, or Superfect); DEAE-dextran (e.g., a polynucleotide is delivered into a cell using DEAE-dextran followed by polyethylene glycol. See e.g., Gopal, T. V., *Mol Cell Biol.* 1985 May; 5(5):1188-90); calcium phosphate (e.g., polynucleotide is introduced to the cells using calcium phosphate precipitation. See e.g., Graham and van der Eb, (1973) *Virology,* 52, 456-467; Chen and Okayama, *Mol. Cell Biol.,* 7(8):2745-2752, 1987), and Rippe et al., *Mol. Cell Biol.,* 10:689-695, 1990); sonication loading (introduction of a polynucleotide by direct sonic loading. See e.g., Fechheimer et al., (1987) *Proc. Nat'l Acad. Sci. USA,* 84, 8463-8467); microprojectile bombardment (e.g., one or more particles may be coated with at least one polynucleotide and delivered into cells by a propelling force. See e.g., U.S. Pat. Nos. 5,550,318; 5,538,880; 5,610,042; and PCT Application WO 94/09699; Klein et al., (1987) *Nature,* 327, 70-73, Yang et al., (1990) *Proc. Nat'l Acad. Sci. USA,* 87, 9568-9572); and receptor-mediated transfection (e.g., selective uptake of macromolecules by receptor-mediated endocytosis that will be occurring in a target cell using cell type-specific distribution of various receptors. See e.g., Wu and Wu, (1987) 1 *Biol. Chem.,* 262, 4429-4432; Wagner et al., *Proc. Natl. Acad. Sci. USA,* 87(9):3410-3414, 1990; Perales et al., *Proc. Natl. Acad. Sci. USA,* 91:4086-4090, 1994; Myers, EPO 0273085; Wu and Wu, *Adv. Drug Delivery Rev.,* 12:159-167, 1993; Nicolau et al., (1987) *Methods Enzymol.,* 149, 157-176), each reference cited here is incorporated by reference in their entirety for all purposes.

In further embodiments, host cells are genetically modified using gene editing with homology-directed repair (HDR). Homology-directed repair (HDR) is a mechanism used by cells to repair double strand DNA breaks. In HDR, a donor polynucleotide with homology to the site of the double strand DNA break is used as a template to repair the cleaved DNA sequence, resulting in the transfer of genetic information from the donor polynucleotide to the DNA. As such, new nucleic acid material may be inserted or copied into a target DNA cleavage site. Double strand DNA breaks in host cells may be induced by a site-specific nuclease. The term "site-specific nuclease" as used herein refers to a nuclease capable of specifically recognizing and cleaving a nucleic acid (DNA or RNA) sequence. Suitable site-specific nucleases for use in the present invention include, but are not limited to, RNA-guided endonuclease (e.g., CRISPR-associated (Cas) proteins), zinc finger nuclease, a TALEN nuclease, or mega-TALEN nuclease. For example, a site-specific nuclease (e.g., a Cas9+guide RNA) capable of inducing a double strand break in a target DNA sequence is introduced to a host cell, along with a donor polynucleotide encoding a CAR of the present disclosure and optionally a safety switch (e.g., CD20).

Expansion/Proliferation

After the host cells are activated and transduced, the cells are cultured to proliferate. T cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of T cells can include interleukins, such as IL-2, IL-7, IL-15, or IL-21 (see for example Cornish et al. 2006, Blood. 108(2):600-8, Bazdar and Sieg, 2007, Journal of Virology, 2007, 81(22): 12670-12674, Battalia et al, 2013, Immunology, 139(1):109-120). Other illustrative examples for agents that may be used for the expansion of T cells are agents that bind to CD8, CD45 or CD90, such as αCD8, αCD45 or αCD90 antibodies. Illustrative examples of T cell population including antigen-specific T cells, T helper cells, cytotoxic T cells, memory T cell (an illustrative example of memory T-cells are CD62L+CD8+ specific central memory T cells) or regulatory T cells (an illustrative example of Treg are CD4+CD25+CD45RA+ Treg cells).

Additional agents that can be used to expand T lymphocytes includes methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; and 6,867,041, each of which is incorporated herein by reference in its entirety.

In certain embodiments, the agent(s) used for expansion (e.g., IL-2) are administered at about 20 units/ml to about 200 units/ml. In certain embodiments, the agent(s) used for expansion (e.g., IL-2) are administered at about 25 units/ml to about 190 units/ml, about 30 units/ml to about 180 units/ml, about 35 units/ml to about 170 units/ml, about 40 units/ml to about 160 units/ml, about 45 units/ml to about 150 units/ml, about 50 units/ml to about 140 units/ml, about 55 units/ml to about 130 units/ml, about 60 units/ml to about 120 units/ml, about 65 units/ml to about 110 units/ml, about 70 units/ml to about 100 units/ml, about 75 units/ml to about 95 units/ml, or about 80 units/ml to about 90 units/ml. In certain embodiments, the agent(s) used for expansion (e.g., IL-2) are administered at about 20 units/ml, about 25 units/ml, about 30 units/ml, 35 units/ml, 40 units/ml, 45 units/ml, about 50 units/ml, about 55 units/ml, about 60 units/ml, about 65 units/ml, about 70 units/ml, about 75 units/ml, about 80 units/ml, about 85 units/ml, about 90 units/ml, about 95 units/ml, about 100 units/ml, about 105 units/ml, about 110 units/ml, about 115 units/ml, about 120 units/ml, about 125 units/ml, about 130 units/ml, about 135 units/ml, about 140 units/ml, about 145 units/ml, about 150 units/ml, about 155 units/ml, about 160 units/ml, about 165 units/ml, about 170 units/ml, about 175 units/ml, about 180 units/ml, about 185 units/ml, about 190 units/ml, about 195 units/ml, or about 200 units/ml. In certain embodiments, the agent(s) used for expansion (e.g., IL-2) are administered at about 5 mg/ml to about 10 ng/ml. In certain embodiments, the agent(s) used for expansion (e.g., IL-2) are administered at about 5.5 ng/ml to about 9.5 ng/ml, about 6 ng/ml to about 9 ng/ml, about 6.5 ng/ml to about 8.5 ng/ml, or about 7 ng/ml to about 8 ng/ml. In certain embodiments, the agent(s) used for expansion (e.g., IL-2) are administered at about 5 ng/ml, 6 ng/ml, 7 ng/ml, 8 ng/ml, 9, ng/ml, or 10 ng/ml.

After the host cells are activated and transduced, the cells are cultured to proliferate. NK cells may be cultured for at least 1, 2, 3, 4, 5, 6, or 7 days, at least 2 weeks, at least 1, 2, 3, 4, 5, or 6 months or more with 1, 2, 3, 4, 5, 6, 7, 8, 9, or 10 or more rounds of expansion.

Agents that can be used for the expansion of natural killer cells can include agents that bind to CD16 or CD56, such as for example αCD16 or αCD56 antibodies. In certain embodiments, the binding agent includes antibodies (see for example Hoshino et al, Blood. 1991 Dec. 15; 78(12):3232-40). Other agents that may be used for expansion of NK cells may be IL-15 (see for example Vitale et al. 2002. The Anatomical Record. 266:87-92, which is hereby incorporated by reference in its entirety for all purposes).

Conditions appropriate for T cell culture include an appropriate media (e.g., Minimal Essential Media (MEM), RPMI Media 1640, Lonza RPMI 1640, Advanced RPMI, Clicks, AIM-V, DMEM, a-MEM, F-12, TexMACS, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion).

Examples of other additives for host cell expansion include, but are not limited to, surfactant, piasmanate, pH buffers such as HEPES, and reducing agents such as N-acetyl-cysteine and 2-mercaptoethanol, Antibiotics (e.g., penicillin and streptomycin), are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

Pharmaceutical Compositions

In some embodiments, the compositions comprise one or more polypeptides of the CARs and other related molecules (e.g., CD20 or anti-CD20 antibody), polynucleotides, vectors comprising same, and cell compositions, as disclosed herein. Compositions of the present disclosure include, but are not limited to pharmaceutical compositions.

In one aspect, the present disclosure provides a pharmaceutical composition comprising a polynucleotide or a recombinant vector described herein, and a pharmaceutically accepted carrier and/or excipient.

In another aspect, the present disclosure provides pharmaceutical composition comprising the CAR-modified host cells described herein and a pharmaceutically acceptable carrier and/or excipient.

Examples of pharmaceutical carriers include but are not limited to sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions.

Compositions comprising CAR-modified host cells disclosed herein may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions comprising CAR-modified host cells disclosed herein may comprise one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

In some embodiments, the compositions are formulated for parenteral administration, e.g., intravascular (intravenous or intraarterial), intraperitoneal, intratumoral, intraventricular, intrapleural or intramuscular administration. The parenteral preparation can be enclosed in ampoules, disposable syringes or multiple dose vials made of glass or plastic. An injectable pharmaceutical composition is preferably sterile. In some embodiments, the composition is reconstituted from a lyophilized preparation prior to administration.

In some embodiments, the CAR-modified host cells may be mixed with substances that adhere or penetrate then prior to their administration, e.g., but not limited to, nanoparticles.

Therapeutic Methods

In one aspect, the present disclosure provides a method for treating a cancer in a subject in need thereof. A therapeutically effective amount of the CAR-modified host cells described herein or the pharmaceutical composition comprising the host cells is administered to the subject.

The terms "cancer" and "cancerous" refer to or describe the physiological condition in mammals that is typically characterized by unregulated cell growth. The term "cancer" includes, for example, the soft tissue tumors (e.g., lymphomas), and tumors of the blood and blood-forming organs (e.g., leukemias), and solid tumors, which is one that grows in an anatomical site outside the bloodstream (e.g., carcinomas). Examples of cancer include, but are not limited to, carcinoma, lymphoma, blastoma, sarcoma (e.g., osteosarcoma or rhabdomyosarcoma), and leukemia or lymphoid malignancies. More particular examples of such cancers include squamous cell cancer (e.g., epithelial squamous cell cancer), adenosquamous cell carcinoma, lung cancer (e.g., including small-cell lung cancer, non-small cell lung cancer, adenocarcinoma of the lung, squamous carcinoma of the lung), cancer of the peritoneum, hepatocellular cancer, gastric or stomach cancer (e.g., including gastrointestinal cancer, pancreatic cancer), cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulvar cancer, thyroid cancer, hepatic carcinoma, anal carcinoma, penile carcinoma, primary or metastatic melanoma, multiple myeloma and B-cell lymphoma, non-Hodgkin's lymphoma, Hodgkin's lymphoma, brain (e.g., high grade glioma, diffuse pontine glioma, ependymoma, neuroblastoma, or glioblastoma), as well as head and neck cancer, and associated metastases. Additional examples of cancer can be found in The Merck Manual of Diagnosis and Therapy, 19th Edition, § on Hematology and Oncology, published by Merck Sharp & Dohme Corp., 2011 (ISBN 978-0-911910-19-3); The Merck Manual of Diagnosis and Therapy, 20th Edition, § on Hematology and Oncology, published by Merck Sharp & Dohme Corp., 2018 (ISBN 978-0-911-91042-1) (2018 digital online edition at internet website of Merck Manuals); and SEER Program Coding and Staging Manual 2016, each of which are incorporated by reference in their entirety for all purposes.

In some embodiments, host cells modified with a CD123-binding CAR, or pharmaceutical compositions thereof, are administered to a subject to treat a cancer expressing CD123. The CD123+ cancer may be an acute myeloid leukemia (AML), an acute lymphoblastic leukemia (ALL), a blastic plasmacytoid dendritic neoplasm (BPCDN), or a hairy cell leukemia. In some embodiments, the cancer is an acute myeloid leukemia (AML). In some embodiments, the cancer is an acute lymphoblastic leukemia (ALL). In other embodiments, the modified host cells can also be used to target normal cells that express CD123, including but not limited to hematopoietic progenitor cells as part of a hematopoietic cell transplant (HCT).

In some embodiments, host cells modified with an IL13Rα2-binding CAR, or pharmaceutical compositions thereof, are administered to a subject to treat a cancer expressing IL13Rα2. The IL13Rα2+ cancer may be a brain cancer such as glioblastoma, a colon cancer, a renal cell carcinoma, a pancreatic cancer, a melanoma, a head and neck cancer, a mesothelioma, or an ovarian cancer.

In cases where the CAR-modified host cells also express a CD20 polypeptide, the method may further include administering an anti-CD20 antibody to the subject for removal of the isolated host cells. The anti-CD20 antibody is administered in an amount effective for sufficient removal of the isolated host cells from the subject. In some embodiments, the anti-CD20 antibody is administered in an amount effective for removal of more than 50% of the isolated host cells from the subject. For example, the anti-CD20 antibody may be administered in an amount effective for removal of more than 55%, more than 60%, more than 65%, more than 70%, more than 75%, more than 80%, more than 85%, more than 90%, more than 95%, more than 98%, more than 99%, or about 100% of the isolated host cells from the subject. The anti-CD20 antibody may be administered in an amount effective for removal of about 50% to about 70%, about 60% to about 80%, about 70% to about 90%, or about 80% to about 100% of the isolated host cells from the subject.

Non-limiting examples of anti-CD20 antibodies that can be used for removal the isolated host cells include Rituximab, Ibritumomab tiuxetan, Tositumomab, Ofatumumab, Ocrelizumab, TRU-015, Veltuzumab, AME-133v, PRO131921, and Obinutuzumab. In some embodiments, the anti-CD20 antibody is Rituximab.

In some embodiments, the therapeutic method of the present disclosure includes one or more of the following steps: (a) isolating immune cells from the subject or donor; (b) modifying the immune cells ex vivo with a polynucleotide encoding a CAR and optionally a CD20 polypeptide, or a recombinant vector comprising the same; (c) optionally, expanding and/or activating the modified immune cells before, after and/or during step (b); (d) introducing a therapeutically effective amount of the modified immune cells into the subject, and (e) in cases when the modified immune cells comprise CD20, optionally, administering an anti-CD20 antibody to the subject, wherein the anti-CD20 antibody is administered in an amounts effective for removal of the modified immune cells from the subject. The immune cells may be T cells and/or NK cells.

In some embodiments, the modified host cell is an autologous cell. In some embodiments, the modified host cell is an allogeneic cell. In cases where the host cell is isolated from a donor, the method may further include a method to prevent graft vs host disease (GVHD) and the host cell rejection.

In some embodiments of any of the therapeutic methods described above, the composition is administered in a therapeutically effective amount. The dosages of the composition administered in the methods of the invention will vary widely, depending upon the subject's physical parameters, the frequency of administration, the manner of administration, the clearance rate, and the like. The initial dose may be larger, and might be followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve in vivo persistence of modified host cells. It is also contemplated that a variety of doses will be effective to improve in vivo effector function of modified host cells.

In some embodiments, composition comprising the modified host cells manufactured by the methods described herein may be administered at a dosage of $10^2$ to $10^{10}$ cells/kg body weight, $10^5$ to $10^9$ cells/kg body weight, $10^5$ to $10^8$ cells/kg body weight, $10^5$ to $10^7$ cells/kg body weight, $10^7$ to $10^9$ cells/kg body weight, or $10^7$ to $10^8$ cells/kg body weight, including all integer values within those ranges. The number of modified host cells will depend on the therapeutic use for which the composition is intended for.

Modified host cells may be administered multiple times at dosages listed above. The modified host cells may be allogeneic, syngeneic, xenogeneic, or autologous to the patient undergoing therapy.

The compositions and methods described in the present disclosure may be utilized in conjunction with other types of therapy for cancer, such as chemotherapy, surgery, radiation, gene therapy, and so forth.

It is also contemplated that when used to treat various diseases/disorders, the compositions and methods of the present disclosure can be utilized with other therapeutic methods/agents suitable for the same or similar diseases/disorders. Such other therapeutic methods/agents can be co-administered (simultaneously or sequentially) to generate additive or synergistic effects. Suitable therapeutically effective dosages for each agent may be lowered due to the additive action or synergy.

In some embodiments of any of the above therapeutic methods, the method further comprises administering to the subject one or more additional compounds selected from the group consisting of immuno-suppressives, biologicals, probiotics, prebiotics, and cytokines (e.g., IFN or IL-2).

As a non-limiting example, the invention can be combined with other therapies that block inflammation (e.g., via blockage of ILL INFα/β, IL6, TNF, IL23, etc.).

The methods and compositions of the invention can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 4-1BB, OX40, etc.). The methods of the invention can be also combined with other treatments that possess the ability to modulate NKT function or stability, including but not limited to CD1d, CD1d-fusion proteins, CD dimers or larger polymers of CD either unloaded or loaded with antigens, CD1d-chimeric antigen receptors (CD1d-CAR), or any other of the five known CD1 isomers existing in humans (CD1a, CD1b, CD1c, CD1e). The methods of the invention can also be combined with other treatments such as midostaurin, enasidenib, or a combination thereof.

Therapeutic methods of the invention can be combined with additional immunotherapies and therapies. For example, when used for treating cancer, the compositions of the invention can be used in combination with conventional cancer therapies, such as, e.g., surgery, radiotherapy, chemotherapy or combinations thereof, depending on type of the tumor, patient condition, other health issues, and a variety of factors. In certain aspects, other therapeutic agents useful for combination cancer therapy with the inhibitors of the invention include anti-angiogenic agents. Many anti-angiogenic agents have been identified and are known in the art, including, e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000). In one embodiment, the modified host cells of the invention can be used in combination with a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof (e.g., anti-hVEGF antibody A4.6.1, bevacizumab or ranibizumab).

Non-limiting examples of chemotherapeutic compounds which can be used in combination treatments of the present disclosure include, for example, aminoglutethimide, amsacrine, anastrozole, asparaginase, azacitidine, bcg, bicalutamide, bleomycin, buserelin, busulfan, campothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, decitabine, dienestrol, diethylstilbestrol, docetaxel, doxorubicin, epirubicin, estradiol, estramnustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, ironotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, octreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic compounds may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers and caspase activators; and chromatin disruptors.

In various embodiments of the methods described herein, the subject is a human. The subject may be a juvenile or an adult, of any age or sex.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Below are the methods and materials used in the Examples.

Cells and Culture Conditions

De-identified apheresis products from healthy donors were purchased from Key Biologics (Memphis, TN; Cat #16761) and were used in accordance with the Helsinki Declaration. Authenticated K562 and Molm13 cell lines were obtained from ATCC. Molm13 expressing a GFP firefly luciferase (Molm13.ffluc) fusion molecule was previously described[38]. All cell lines were cultured in RPMI media (GE Healthcare Life Sciences; Logan, UT; Cat #SH30096.01) supplemented with 10% fetal bovine serum (Gibco/Thermo Fisher Scientific, Waltham, MA; Cat #10082-147) and L-glutamine (GlutaMAX; Gibco/Thermo Fisher Scientific; Cat #35050-061).

Lentiviral Vectors

The LV backbone that was used for this study has been previously described[41] except that the insulators were removed from the self-inactivating (SIN) 3' partially-deleted viral LTRs based on the safety records of LVs in clinical trials[42,43]. The expression cassette of the LV is under the control of the MND promoter (myeloproliferative sarcoma virus enhancer, negative control region deleted, dl587rev primer-binding site substituted)[41]. Mini genes encoding CD20, 2A, and the CD123-specific CARs (FIG. 1A) were synthesized by GeneArt (ThermoFisher, Waltham, MA) and subcloned by standard techniques. All cloned CD20-2A-CD123-CAR constructs were verified by sequencing (Hartwell Center, St. Jude Children's Research Hospital, Memphis, TN). Purified lentiviral particles were produced by St. Jude Children's Research Hospital (SJCRH) Vector Core Laboratory using transient transfection followed by FPLC purification[44].

CD4 and CD8 T-Cell Isolation

CD4+/CD8+ T-cells were magnetically isolated on a CliniMACS Plus instrument (Miltenyi Biotec; Bergisch Gladsbach, Germany) using CD4 (Miltenyi Biotec; Cat. #130-030-401), and CD8 microbeads (Miltenyi Biotec; Cat. #130-030-801) and the enrichment program 1.1 as per manufacturer's instructions. Aliquots of enriched CD4+/CD8+ T-cells were cryopreserved and thawed prior to use for CAR T-cell generation.

CD123-CAR$^{CD20}$ T-Cell Generation

Enriched CD4+/CD8+ T-cells were resuspended at $1\times10^6$ per ml in X-VIVO 15 (Lonza, Walkersville, MD; Cat #04-744Q) supplemented with 5% human AB serum (Corning; Corning, NY; Cat #35-060-CI) and 10 ng/ml each IL7 and IL15 (Miltenyi Biotec; Cat #170-076-111 and 170-076-114, respectively). Cells were activated by plating overnight with T-cell TransAct (Miltenyi Biotec; Cat #130-019-011). On day 1, $2\times10^6$ T-cells were plated with lentiviral vector and transduced overnight at a MOI of 10 to 12. After transduction, cells were transferred to 6-well G-Rex plates (Wilson Wolf; New Brighton, MN; Cat #180102-1) and expanded for 7-10 days. On day 6 half the media was removed and replaced with complete media plus cytokines.

Vector Copy Number

Transduced T-cells were harvested, and total genomic DNA was isolated using the Zymo Research quick-DNA 96 kit (Zymo Research, Irvine, CA; Cat #D3012). To determine the vector copy number (VCN) per cell, genomic DNA was digested with MspI and used as a template in PCR using a digital droplet PCR instrument (QX200 Bio-Rad, Carlsbad, CA). The following primer-probe sets were used to amplify the HIV psi sequence located on the vector genome and the endogenous control gene, RPP30, 5'-ACTTGAAAGCGAAAGGGAAAC-3' (SEQ ID NO: 80), 5'-CACCCATCTCTCTCCTTCTAGCC-3' (SEQ ID NO: 81) and probe 5'FAM-AGCTCTCTCGACGCAGGACTCGGC-3' (SEQ ID NO: 82) and 5'-GCGGCTGTCTCCACAAGT-3' (SEQ ID NO: 83), 5'-GATTTGGACCTGCGAGCG-3' (SEQ ID NO: 84) and probe 5'HEX-CTGACCTGAAGGCTCT-3' (SEQ ID NO: 85), respectively. The reaction mixture contained ddPCR Supermix for probes without UTP (BioRad; Cat #64180520). The cycled droplets were read with the QX200 droplet reader (Bio-Rad). The ratio of the numbers of molecules of these two genes is the sample's gene of interest relative copy number analyzed with QuantaSoft droplet reader software version 1.7.4.0917 (Bio-Rad).

Flow Cytometry

Cells were stained with fluorochrome-conjugated primary antibodies for 30 min at 4° C. and washed with FACS buffer (2% FBS in 1×PBS) prior to analysis. For CAR staining cells were washed with 1×PBS twice then incubated with a recombinant CD123-Fc fusion protein (abcam; Cat #ab88358) in PBS for 30 minutes at 4° C., washed, incubated with the secondary antibody in FACS buffer for 30 minutes at 4° C. and washed with FACS buffer prior to analysis. Stained cells were run on a CytoFLEX analyzer (Beckman Coulter; Indianapolis, IN) and analysis was done using FlowJo software. The following antibodies were used: CD4 (Clone OKT4; BV785, BioLegend Cat #317442); CD8 (Clone SK1; APC-Cy7; BD Pharmingen Cat #557834); CCR7 (Clone REA546; PE; Miltenyi Cat #130-108-285); CD45RO (Clone UCHL1; APC; Tonbo Cat #20-0457-T100); Tim3 (Clone F38-2E2; PE-Cy7; Biolegend Cat #345014); PD1 (Clone EH12.2H7; BV421; Biolegend Cat #329920); CD20 (Clone 2H7; FITC; Tonbo Cat #35-0209-T100); Goat anti-human Fc-IgG (pooled goat antisera; PE; Southern Biotech Cat #2048-09).

Cytotoxicity Assay

Cytotoxic activity was evaluated using a flow-cytometry-based assay. Target cells were labelled with CFSE (Cayman Chemical; Ann Arbor MI; Cat #600120) for 20 minutes at 37° C. 50,000 CFSE labeled target cells were incubated overnight either alone or with effector T-cells in round bottom 96-well plates (Corning; Corning, NY; Ref #353077) at an E:T ratio of 3:1. Cells were washed and resuspended in PBS containing Count Bright Absolute Counting Beads (Life Technologies; Eugene OR, Ref #C36950). CFSE was measured by flow cytometry on a BD FACSLyric (Becton Dickinson; Franklin Lakes, NJ) and analyzed with FlowJo software (Becton Dickinson). Lysis was calculated with the following formula: % lysis=100−(Average CFSE+ events per 100 beads/Average of CFSE+ events per 100 beads in wells with target alone)*100.

Cytokine Production

Effector cells were cultured at a 2:1 ratio with target cells or in the presence of media alone for 24 hours in a 24-well plate (Corning; Ref #353047). Supernatant was collected and IFNγ was determined using a Quantikine ELISA kit (R&D; Minneapolis, MN, Cat3 SIF50), according to manufacturer's instructions.

CFU Assay

An apheresis product of mobilized peripheral blood was purchased from Key Biologics (Memphis, TN) and CD34+ cells were isolated by SJCRH's Human Applications Laboratory using the CliniMACS device per manufacturer's instructions (Miltenyi Biotec). A modified colony forming assay (CFU) was done. In brief, CD34+ cells ($5\times10^4$) were incubated with CD123-CAR$^{CD20}$ T-cells at ratios of 5:1 and 1:1 (T:CD34) for 4 hours in 96-well round-bottom plates. For each co-culture, 3 replicates (input equivalent of 2000 CD34+ cells) were plated into 1 ml MethoCult H4434 (Stem Cell Technologies; Vancouver, BC, Canada; Cat #04434) following manufacturer's instructions. Colonies were counted 12-14 days later.

Safety Switch Activation Assay

T-cells were resuspended in RPMI/1% human serum (Corning, Cat #35-060-CI; heat inactivated) and incubated for 1 hour at 37° C. with 10 □g Rituximab (Rituxan®, Biogen; Cambridge, MA; Cat #502-051021) and 10% baby rabbit complement (Cedarlane; Burlington, NC; Cat #CL3441) in a 96-well round bottom plate as previously published[38]. Cells were washed and analyzed by flow cytometry for CD20 expression. % Transgene expression was determined by the following formula: (% $CD20^{+}_{before}$−% $CD20^{+}_{after}$)/% $CD20^{+}_{before}$ X(1−% $CD20^{+}_{after}$).

Xenograft Model

In vivo experiments were performed under a protocol approved by SJCRH Institutional Animal Care and Use Committee (IACUC). Animals were housed in specific pathogen free rooms for the duration of the experiments. Female NSG mice (NOD-scid IL2Rgamma$^{null}$, NOD-scid IL2Rg$^{null}$, NSG, NOD scid gamma) were obtained from the SJCRH breeding colony at 8-10 weeks of age. Mice received $5\times10^3$ Molm13 tumor cells modified to express a GFP.ffluc fusion gene (Molm13ffluc) i.v. (tail vein injection). Seven days later, mice in the treatment groups were infused with effector cells. Animals receiving tumor only were used as controls. Serial imaging was performed subsequently. The mice were imaged at the SJCRH Center for In Vivo Imaging and Therapeutics using the Xenogen IVIS®-200 imaging system (IVIS, Xenogen Corp., Alameda, CA) as previously described[45], and euthanized at predefined endpoints or when they met euthanasia criteria in accordance with SJCRH's Animal Resource Center.

Statistics

Data were summarized using descriptive statistics. A Friedman or permutation test was used to examine overall differences in in continuous variables between lentiviral CD123-CAR$^{CD20}$ constructs. The overall test was followed by pairwise comparisons using the Wilcoxon signed rank or paired permutation test when appropriate. A two-way repeated-measures analysis of variance (ANOVA) with a rank transformation was used to examine overall differences in continuous variables. A Friedman test was used to examine the overall differences in CD4:CD8 ratios between constructs. The overall test was followed by pairwise comparisons using the Wilcoxon signed rank test when appropriate (i.e. overall test $P<0.05$). Next, constructs were compared to control using the Wilcoxon signed rank test. The CD4:CD8 ratio for each construct was compared to a value of 1 using the Wilcoxon signed rank test (i.e. null: ratio=1; alternative: ratio 1). The bias-corrected and accelerate (BCa) bootstrap confidence intervals are reported for the median ratio for each construct. The Kruskal-Wallis test was used to examine overall differences in bioluminescence on day 12 between constructs. The overall test was followed by pairwise comparisons using the Wilcoxon rank sum test. A two-way repeated measure analysis of variance (ANOVA) with a rank transformation was used to examine overall differences in bioluminescence over time and between constructs. Time, construct, and their interaction were considered in the model. Survival was compared between constructs using the Wilcoxon rank sum test. Statistical analyses were conducted with R 3.6.0 software (Lucent technologies, Murray Hill, New Providence NJ).

Example 1. Generation and Characterization of a CD123-CAR$^{CD20}$ Construct

A bicistronic lentivirus (LV) encoding CD20, a 2A sequence, and a CD123-CAR was generated. The CD123-CAR (termed CD8α.41BBz) comprises a CD123-specific single chain variable sequence (scFv) derived from antibody 26292 (292), a CD8α hinge/transmembrane domain, a 4-1BB costimulatory domain, and the CD3 (z) signaling domain. FIG. 1A shows a schematic of the CD8α.41BBz CAR$^{CD20}$ viral vector.

T cells were selected based on CD4/CD8 expression and were activated by stimulation with CD3/CD28 antibodies or TransAct™ in the presence of cytokines (IL-7 and IL-15) one day prior to the viral transduction. T cells were transduced with the lentivirus encoding the CD8α.41BBz CAR$^{CD20}$. Transduced T cells were maintained and expanded in the presence of cytokines and were frozen at Day 7-10. FIG. 1B shows a summary of the transduction process.

Figure 1C:
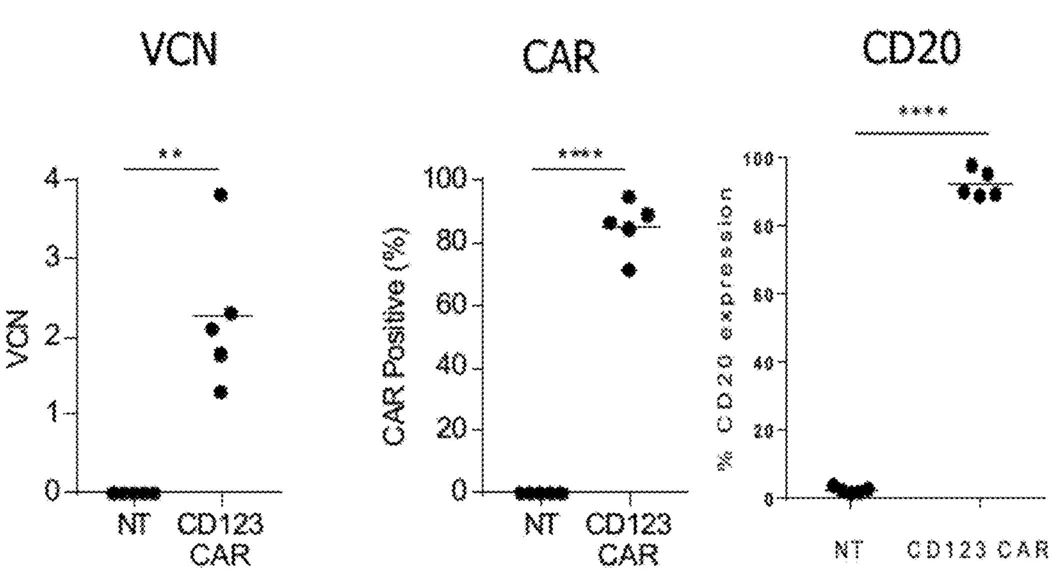

Viral Copy Number (VCN) was measured in the transduced CD123-CAR T cells by digital droplet PCR. There was a significant increase in VCN of transduced CD123-CAR T cells as compared to non-transduced (NT) T cells (n=5; $p<0.01$ (); FIG. 1C left). CD123-CAR and CD20 expression in CD123-CAR T cells was evaluated via fluorescence-activated cell sorting (FACS) using a standard flow cytometer and commercially available antibodies to detect CD20 and CAR expression. Significant higher expression of CD123-CAR and CD20 as compared to NT T cells (n=5; $p<0.0001$ (**)) was observed (FIG. 1C middle and right). These results confirmed that the T cells were successful transduced with the lentivirus encoding the CD8α.41BBz CAR.

Figure 1D:
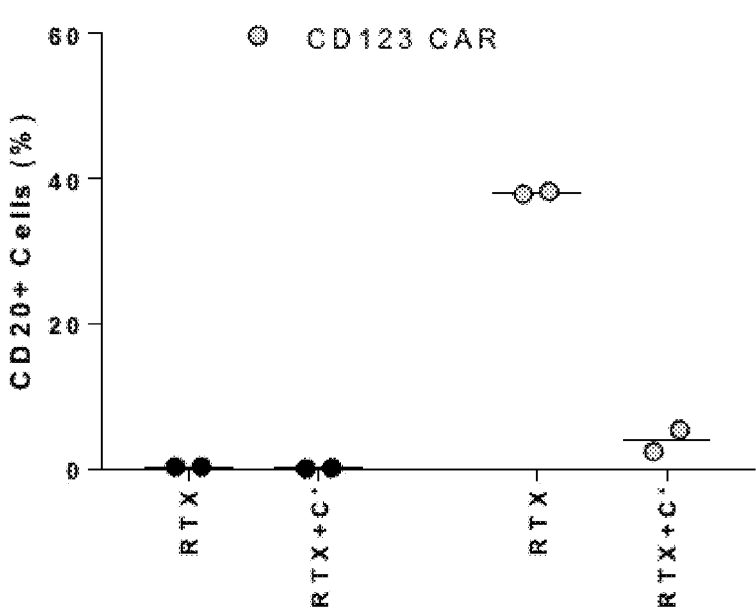

NT or CD123-CAR T cells were incubated with rituximab only or with rituximab+ complement. CD20+ cell number was determined by flow cytometry after 1 hour. The number of CD20+ cells decreased by over 30% after treatment with rituximab and complement as compared to rituximab treatment alone (FIG. 1D).

Figure 1E:
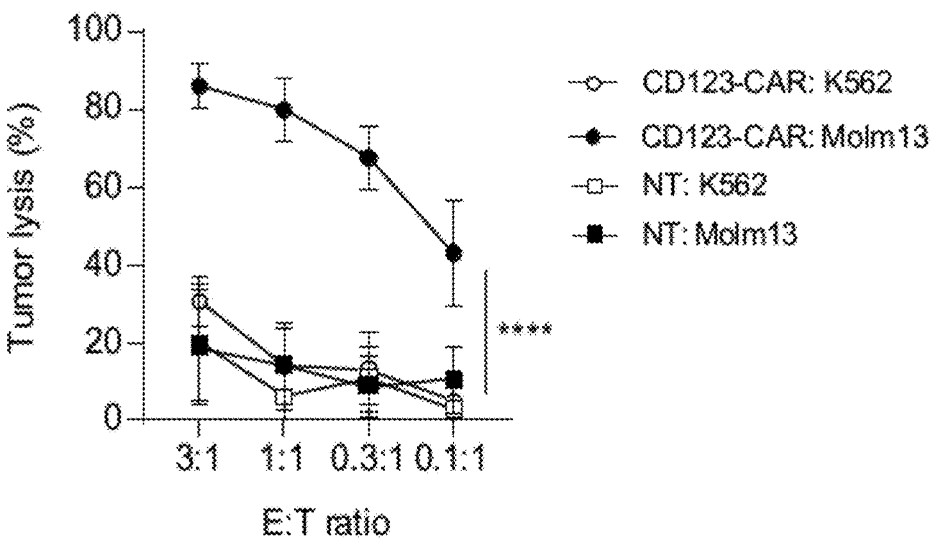

CD123-CAR and NT T cells were incubated with CD123+ (MOLM-13) and CD123− (K562) target cells at different effector to target (E:T) ratios. After 24 hours, live tumor cells were determined by FACS analysis. The assay was performed in triplicates. Significant tumor lysis of MOLM13 target cells was observed when incubated with CD123-CAR T cells vs NT T cells (n=3; p<0.0001 (****); FIG. 1E), confirming antigen specific killing by the CD123-CAR T cells.

Figure 1F:
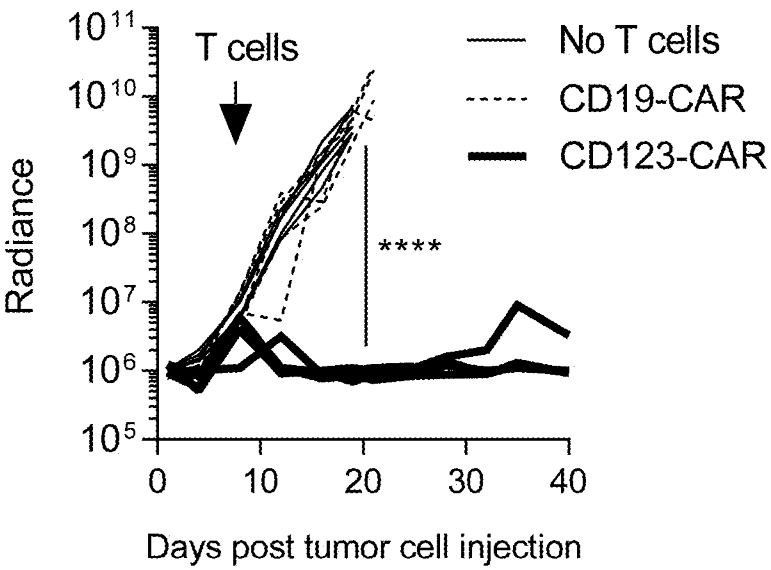

The in vivo activity of CD123-CAR T cells was evaluated in a xenograft AML model. CD123+ MOLM13 (AML) cells expressing firefly luciferase (ffluc) were injected to the NSG mice by intravenously (iv) via tail vein. On Day 5 mice received a single iv dose of CD123-CAR or CD19-CAR T cells. Mice that only received tumor cells served as controls. AML progression was tracked by bioluminescence imaging. A significant reduction of MOLM13 cells was observed in mice that received CD123-CAR T cells vs mice that received no or CD19-CAR T cells (n=5; p<0.0001 (****); FIG. 1F).

Example 2. CD8α.41BBz CAR Results in "Tonic Signaling"

Figure 2A:
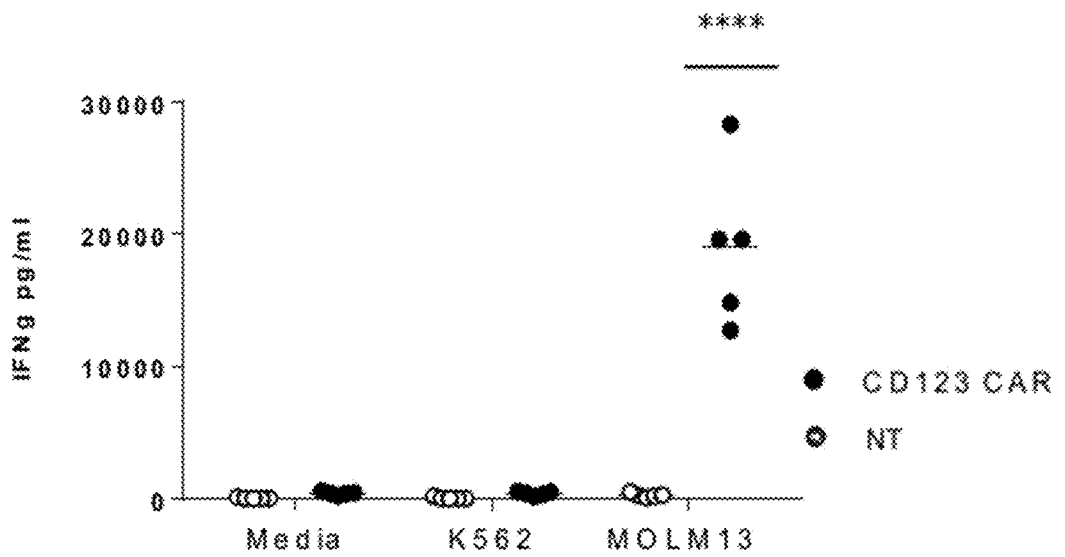
FIGS. 2A-2B demonstrate that CD8α.41BBz CAR T cells secrete increased interferon gamma (IFNγ) in the presence of antigen positive target cells. Cells were plated at a 1:1 ratio in the presence of media, CD123− (K562) or CD123+ (MOLM13) cells.
Figure 2B:
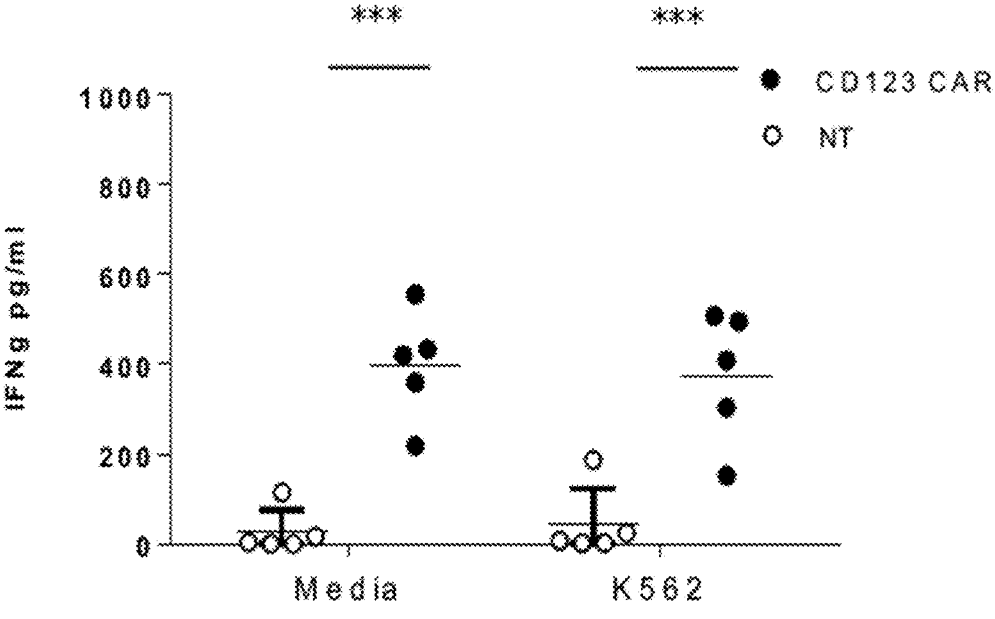

Cells were plated at a 1:1 ratio in the presence of media, CD123− (K562) or CD123+ (MOLM13) cells. Following 24 hours of culture, supernatant was harvested and analyzed for the presence of interferon gamma (IFNγ) using ELISA kits (R&D systems) according to the manufacturer's instruction. IFNγ secretion was significantly increased in the presence of MOLM13 (n=5; p<0.0001 (**), FIG. 2A). However, CD8α.41BBz CAR T cells showed increased baseline IFNγ secretion ("tonic signaling") in the presence of media and K562 (n=5; p<0.001 (*); FIG. 2B).

Example 3. Generation and Characterization of Additional CD123-CAR$^{CD20}$ Constructs In addition to the CD8α.41BBz CAR$^{CD20}$, four other CD123-CAR$^{CD20}$ constructs were designed using bicistronic lentiviral vectors encoding CD123-CARs and CD20 separated by a '2A' sequence (FIG. 3A). In the total five CD123-CAR$^{CD20}$ constructs, four constructs have the CD123-specific scFv (292), and for one construct the CD123-specific scFv derived from antibody 26716 (716) was used. Two different hinge/transmembrane (TM) domains (CD28 or CD8α), and costimulatory domains (CD28 alone, 41BB alone, or CD28.41BB) in combination with the CD3ζ (z) signaling domain were evaluated. CAR T cells were generated by lentiviral transduction, and their effector function was evaluated in vitro and in a xenograft AML model as described in Example 1.

Figure 3B:
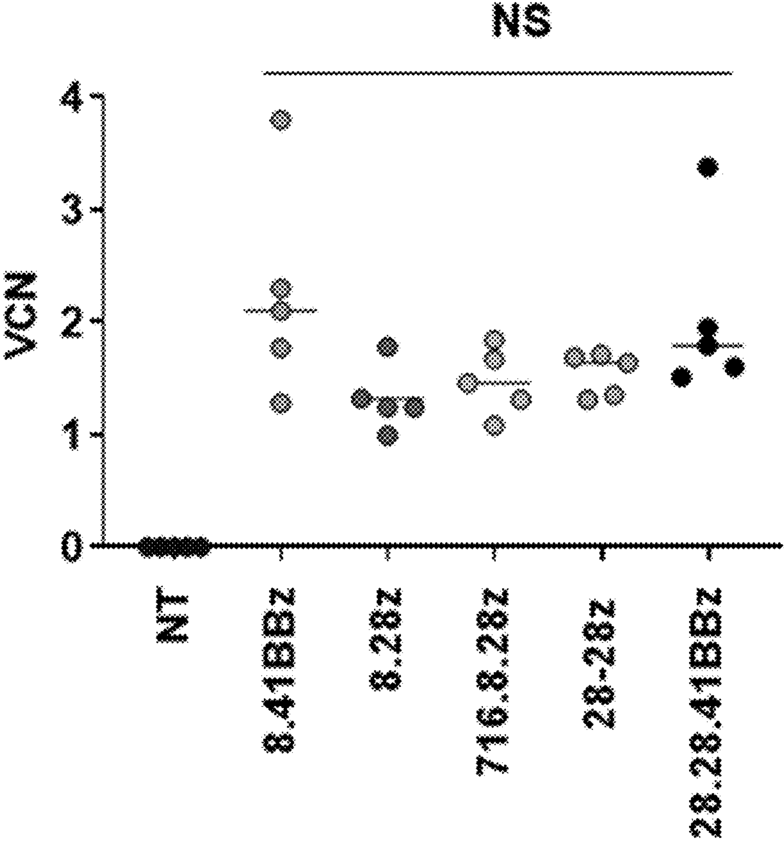
Figure 3C:
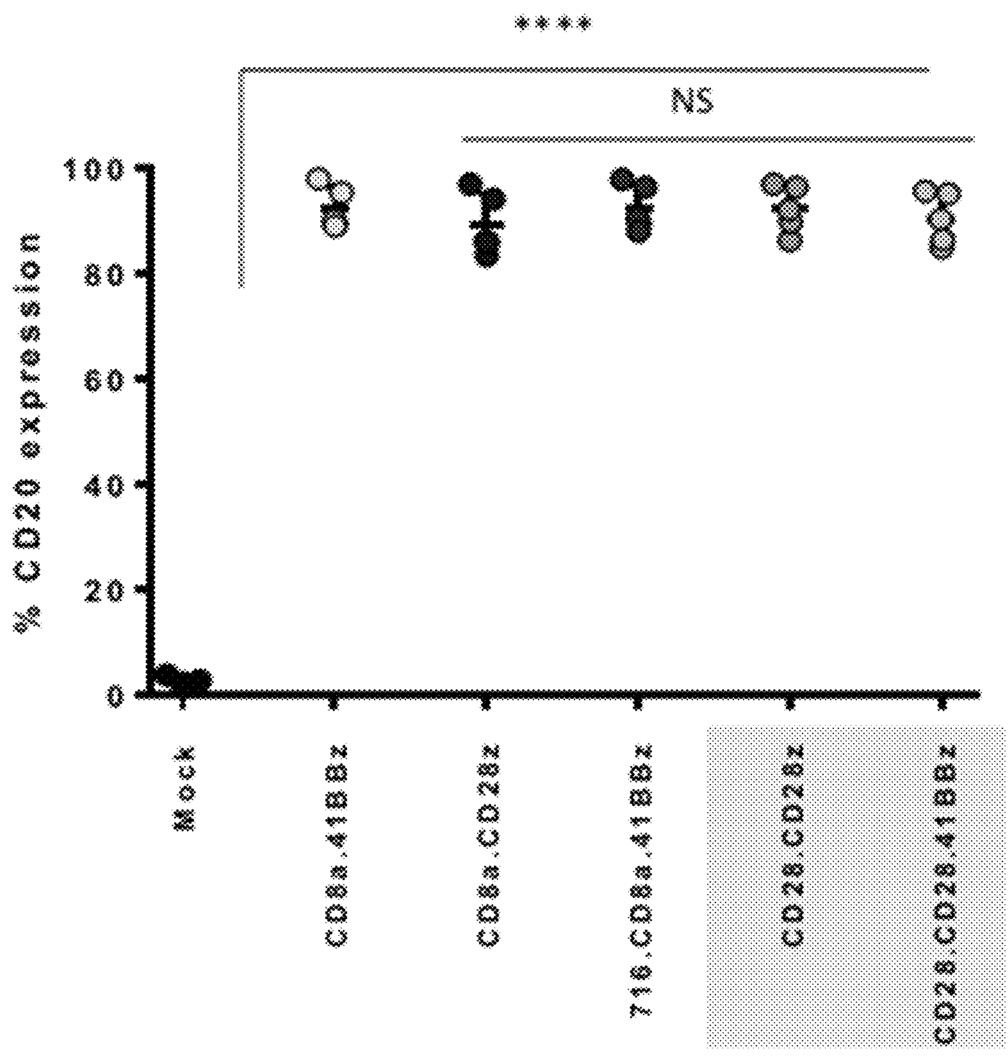
Figure 3D:
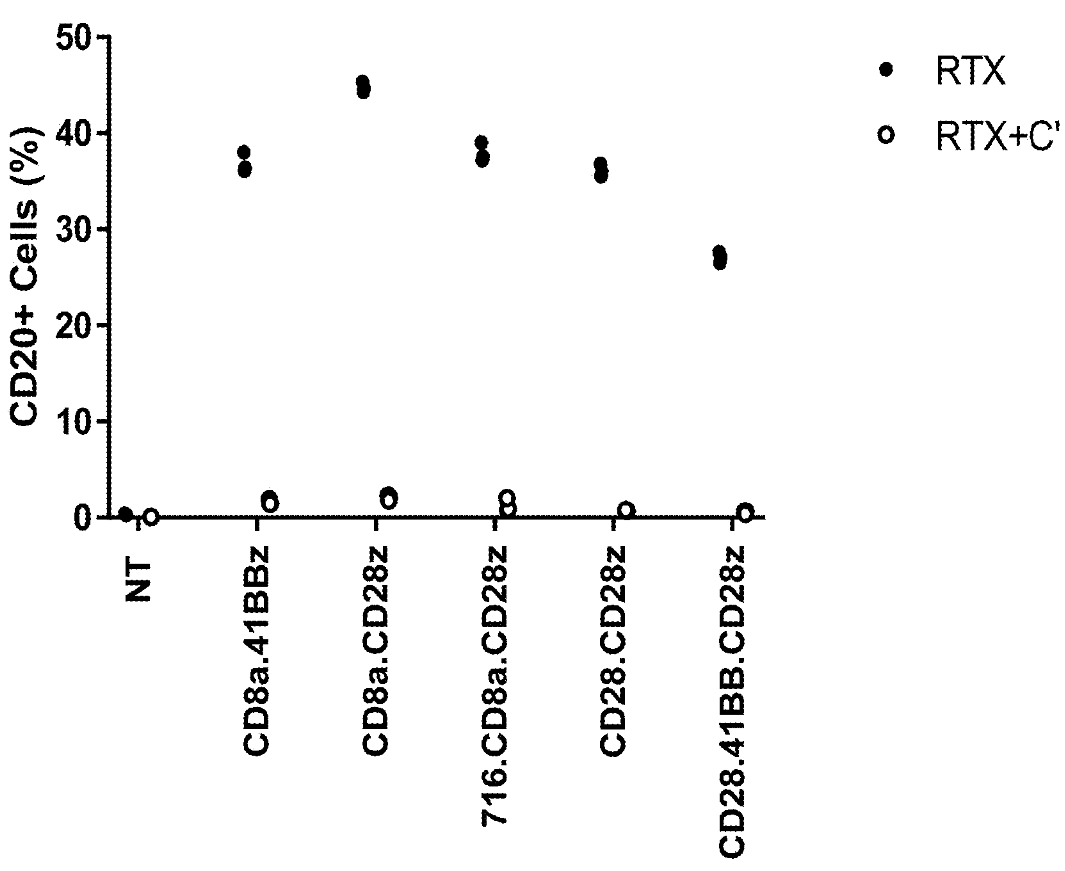
Figure 3E:
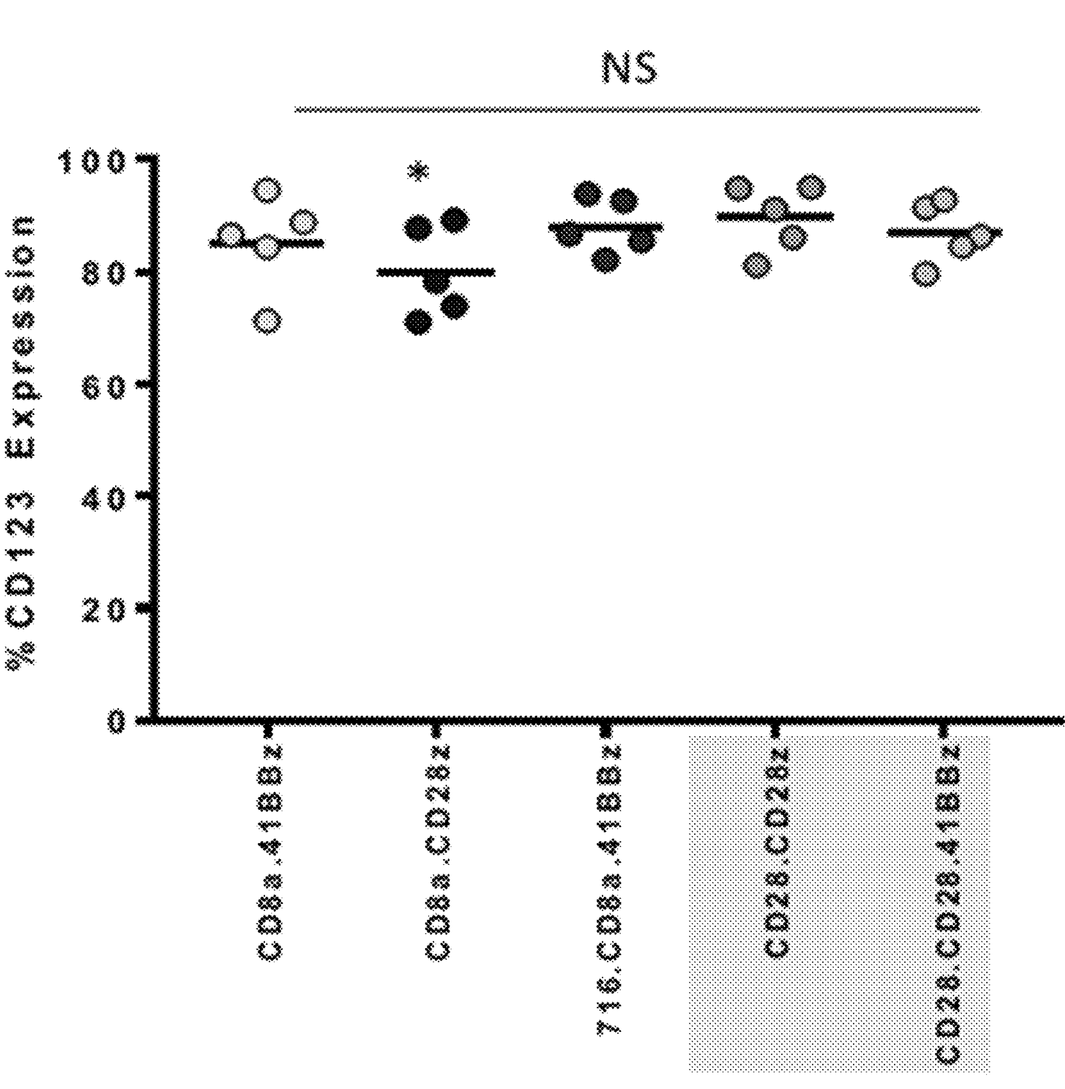
Figure 3F:
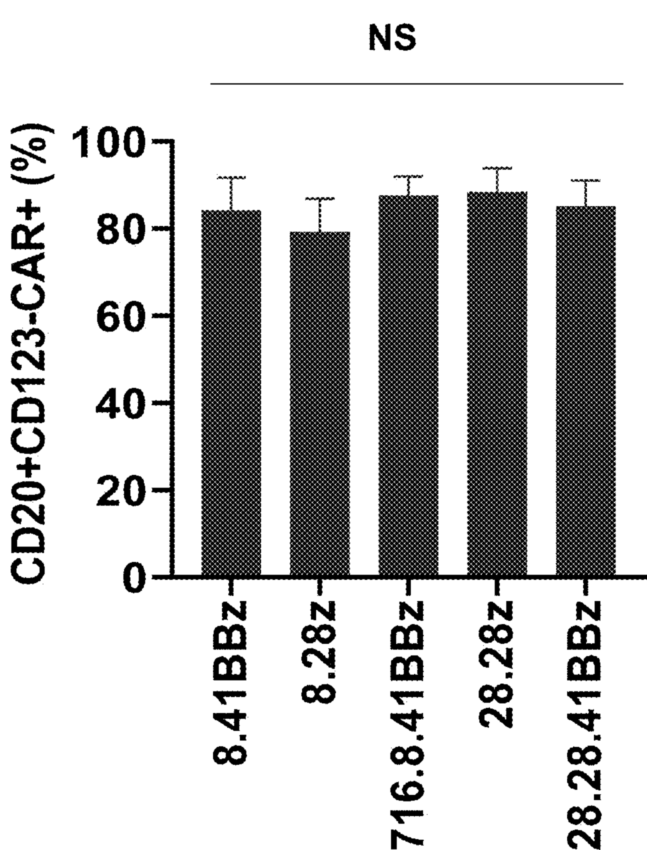
Figure 3G:
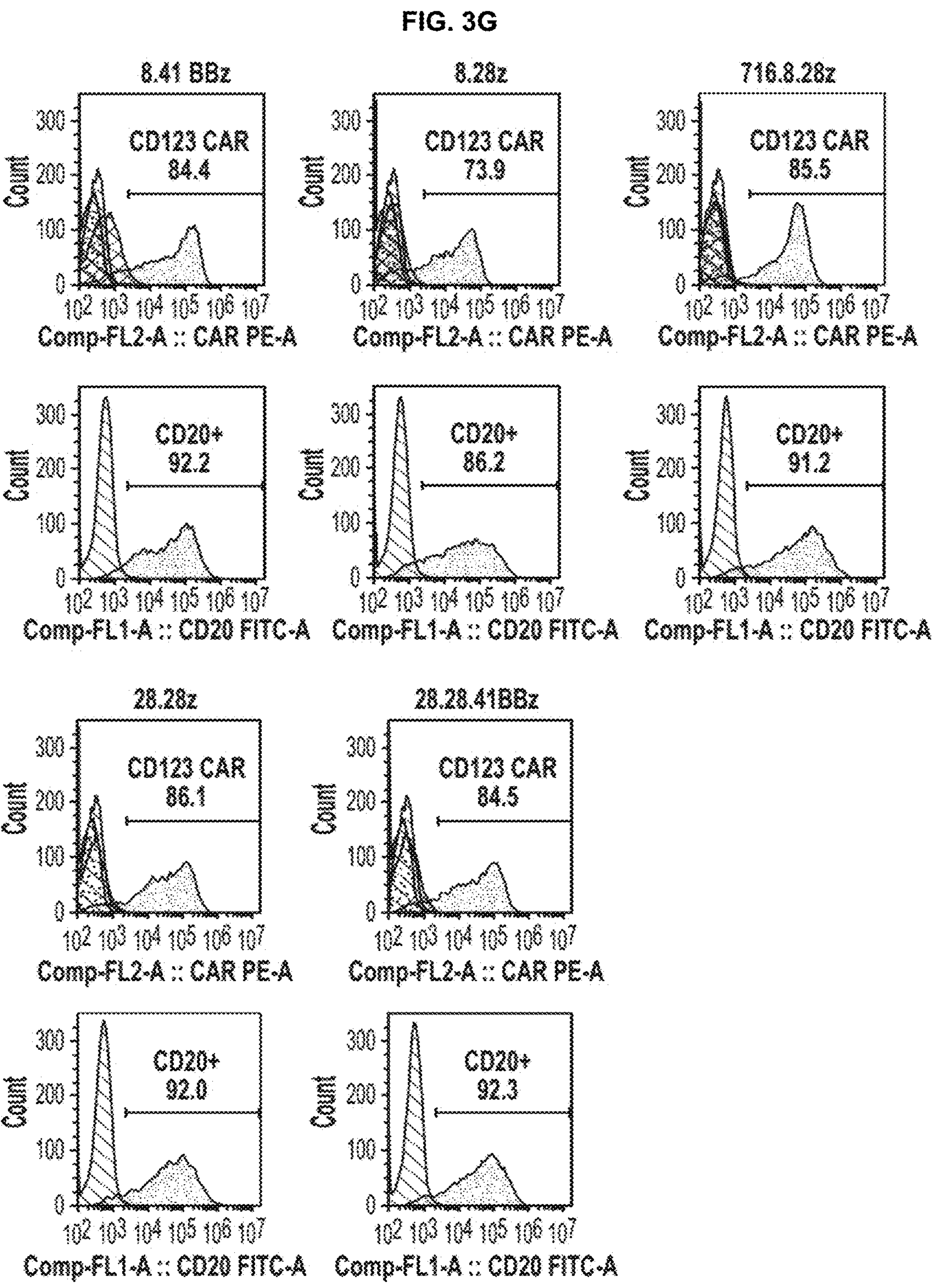
Figure 3H:
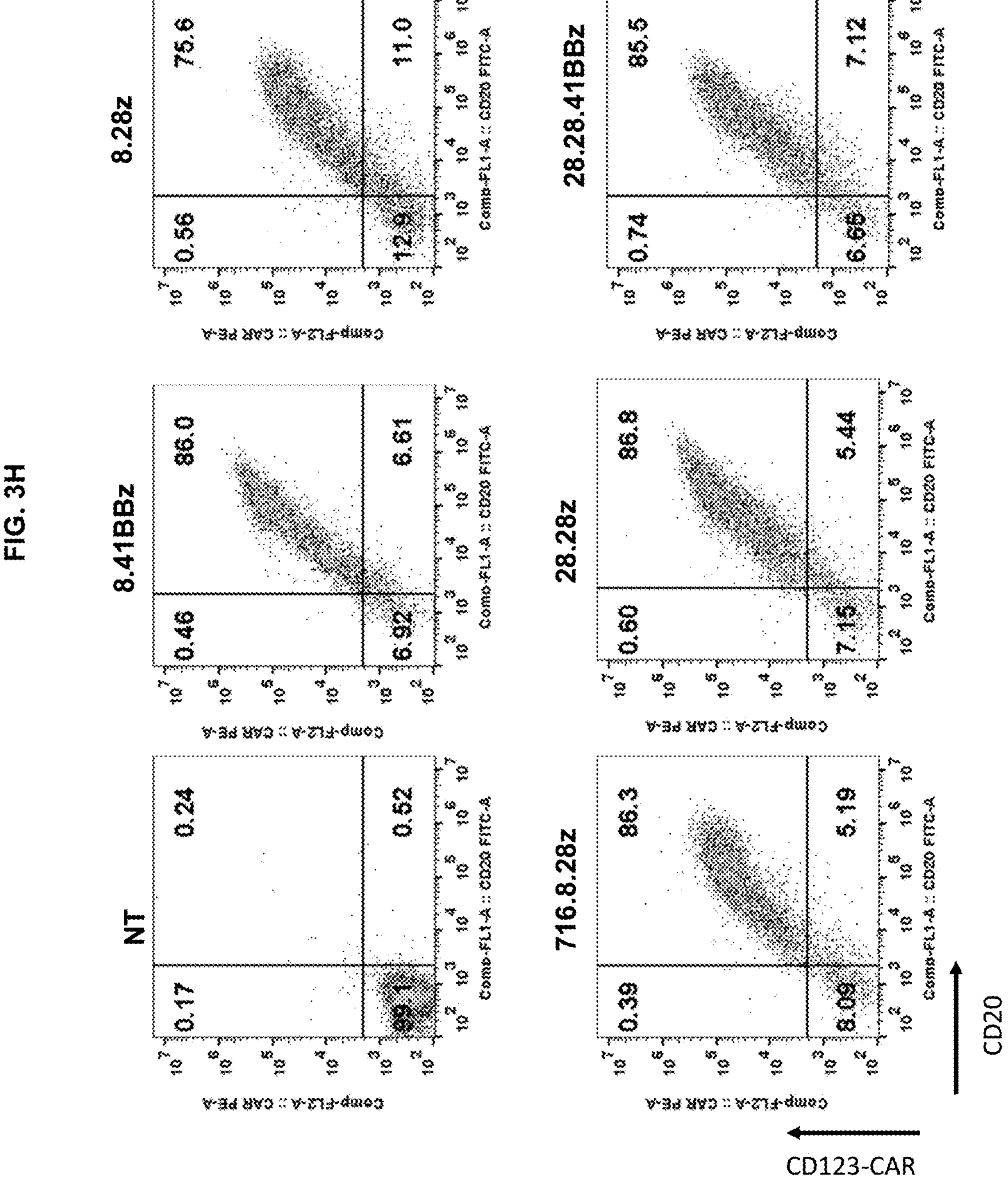
Figure 3I:
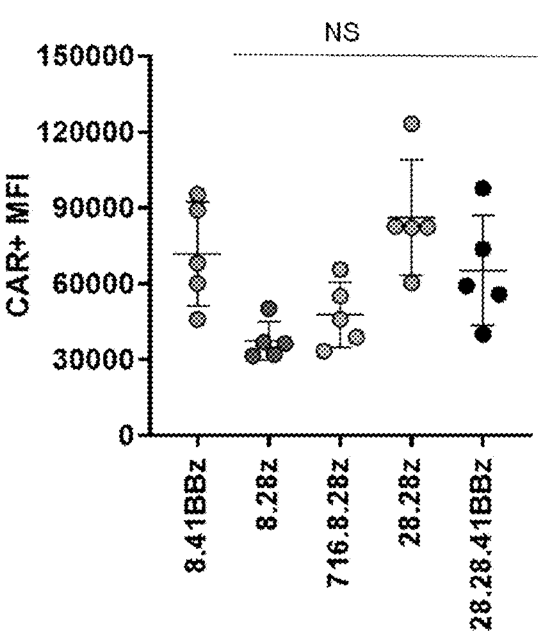
Figure 3J:
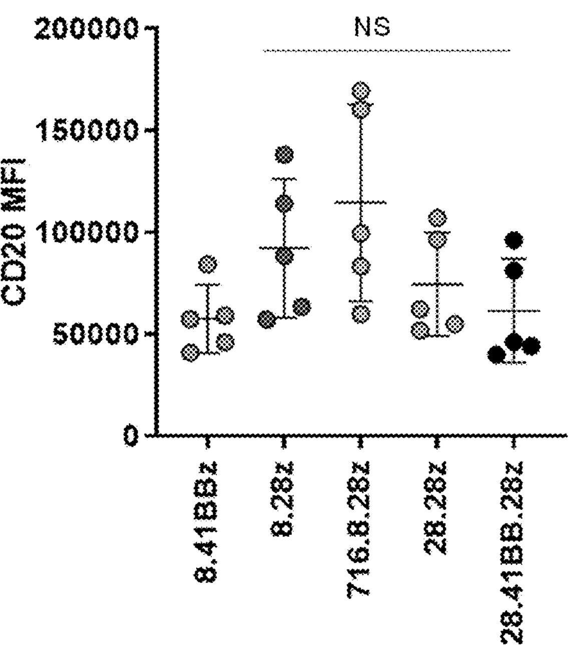
Figure 3K:
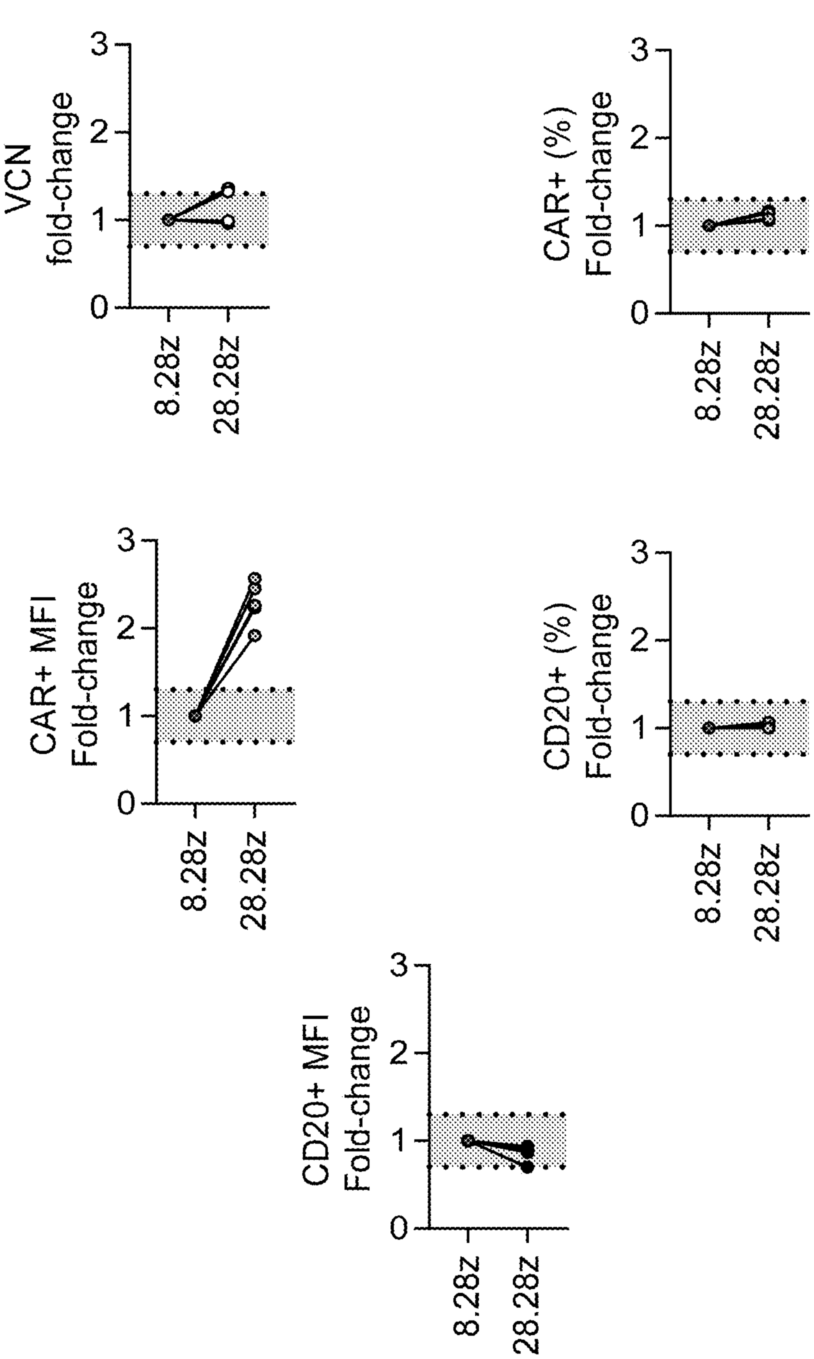

CD123-CAR T cells were successfully generated with all lentiviruses. Transduction efficiency was determined by vector copy number per cell (VCN) and FACS analysis. Mean VCN ranged from 1.31 to 2.25 (±0.40) as shown in FIG. 3B. Expression of the CD20 safety switch and CD123-CAR was evaluated by flow cytometry. There was no significant difference in CD20 expression (positive cell range: 83.2-97.7% (±1.4%); FIG. 3C), and CD123-CAR T cells were readily killed in the presence of rituximab and complement (80% killing within 1 hour incubation (FIG. 3D). CAR expression varied between 71 and 95% (±3.2%), and the % of CAR+ T cells was significantly lower post transduction with the lentivirus encoding the CD8αTM. CD28z CAR (p<0.05); FIG. 3E). CD123-CAR and CD20 expression followed a linear relationship for all designed CARs (FIGS. 3F-3H), and there was no difference in the level of CD123-CAR and CD20 expression as judged by mean fluorescence intensity (MFI; FIGS. 3I, 3J). No significant differences (n=5, p=NS) between CD20-2A-CAR constructs was observed regarding VCN and transgene expression when all five CAR constructs were compared. Comparison of CD8α and CD28 hinge/transmembrane domain (H/TM) CARs with the same signaling domain revealed a mean 2.3-fold (range: 1.9 to 2.6) higher expression of CD28 H/TM CARs on the cell surface of T cells as judged by determining the mean fluorescence intensity (MFI) of CAR-positive T cells (FIG. 3K). In contrast, mean fold changes for all other transduction parameters (% CAR positive, VCN, % CD20 positive, CD20 WI) between T cells transduced with the CD20-2A-CD8α or CD28 H/TM CAR LVs was between 0.8 and 1.2 (FIG. 3K).

Figure 3L:
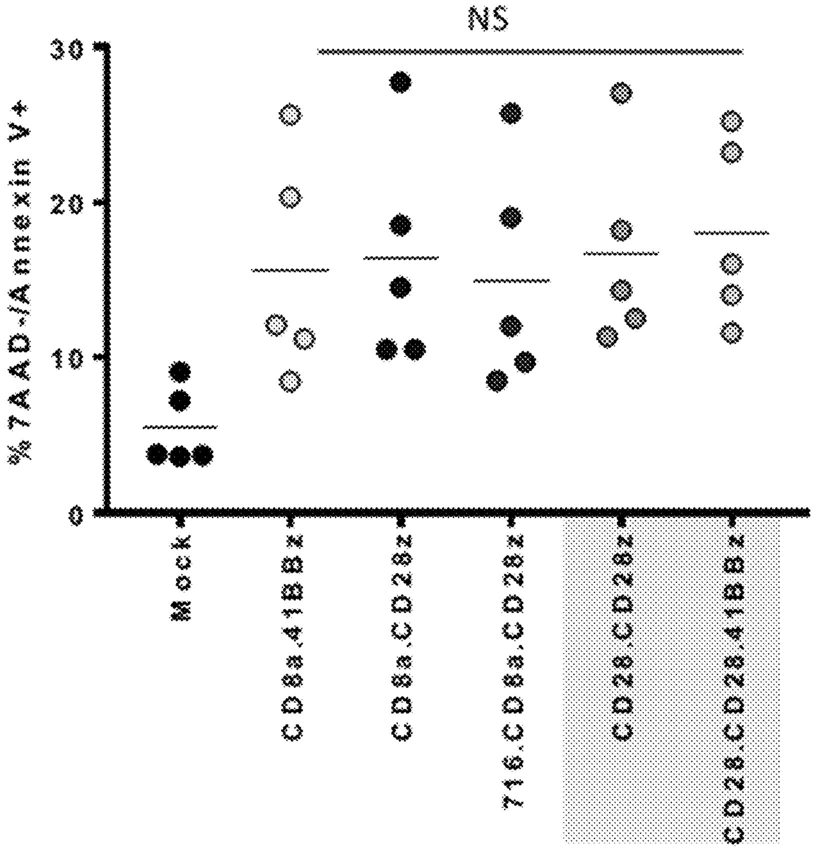
Figure 3M:
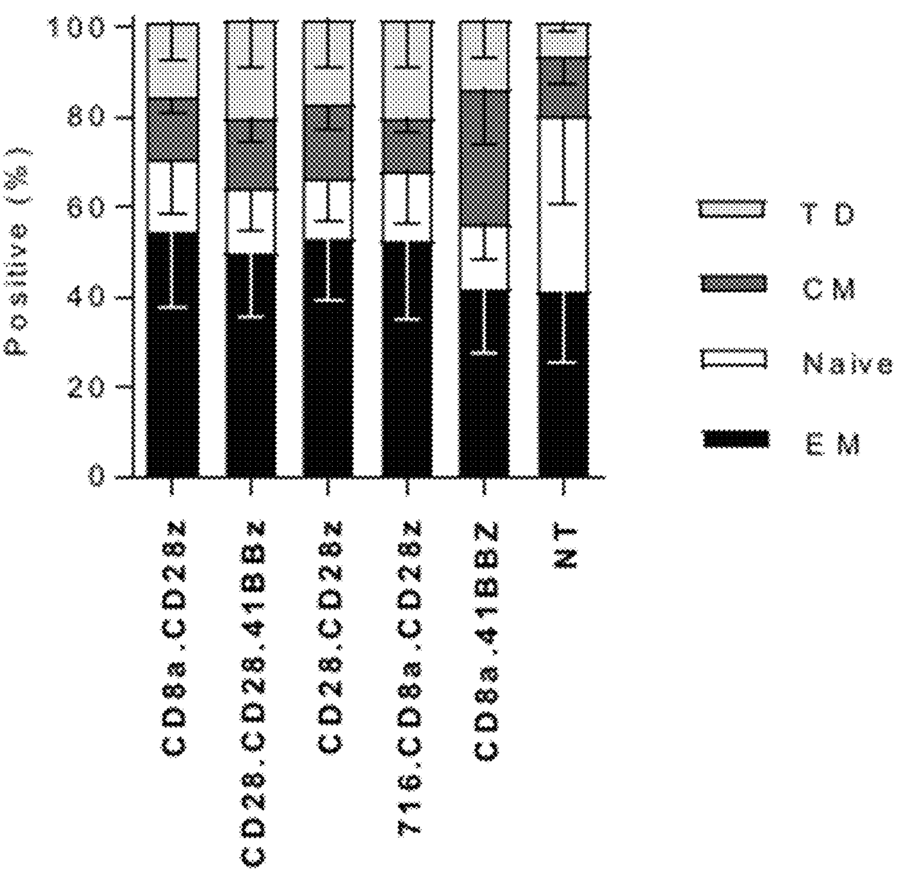

T cell viability was assessed using 7AAD/Annexin V staining. No difference was observed between the T cells transduced with different CD123 CAR constructs (n=5, p=NS; FIG. 3L). CD123 CAR T cells had a viability of greater than 80% (FIG. 4B, p=NS). The frequency of naïve (Naive: CCR7+CD45RA+), effector memory (EM: CCR7−CD45RA−), central memory (CM:CCR7+CD45RA−), and terminally differentiated (TD: CCR7−CD45RA+) T cells was also evaluated in the T cells transduced with different CD123-CAR constructs at day 8. All constructs resulted in comparable immunophenotypes (including CD3, CD4, CD8, CCR7, CD45RA) in the transduced T cells (n=5; FIG. 3M).

Figure 4A:
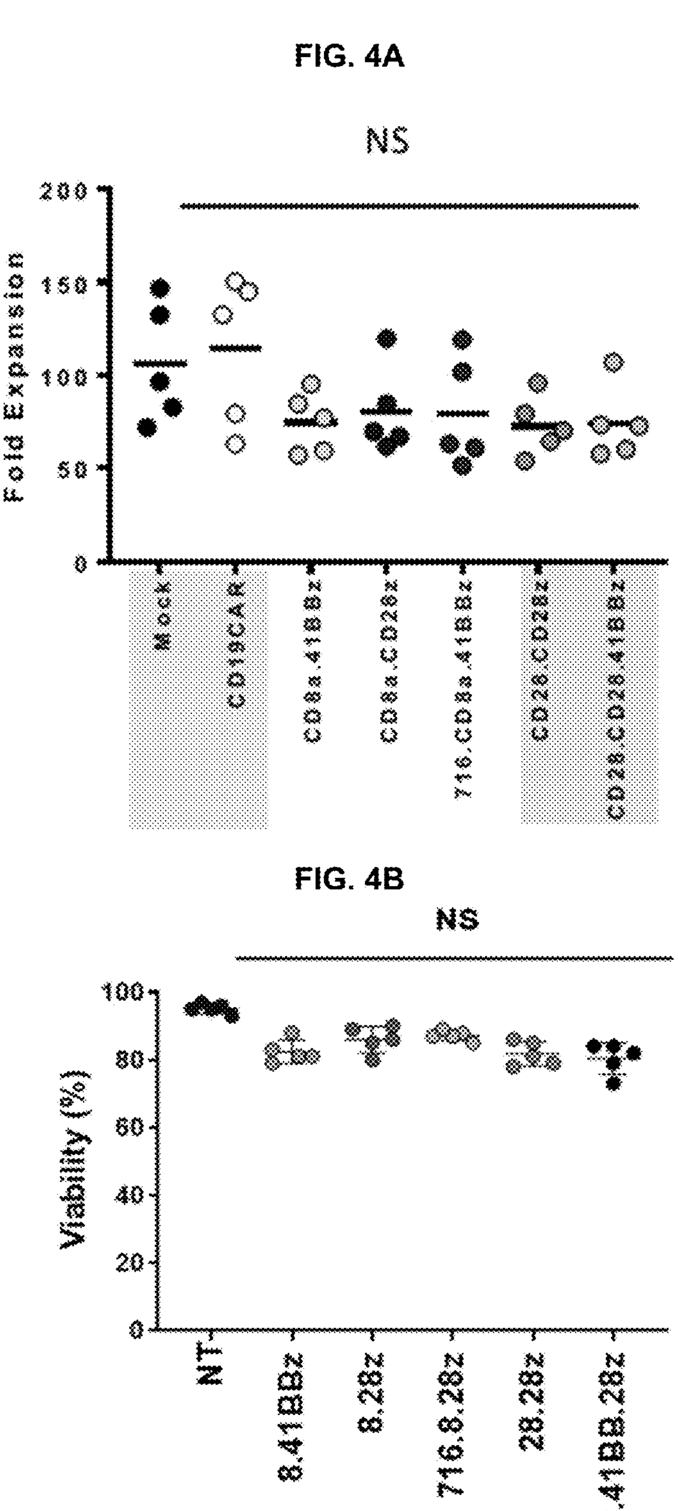
Figure 4C:
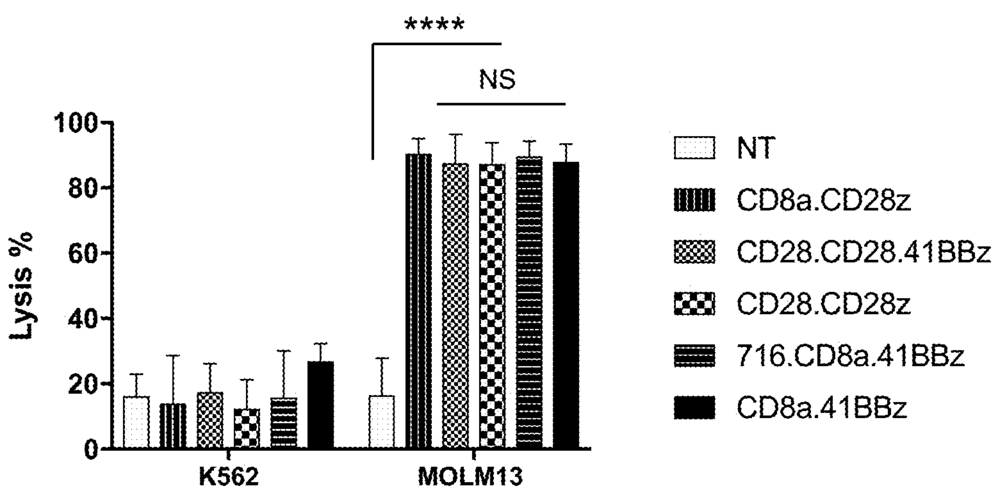

Further, all CD123 constructs were able to expand in a similar way as mock (NT) and CD19-CAR T cells, after 8 days in culture (FIG. 4A, n=5). In coculture assays, CD123-CAR and NT T cells were co-cultured with CD123+ (MOLM13) and CD123− (K562) target cells at 3:1 effector to target ratio. Tumor lysis was determined after 24 hours by flow cytometry. The assay was performed in triplicates. CD123-CAR T cells recognized CD123+ AML cells (MOLM13) as judged by IL-2 and IFNγ secretion in contrast to NT T cells (n=5, p<0.0001) with no significant differences between CARs (FIG. 4C).

Figure 4D:
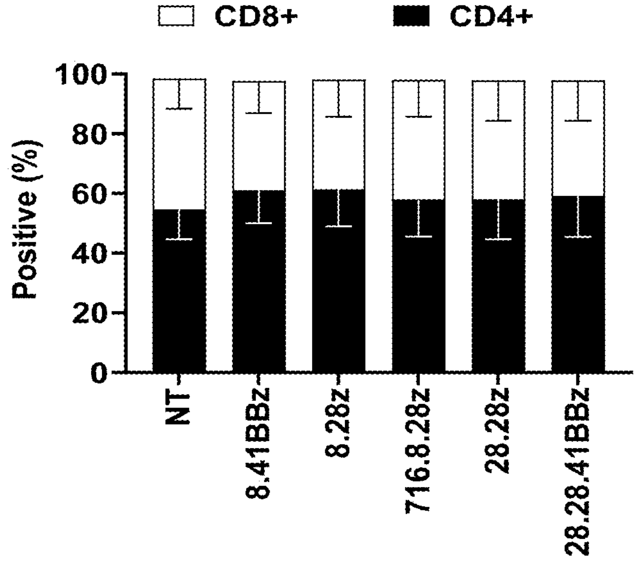
Figure 4E:
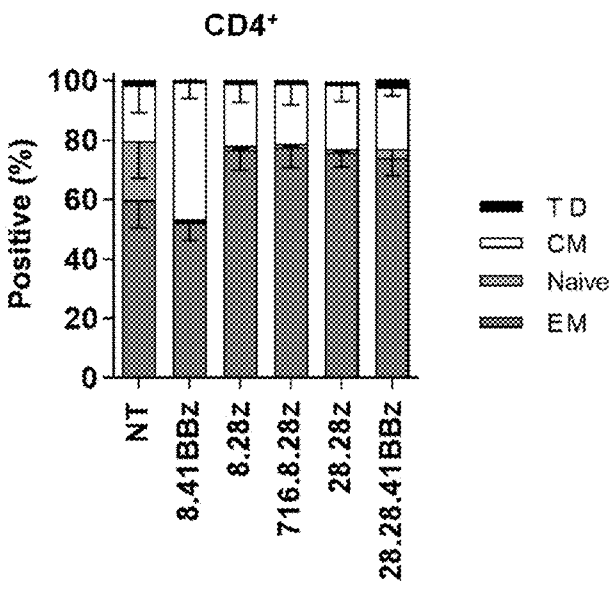
Figure 4E:
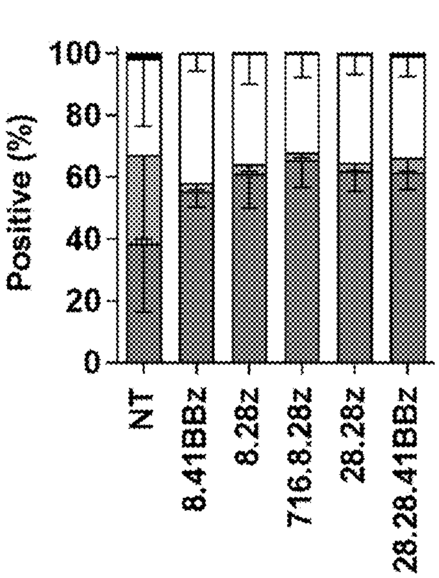
Figure 4F:
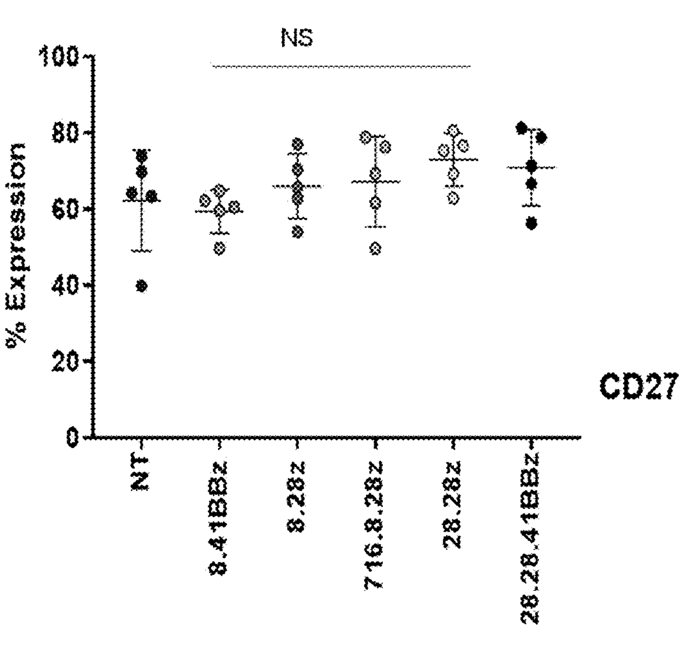
Figure 4G:
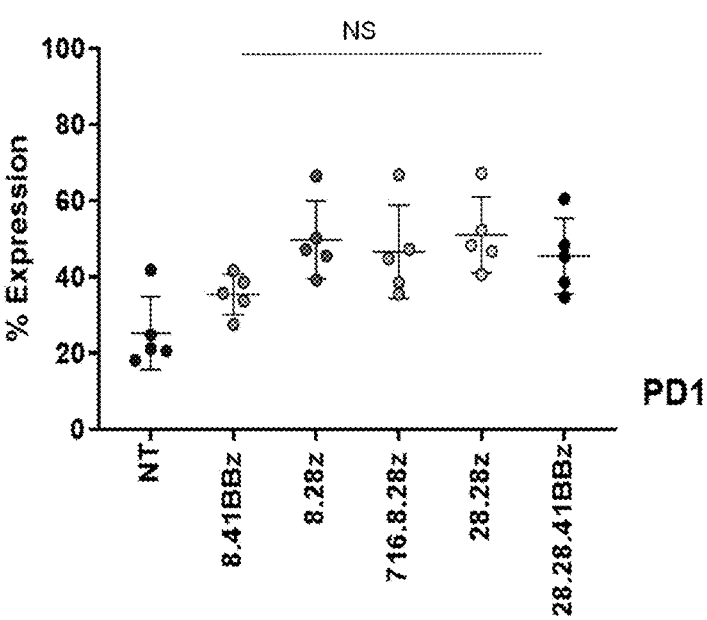
Figures 4H, 4I:
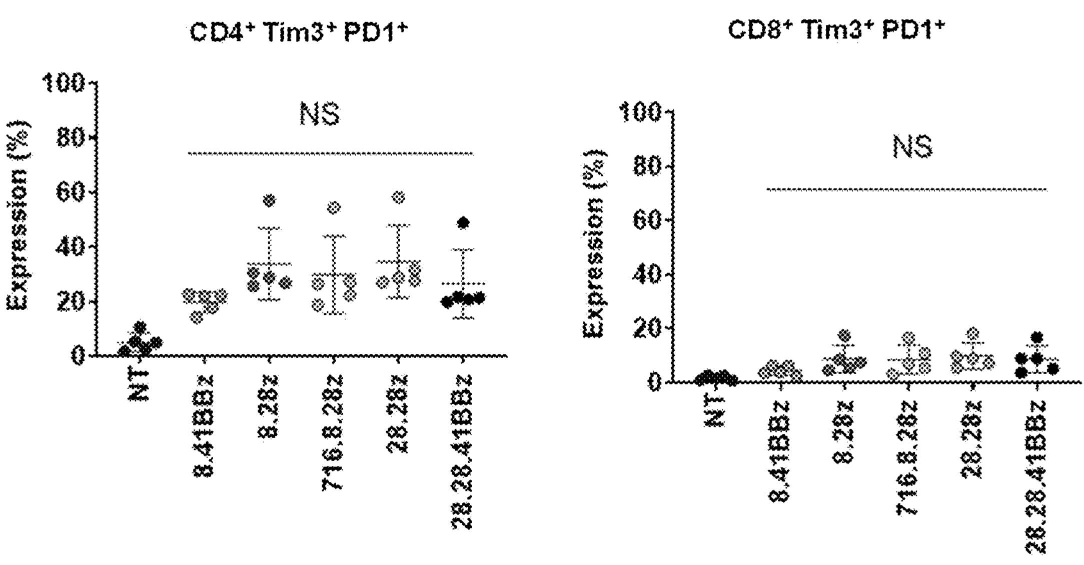

Determination of immunophenotype subsets (naïve: CCR7+CD45RO−; central memory (CM): CCR7+ CD45RO+; terminally differentiated (TD): CCR7-CD45RO−; effector memory (EM): CCR7-CD45RO+) on day 8 revealed a CD4:CD8 ratio near 1:1 for all constructs (FIG. 4D, n=5 p=NS). The majority of T-cells demonstrated an EM or CM phenotype (FIG. 4E). Only non-transduced (NT) T-cells had a significant percentage of naïve T-cells when compared to CD123-CAR$^{CD20}$ T-cells (NT vs CD123-CAR$^{CD20}$ T-cells: CD4+ T-cells: n=5, p<0.01; CD8+ T-cells: p<0.0001). FACS analysis for the activation markers CD27, Tim3 and PD1 did not reveal any significant differences of single positive cells (FIGS. 4F-4H) or double positive (Tim3+/PD1+) populations between CD123-CAR$^{CD20}$ T-cells for either CD4+ or CD8+ subsets (FIG. 4I; n=5, p=NS).

Example 4. Tonic Signaling is Abrogated by Expression of CD28z

Figure 5A:
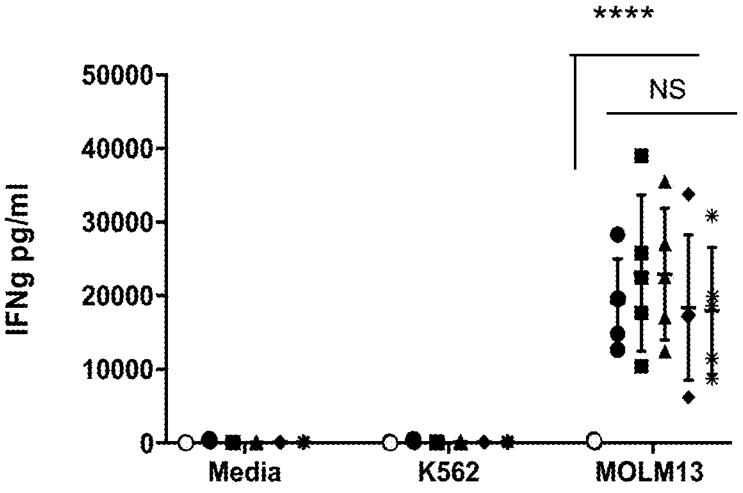
FIGS. 5A-5B demonstrate that constructs expressing CD28z costimulatory domain have lower ligand independent IFNγ secretion. CD123-CAR and mock treated T cells were co-cultured with CD123+ (MOLM13), CD123−

CD123-CAR and mock treated T cells were co-cultured with CD123+ (MOLM13), CD123− (K562) target cells or media. IFNγ secretion was evaluated after 24 hours of culture. All CD123 CAR constructs had significantly higher IFNγ secretion in the presence of CD123+ tumor cells when compared to mock treated T cells (n=5; IFNγ secreted by CD123-CAR$^{CD20}$ T-cells: range=6,176-39,000 pg/ml; p<0.0001 (**); FIG. 5A). There was no significant difference in IFNγ secretion among the constructs. However, CD8α.41BBz CAR T cells produced significant amounts of IFNγ (200-600 pg/ml) at baseline in comparison to other CAR constructs (p<0.001). On the contrary, CD123-CAR constructs expressing a CD28 costimulatory domain had significantly lower baseline IFNγ secretion when cultured in media (n=5; CD8α.41BBz CAR vs remaining constructs p<0.0001 ()) and in the presence of CD123− tumor cells (n=5; CD8α.41BBz CAR vs remaining constructs p<0.001 (*), FIG. 5B). The results suggest that constructs expressing the CD28z costimulatory domain have lower ligand independent IFNγ secretion.

Figure 5B:
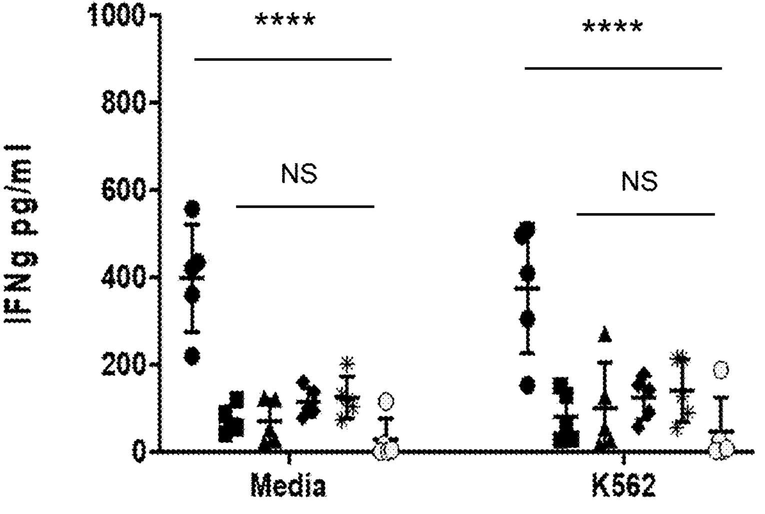
Figure 5C:
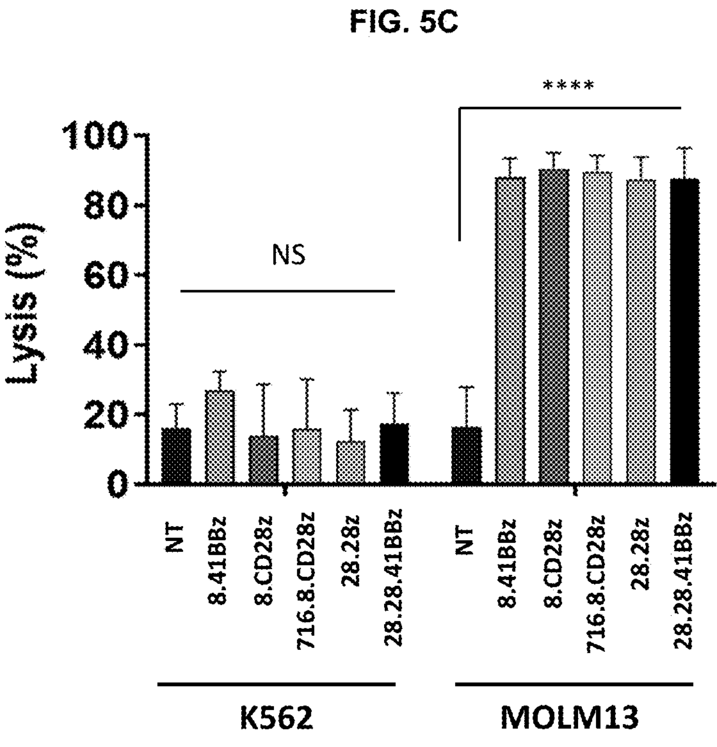
(FIG. 5C) Target cell populations were labeled with carboxyfluorescein succinimidyl ester (CFSE), incubated with Effector T-cells at the indicated ratios overnight and analyzed by flow cytometry using absolute counting beads to determine cytotoxicity. n=5; p=NS for comparison on K562 targets and p<0.0001 for CD123-CAR$^{CD20}$ compared to NT on Molm13.
Figure 5D:
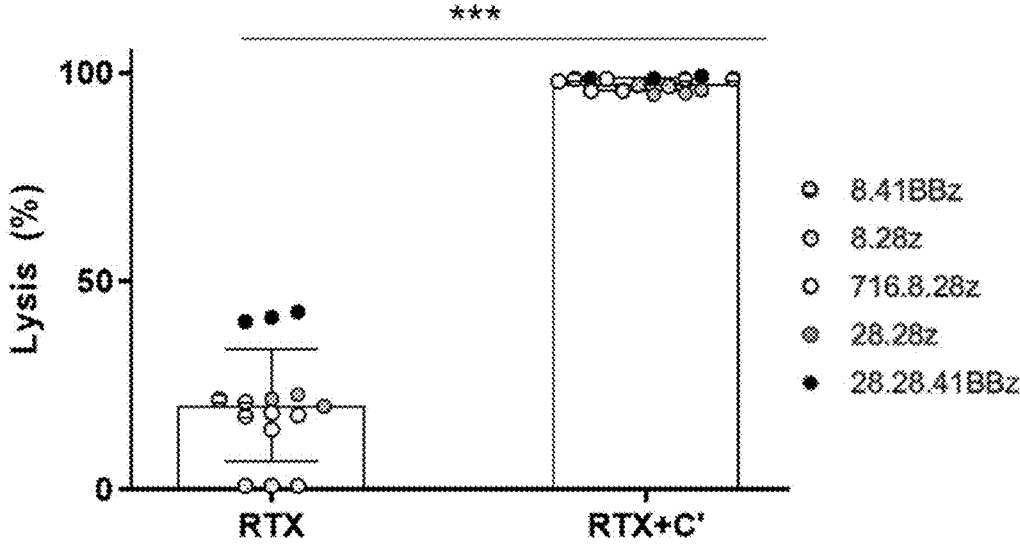
(FIG. 5D) T-cells treated with rituximab alone or rituximab plus baby rabbit complement were analyzed by flow cytometry to determine the percent of CD20+ cells lysed (n=15; p<0.001).

CD123-CAR$^{CD20}$ T-cells had significant in vitro antitumor activity against CD123-positive target-cells (FIG. 5C; n=5; p<0.0001), but not against the CD123-negative cells (K562). In contrast, NT T-cells did not secrete IFNγ or kill CD123-positive target-cells (FIGS. 5A-5C). Thus, all CD123-CAR$^{CD20}$ T-cell products had the desired specificity and only the CD8.41BBz-CAR induced significant baseline T-cell activation as judged by IFNγ production. In addition, all CD123-CAR$^{CD20}$ T-cell populations were efficiently eliminated (FIG. 5D n=15, p=0.0007) in the presence of rituximab and complement with no differences between constructs.

Figure 6:
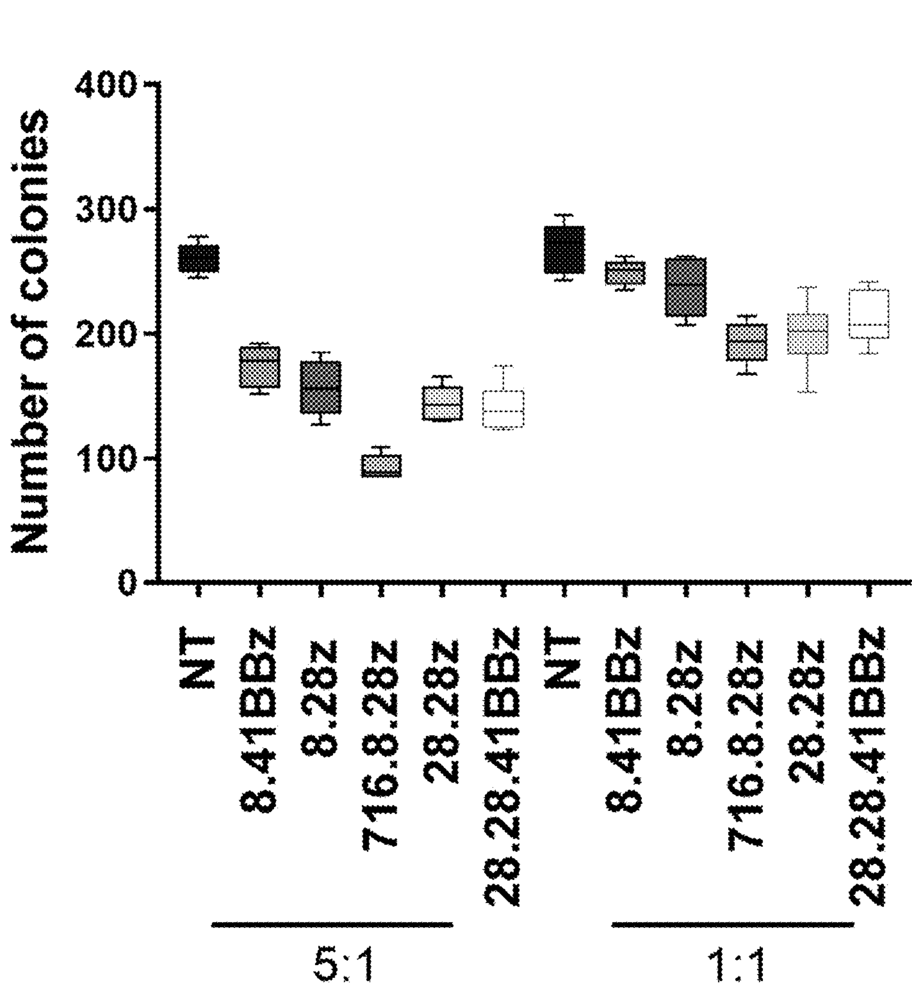
FIG. 6 shows recognition of CD123+ hematopoietic precursor cells by CD123-CAR$^{CD20}$ T-cells. Effector cells were incubated with CD34+ HPCs for 4 hours at E:T ratios of 5:1 and 1:1, plated on semisolid media and evaluated 12-14 days later (n=6 biological replicates; *: p<0.05; black asterisk: comparison to NT T-cells; red asterisk: comparison between CAR constructs).

Example 5. CD34+ HPCs are Recognized to a Greater Extend by 716 than 292 scFv-Based CARs As there was no observed difference in regards to AML, target recognition, the potential “on target/off cancer” toxicity of CD123-CAR$^{CD20}$ T-cells was compared against CD34+ HPCs in a standard colony forming unit (CFU) assay at two effector to target ratios (E:T; 1:1; 5:1). At an E:T ratio of 1:1, three (716.CD8.CD28z, CD28.CD28z and CD28.CD28.41BBz) out of the five evaluated CD123-CAR$^{CD20}$ T-cell populations were cytotoxic to CD34+ target cells (FIG. 6; n=6 biological replicates). At an E:T ratio of 5:1, all CD123-CAR$^{CD20}$ T-cells caused a significant (p<0.05) reduction in CFUs. At this higher E:T ratio, 716. CD8. CD28z CAR T cells induced a greater reduction in CFUs (FIG. 6) when compared to other CD123-CAR$^{CD20}$ T cells.

Example 6. CD123-CAR T Cells have Antitumor Activity In Vivo

CD123+ MOLM13 (AML) cells expressing firefly luciferase (ffluc) were injected into NSG mice intravenously (iv) via tail vein. On Day 7 mice received a single iv dose of $3\times10^6$ or $1\times10^7$ CD123-CAR T cells. Mice that only received tumor cells served as controls (No T cells). AML progression was tracked by bioluminescence imaging (n=5 per group). Animals receiving only tumor cells had progression of disease and required euthanasia around Day 30.

Figure 7:
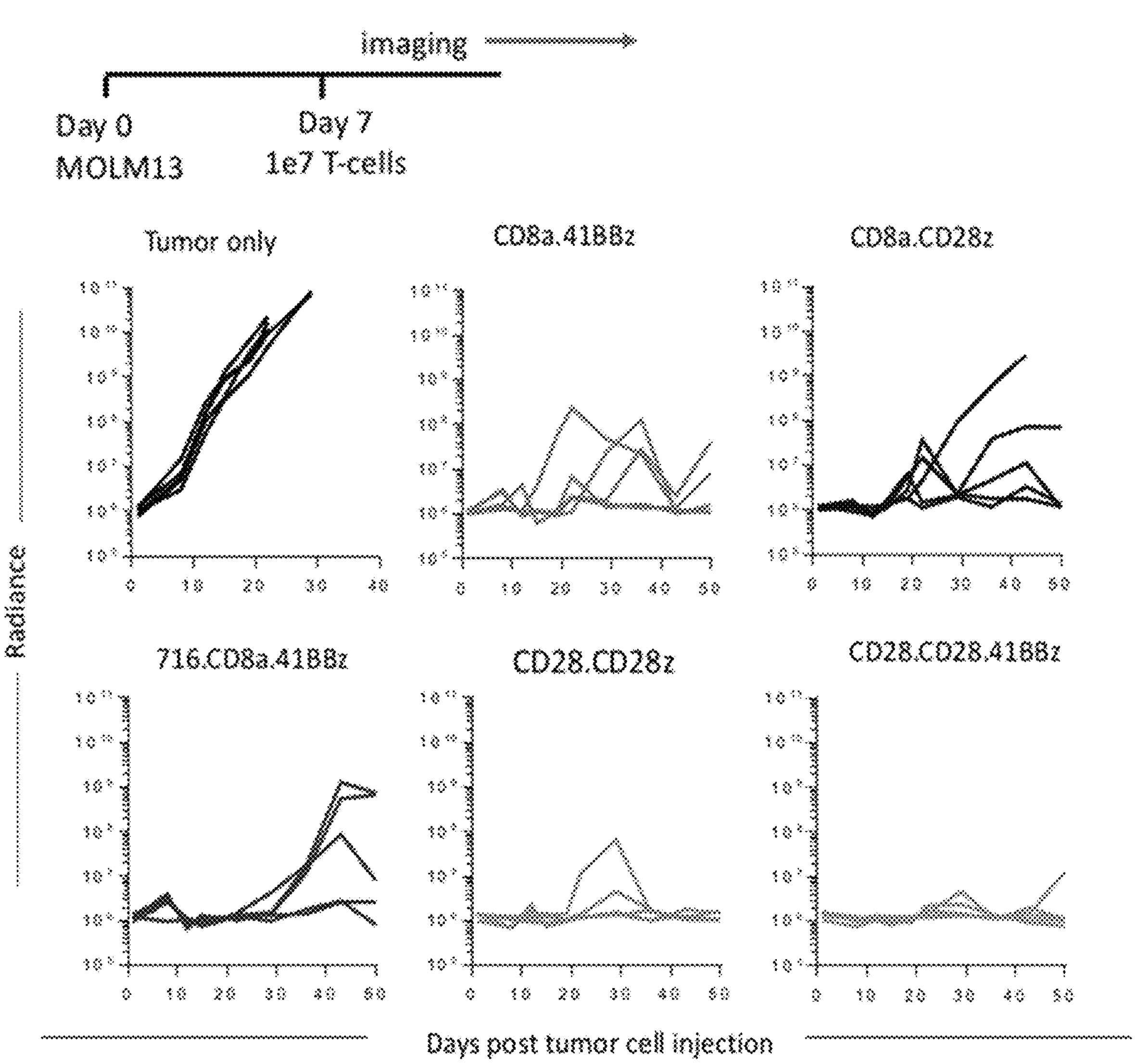
FIG. 7 shows that CD123-CAR T cells have antitumor activity in vivo. CD123+ MOLM13 (AML) cells expressing firefly luciferase (ffluc) were injected by intravenously (iv) via tail vein. On Day 7 mice received a single iv dose ($1\times10^7$ cells) of CD123-CAR T cells. Mice that only received tumor cells served as controls (No T cells). AML progression was tracked by bioluminescence imaging (n=5 per group). Animals receiving only tumor cells had progression of disease and required euthanasia around Day 30.
Figure 8A:
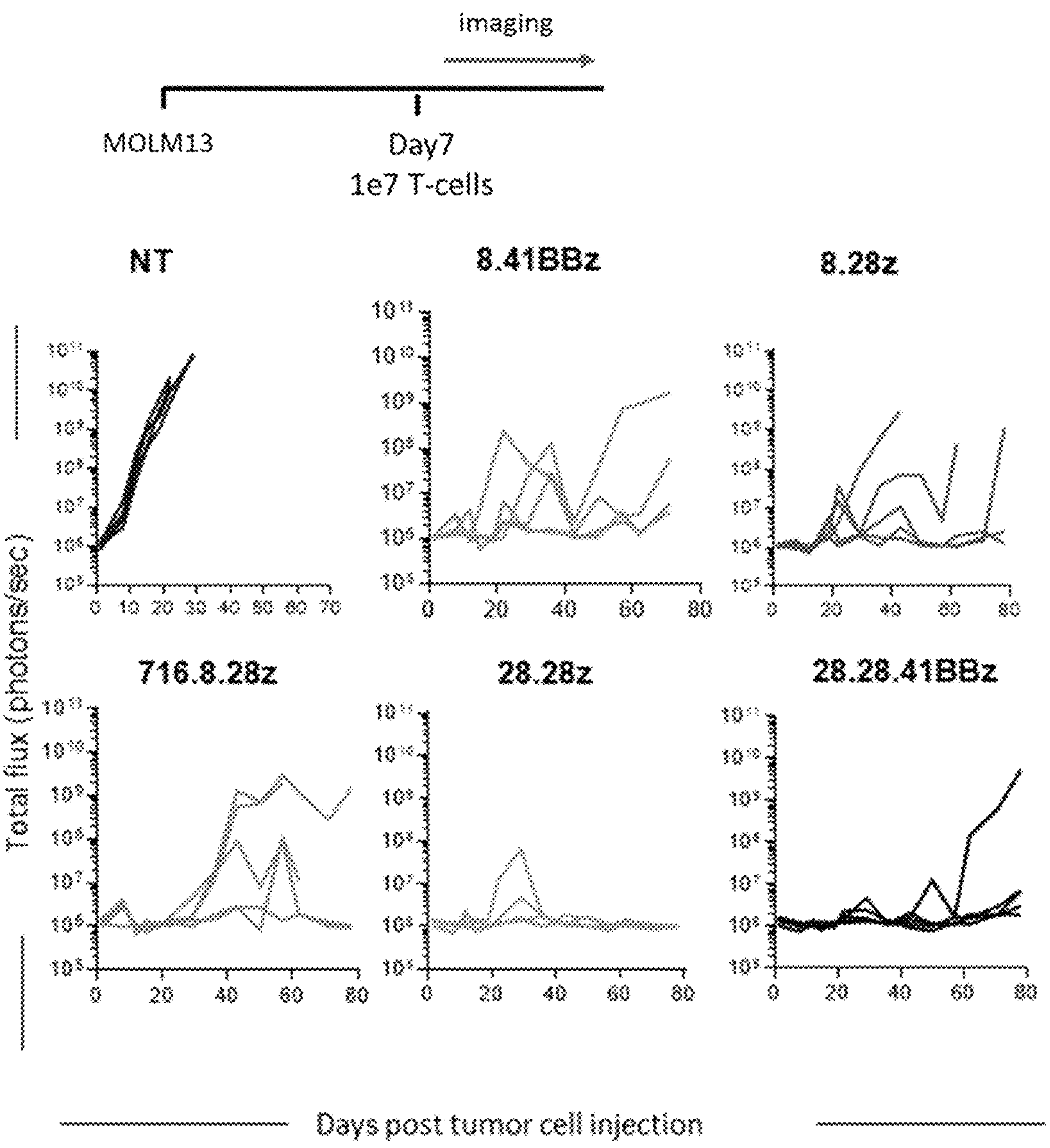
FIGS. 8A-8B shows that CD123 CAR T cells have antitumor activity in vivo. The assay was carried out as described in FIG. 7.
Figure 8B:
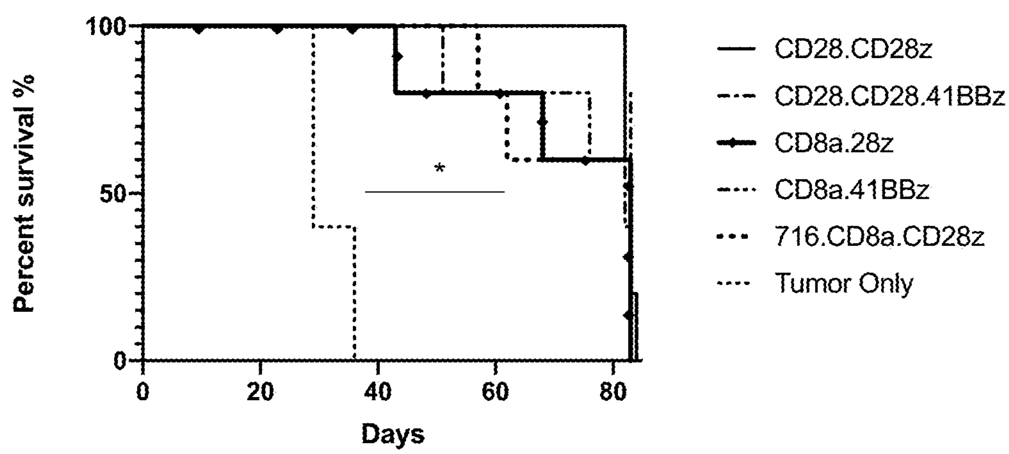
Figure 9A:
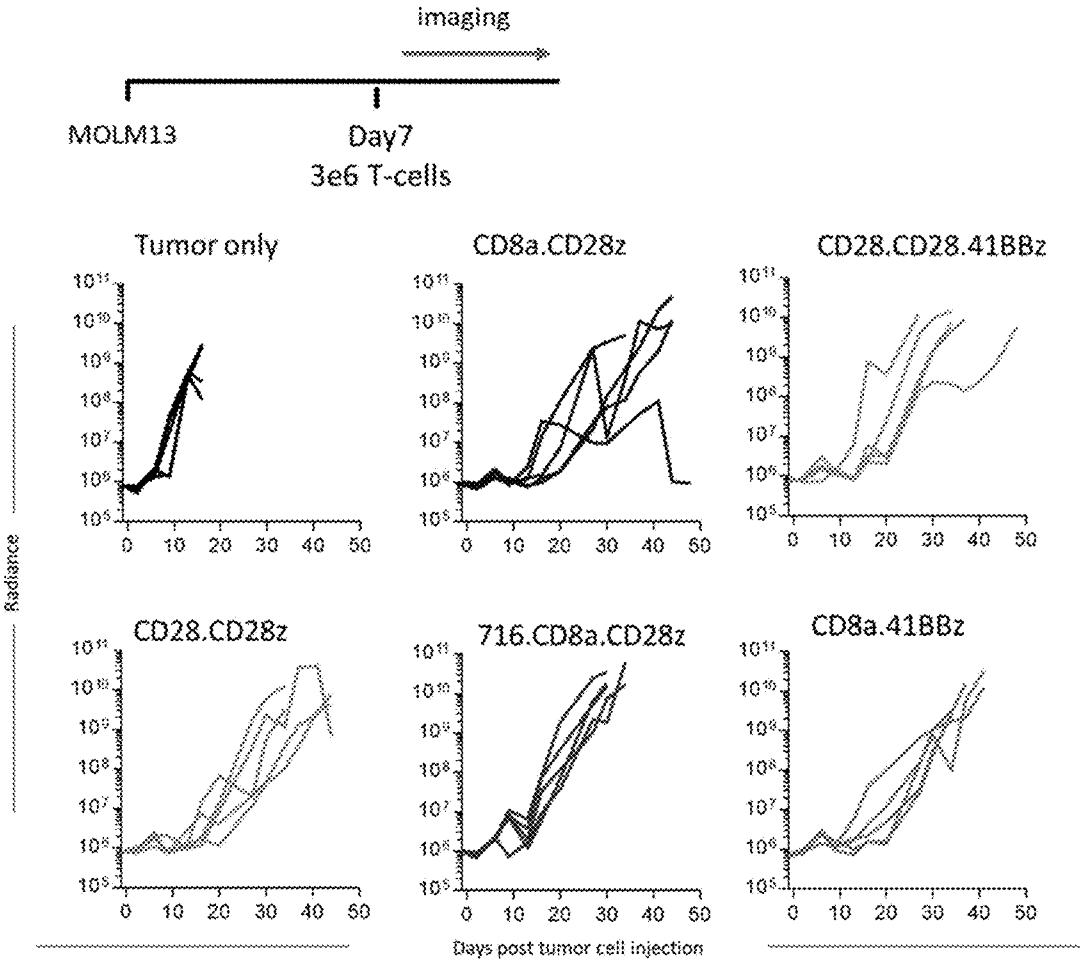
FIGS. 9A-9B shows that CD123-CAR T cells have antitumor activity in vivo. The assay was carried out as described in FIG. 7 except that animals received a dose of $3\times10^6$ cells.
Figure 9B:
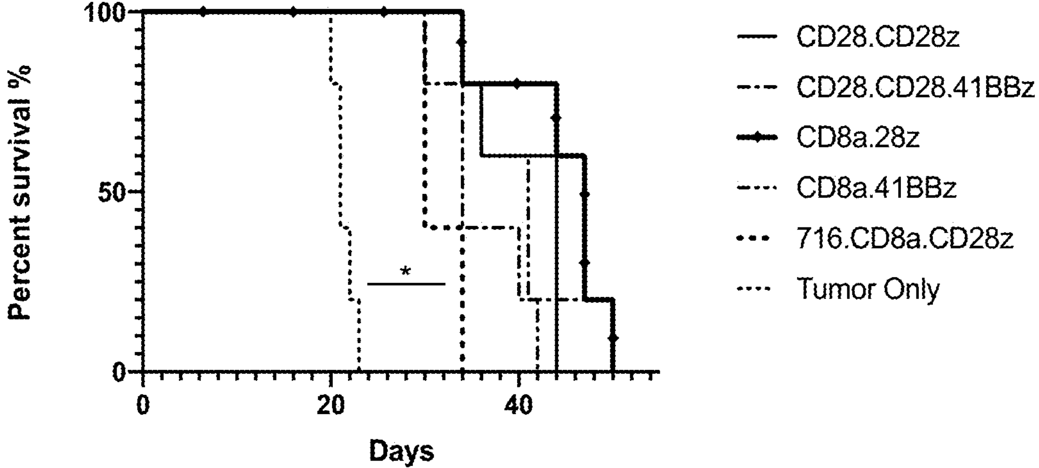

At both cell doses CD123-CAR$^{CD20}$ T cells had significant antitumor activity in comparison to untreated controls resulting in a survival advantage. The results for the higher cell dose experiments are shown in FIGS. 7 and 8A-8B. At the lower cell dose, T cells expressing CARs with a 716 scFv had inferior (p<0.01) antitumor activity (FIGS. 9A-9B). Addition of the 41BB signaling domain to 292.CD28TM.CD28.z CARs did not improve anti-AML activity. There was no observed difference in the weight of the animals among different treatment groups receiving either lower cell dose or high cell dose of CD123-CAR$^{CD20}$ T cells. Based on these findings, T cells expressing CD28TM CAR were selected for future clinical testing.

Figure 10A:
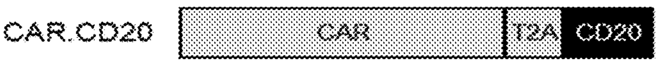
FIGS. 10A-10C demonstrate that the inclusion of CD20 as a safety switch enables efficient depletion of IL13Rα2-CAR T cells.
Figure 10B:
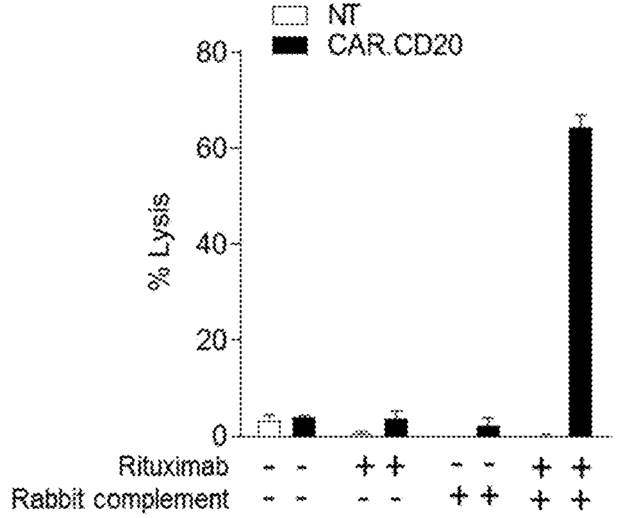
Figure 10C:
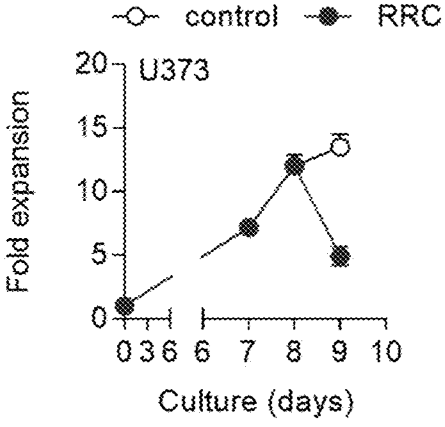

Example 7. Inclusion of CD20 as a Safety Switch Enables Efficient Depletion of IL13Rα2-CAR T Cells A retroviral vector was generated encoding an IL13Rα2-CAR.CD28z, a 2A sequence, and CD20 (FIG. 10A). To evaluate the functionality of the CD20 suicide gene, a cytotoxicity assay was performed with $^{51}$Cr-labeled NT T cells or IL13Rα2-CAR$^{CD20}$ T cells in the presence of rituximab and/or complement. While complement or rituximab alone did not induce killing of CAR T cells, about 70% killing was observed in the presence of rituximab and complement in a 4-hour chromium release assay (FIG. 10B). To test activation dependent CAR T cell expansion after treatment with rituximab and complement, a co-culture experiment was carried out with IL13Rα2+ tumor cells (U373). Eight days post co-culture set-up, cells were treated with rituximab and complement (RRC). T cell expansion was evaluated 24 hours later. Rituximab and complement treated cells lost their ability to expand when compared to rituximab only (control) treated cells (FIG. 10C). Thus, this data demonstrates that CD20 can efficiently eliminate IL13Rα2-CAR T cells via transgenic expression of CD20.

As described in the Examples above, five different LV constructs were generated which encode CD20 and CD123-CARs that differed in their antigen binding, H/TM, and/or signaling domains. CD123-CAR$^{CD20}$ T cell populations had a similar immunophenotype and effector function in vitro and in vivo except for differences in baseline signaling and recognition of normal HPCs.

It has been recognized that the effector function of CAR T cells is a direct result of the interplay of antigen recognition domain (e.g. scFv affinity, antigen density)[18], the length and flexibility of the H/TM domain[19-21] as well as the costimulatory domain selected[22-24]. Therefore, two different scFvs (26292 and 32716) were tested, using CD8α or CD28 H/TM domains and either CD28 and/or 41BB as costimulatory domains in the Examples presented above.

CAR T-cell function is influenced by the manufacturing process[26-29]. For example, it relies on CD4/CD8-selection followed by activation, transduction, and expansion of CAR T cells in the presence of IL7 and IL15. The above resulting CAR T cell products had a CD4 to CD8 ratio that was close to 1:1, a ratio that has been deemed favorable by other investigators[28,29]. Of note, this was achieved without manufacturing CD4- and CD8-positive CAR T cells separately, thus, simplifying the manufacturing process. Constructs expressing CD28 H/TM domains that also had the same signaling domain resulted in higher levels of CAR expression when compared to their counterparts expressing CD8α H/TM. While the influence of the TM on CAR cell surface expression has been reported by others[19-21,30], the Examples presented above demonstrate that this is not due to differences in the transduction efficiencies of the CAR-encoding vectors.

Resulting CD123-CAR$^{CD20}$ T-cells had similar immunophenotype, with a predominance of central and effector memory T-cell subsets. Of the generated CD123-CARs, only the construct encoding a 41BB costimulatory domain induced baseline (tonic) signaling as evidenced by significant IFNγ production without antigen specific stimulation. However, this did not translate to increased expression of markers that are associated with exhaustion such as Tim3 and PD1 in comparison to the other constructs, or a significant decrease in effector function.

In Example 5, it was observed that T cells expressing the 716 scFv-based CAR recognized HPCs to a greater extent than 292 scFv-based CARs. Both scFvs bind to different epitopes, however, they have similar affinities for CD123 that are in the nanomolar range[33]. Of interest, despite similar affinities, only a 292 scFv-based immunotoxin had significant cytotoxic activity in comparison to a 716 scFv-based immunotoxin, indicating that different binding sites within the extracellular domain of an antigen can impact the activity of immune-based approaches[34].

The antitumor activity of CD123-CAR$^{CD20}$ T cells was evaluated at two dose levels. While at the higher T cell dose there were no significant differences between CAR T cell groups, at the lower dose 716-scFv-based CD123-CAR$^{CD20}$ T cells had a significantly decreased anti-tumor activity. Of note, addition of a 41BB signaling domain to CD28.z CAR T cells did not improve antitumor activity. Incorporating a 41BB signaling domain into CD28.z CAR T cells as part of a third generation CAR improves their antitumor activity and has been studied in several models. The benefit in this instance seems to be model dependent[22,39].

REFERENCES

1. Zwaan, C. M., et al. *Collaborative Efforts Driving Progress in Pediatric Acute* Myeloid Leukemia. J Clin Oncol 33, 2949-2962 (2015).
2. Maude, S. L., et al. Chimeric antigen receptor T cells for sustained remissions in leukemia. *N Engl J Med* 371, 1507-1517 (2014).
3. Maude, S. L. Tisagenlecleucel in pediatric patients with acute lymphoblastic leukemia. *Clin Adv Hematol Oncol* 16, 664-666 (2018).
4. Locke, F. L., et al. Phase 1 Results of ZUMA-1: A Multicenter Study of KTE-C19 Anti-CD19 CAR T Cell Therapy in Refractory Aggressive Lymphoma. *Mol Ther* 25, 285-295 (2017).
5. Lee, D. W., et al. T cells expressing CD19 chimeric antigen receptors for acute lymphoblastic leukaemia in children and young adults: a phase 1 dose-escalation trial. *Lancet* 385, 517-528 (2015).
6. Kochenderfer, J. N., et al. Chemotherapy-refractory diffuse large B-cell lymphoma and indolent B-cell malignancies can be effectively treated with autologous T cells expressing an anti-CD19 chimeric antigen receptor. *J Clin Oncol* 33, 540-549 (2015).
7. Davila, M. L., et al. Efficacy and toxicity management of 19-28z CAR T cell therapy in B cell acute lymphoblastic leukemia. *Sci Transl Med* 6, 224ra225 (2014).
8. Gardner, R. A., et al. Intent-to-treat leukemia remission by CD19 CAR T cells of defined formulation and dose in children and young adults. *Blood* 129, 3322-3331 (2017).
9. Perna, F., et al. Integrating Proteomics and Transcriptomics for Systematic Combinatorial Chimeric Antigen Receptor Therapy of AML. *Cancer Cell* 32, 506-519 e505 (2017).
10. Ehninger, A., et al. Distribution and levels of cell surface expression of CD33 and CD123 in acute myeloid leukemia. *Blood Cancer J* 4, e218 (2014).
11. Gill, S., et al. Preclinical targeting of human acute myeloid leukemia and myeloablation using chimeric antigen receptor-modified T cells. *Blood* 123, 2343-2354 (2014).
12. Tasian, S. K., et al. Optimized depletion of chimeric antigen receptor T cells in murine xenograft models of human acute myeloid leukemia. *Blood* 129, 2395-2407 (2017).
13. Tashiro, H., et al. Treatment of Acute Myeloid Leukemia with T Cells Expressing Chimeric Antigen Receptors Directed to C-type Lectin-like Molecule 1. *Mol Ther* 25, 2202-2213 (2017).
14. Mardiros, A., et al. T cells expressing CD123-specific chimeric antigen receptors exhibit specific cytolytic effector functions and antitumor effects against human acute myeloid leukemia. *Blood* 122, 3138-3148 (2013).
15. Budde, L., et al. Remissions of Acute Myeloid Leukemia and Blastic Plasmacytoid Dendritic Cell Neoplasm Following Treatment with CD123-Specific CAR T Cells: A First-in-Human Clinical Trial. in *Annual Meeting for the American Society of Hematology* 811 (Atlanta, GA, 2017).
16. Bouchkouj, N., et al. FDA Approval Summary: Axicabtagene Ciloleucel for Relapsed or Refractory Large B-cell Lymphoma. *Clin Cancer Res* 25, 1702-1708 (2019).
17. O'Leary, M. C., et al. FDA Approval Summary: Tisagenlecleucel for Treatment of Patients with Relapsed or Refractory B-cell Precursor Acute Lymphoblastic Leukemia. *Clin Cancer Res* 25, 1142-1146 (2019).
18. Ramakrishna, S., et al. Modulation of Target Antigen Density Improves CAR T-*cell* Functionality and Persistence. *Clin Cancer Res* (2019).
19. Hudecek, M., et al. Receptor affinity and extracellular domain modifications affect tumor recognition by ROR1-specific chimeric antigen receptor T cells. *Clin Cancer Res* 19, 3153-3164 (2013).
20. Watanabe, N., et al. Fine-tuning the CAR spacer improves T-cell potency. *Oncoimmunology* 5, e1253656 (2016).
21. Guest, R. D., et al. The role of extracellular spacer regions in the optimal design of chimeric immune receptors: evaluation of four different scFvs and antigens. *J Immunother* 28, 203-211 (2005).
22. Long, A. H., et al. 4-1BB costimulation ameliorates T cell exhaustion induced by tonic signaling of chimeric antigen receptors. *Nat Med* 21, 581-590 (2015).
23. Kawalekar, O. U., et al. Distinct Signaling of Coreceptors Regulates Specific Metabolism Pathways and Impacts Memory Development in CAR T Cells. *Immunity* 44, 380-390 (2016).
24. Gomes-Silva, D., et al. Tonic 4-1BB Costimulation in Chimeric Antigen Receptors Impedes T Cell Survival and Is Vector-Dependent. *Cell Rep* 21, 17-26 (2017).
25. Ying, Z., et al. A safe and potent anti-CD19 CAR T cell therapy. *Nat Med* (2019).
26. Berger, C., et al. Adoptive transfer of effector CD8+ T cells derived from central memory cells establishes persistent T cell memory in primates. *J Clin Invest* 118, 294-305 (2008).
27. Alizadeh, D., et al. IL15 Enhances CAR-T Cell Antitumor Activity by Reducing mTORC1 Activity and Preserving Their Stem Cell Memory Phenotype. *Cancer Immunol Res* 7, 759-772 (2019).
28. Turtle, C. J., et al. CD19 CAR-T cells of defined CD4+:CD8+ composition in adult B cell ALL patients. *J Clin Invest* 126, 2123-2138 (2016).
29. Sommermeyer, D., et al. Chimeric antigen receptor-modified T cells derived from defined CD8+ and CD4+ subsets confer superior antitumor reactivity in vivo. *Leukemia* 30, 492-500 (2016).
30. Kunkele, A., et al. Functional Tuning of CARs Reveals Signaling Threshold above Which CD8+ CTL Antitumor Potency Is Attenuated due to Cell Fas-FasL-Dependent AICD. *Cancer Immunol Res* 3, 368-379 (2015).
31. Sauter, C. S., et al. CD19 *CART Cells Following Autologous Transplantation in Poor* Risk Relapsed and Refractory B cell non-Hodgkin Lymphoma. *Blood* (2019).
32. Fraietta, J. A., et al. Determinants of response and resistance to CD19 chimeric antigen receptor (CAR) T cell therapy of chronic lymphocytic leukemia. *Nat Med* 24, 563-571 (2018).

33. Du, X., Ho, M. & Pastan, I. New immunotoxins targeting CD123, a stem cell antigen on acute myeloid leukemia cells. *J Immunother* 30, 607-613 (2007).

34. Kunik, V., Peters, B. & Ofran, Y. Structural consensus among antibodies defines the antigen binding site. *PLoS Comput Biol* 8, e1002388 (2012).

35. Haso, W., et al. Anti-CD22-chimeric antigen receptors targeting B-cell precursor acute lymphoblastic leukemia. *Blood* 121, 1165-1174 (2013).

36. Zhang, Z., et al. Modified CAR T cells targeting membrane-proximal epitope of mesothelin enhances the antitumor function against large solid tumor. *Cell Death Dis* 10, 476 (2019).

37. Griffioen, M., et al. Retroviral transfer of human CD20 as a suicide gene for adoptive T-cell therapy. *Haematologica* 94, 1316-1320 (2009).

38. Bonifant, C. L., et al. CD123-Engager T Cells as a Novel Immunotherapeutic for Acute Myeloid Leukemia. *Molecular therapy: the journal of the American Society of Gene Therapy* 24, 1615-1626 (2016).

39. Drent, E., et al. Combined CD28 and 4-1BB Costimulation Potentiates Affinity-tuned Chimeric Antigen Receptor-engineered T Cells. *Clin Cancer Res* 25, 4014-4025 (2019).

40. Ramos, C. A., et al. In Vivo Fate and Activity of Second-versus Third-Generation CD19-Specific CAR-T Cells in B Cell Non-Hodgkin's Lymphomas. *Mol Ther* 26, 2727-2737 (2018).

41. Chan, W. K., et al. Chimeric antigen receptor-redirected CD45RA-negative T cells have potent antileukemia and pathogen memory response without graft-versus-host activity. *Leukemia* 29, 387-395 (2015).

42. McGarrity, G. J., et al. Patient monitoring and follow-up in lentiviral clinical trials. *J Gene Med* 15, 78-82 (2013).

43. Cornetta, K., et al. Absence of Replication-Competent Lentivirus in the Clinic: Analysis of Infused T Cell Products. *Molecular therapy: the journal of the American Society of Gene Therapy* 26, 280-288 (2018).

44. Throm, R. E. B., M; Wu, C.; Roberts, J. K.; Fan, B.; Ferrara, F.; Wiegolsz, M.; Ryu, B. Production of Lentiviral Vectors Using 293T Cells Adapted to Grow in Suspension with Serum-Free Media. in *ASGCT* 2018 (Chicago, IL, 2018).

45. Shaffer, D. R., et al. T cells redirected against CD70 for the immunotherapy of CD70-positive malignancies. *Blood* 117, 4304-4314 (2011).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

What is claimed is:

1. A polynucleotide encoding a chimeric antigen receptor (CAR) comprising:
   (a) a leader sequence derived from CD8α,
   (b) an anti-CD123 single chain variable fragment (scFv) comprising (i) the nucleotide sequence of SEQ ID NO: 30 encoding scFV (292) or (ii) the nucleotide sequence of SEQ ID NO: 32 encoding scFV (716),
   (c) a hinge domain derived from CD28,
   (d) a transmembrane domain derived from CD28, and
   (e) a cytoplasmic domain comprising (i) a costimulatory domain derived from CD28 and (ii) a signaling domain derived from CD3ζ.

2. The polynucleotide of claim 1, wherein scFV (292) comprises the amino acid sequence of SEQ ID NO: 29 or wherein scFV (716) comprises the amino acid sequence of SEQ ID NO: 31.

3. The polynucleotide of claim 1, wherein the leader sequence derived from CD8a comprises the amino acid sequence of SEQ ID NO: 25.

4. The polynucleotide of claim 1, wherein the hinge domain derived from CD28 comprises the amino acid sequence of SEQ ID NO: 43.

5. The polynucleotide of claim 1, wherein the transmembrane domain derived from CD28 comprises the amino acid sequence of SEQ ID NO: 45.

6. The polynucleotide of claim 1, wherein the costimulatory domain derived from CD28 comprises the amino acid sequence of SEQ ID NO: 54.

7. The polynucleotide of claim 1, wherein the signaling domain derived from CD33 comprises the amino acid sequence of SEQ ID NO: 58 or 60.

8. The polynucleotide of claim 1, wherein the CAR comprises the amino acid sequence of SEQ ID NO: 7.

9. The polynucleotide of claim 8, wherein the polynucleotide comprises the nucleotide sequence of SEQ ID NO: 8.

10. A chimeric antigen receptor (CAR) encoded by the polynucleotide of claim 1.

11. The polynucleotide of claim 1, further comprising a sequence encoding a CD20 polypeptide.

12. The polynucleotide of claim 11, wherein the CD20 polypeptide comprises the amino acid sequence of SEQ ID NO: 62, or an amino acid sequence having at least 80% identity thereof.

13. The polynucleotide of claim 12, wherein the nucleotide sequence encoding the CD20 polypeptide comprises the nucleotide sequence of SEQ ID NO: 63 or 64, or a nucleotide sequence having at least 80% identity thereof.

14. The polynucleotide of claim 11, wherein the sequence encoding the CD20 polypeptide is operably linked to the sequence encoding CAR via a sequence encoding a self-cleaving peptide or an Internal Ribosome Entry Site (IRES).

15. A pharmaceutical composition comprising the polynucleotide of claim 1 or a recombinant vector comprising said polynucleotide, and a pharmaceutically accepted carrier and/or excipient.

* * * * *